United States Patent
Steyaert et al.

(10) Patent No.: US 10,233,241 B2
(45) Date of Patent: Mar. 19, 2019

(54) OPIOID RECEPTOR BINDING AGENTS AND USES THEREOF

(71) Applicants: VIB VZW, Ghent (BE); Vrije Universiteit Brussel, Brussels (BE); The Board of Trustees of the Leland Stanford Junior University, Palo Alto, CA (US)

(72) Inventors: Jan Steyaert, Beersel (BE); Toon Laeremans, Dworp (BE); Els Pardon, Lubbeek (BE); Brian Kobilka, Palo Alto, CA (US); Aashish Manglik, Menlo Park, CA (US)

(73) Assignees: VIB VZW, Ghent (BE); VRIJE UNIVERSITEIT BRUSSEL, Brussels (BE); THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 0 days.

(21) Appl. No.: 15/115,621

(22) PCT Filed: Jan. 30, 2015

(86) PCT No.: PCT/EP2015/051991
§ 371 (c)(1),
(2) Date: Jul. 29, 2016

(87) PCT Pub. No.: WO2015/121092
PCT Pub. Date: Aug. 20, 2015

(65) Prior Publication Data
US 2017/0183404 A1    Jun. 29, 2017

Related U.S. Application Data

(60) Provisional application No. 61/933,742, filed on Jan. 30, 2014.

(51) Int. Cl.
| C07K 16/28 | (2006.01) |
| C07K 14/72 | (2006.01) |
| G01N 33/68 | (2006.01) |
| G01N 33/50 | (2006.01) |
| C07K 14/705 | (2006.01) |

(52) U.S. Cl.
CPC .......... *C07K 16/28* (2013.01); *C07K 14/705* (2013.01); *C07K 14/723* (2013.01); *G01N 33/5041* (2013.01); *G01N 33/6854* (2013.01); *C07K 2317/22* (2013.01); *C07K 2317/33* (2013.01); *C07K 2317/565* (2013.01); *C07K 2317/567* (2013.01); *C07K 2317/569* (2013.01); *G01N 2333/726* (2013.01)

(58) Field of Classification Search
CPC .... C07K 16/28; C07K 14/723; C07K 14/705; C07K 2317/569; C07K 2317/33; C07K 2317/565; C07K 2317/567; C07K 2317/22; G01N 33/6854; G01N 33/5041; G01N 2333/726

See application file for complete search history.

(56) References Cited

U.S. PATENT DOCUMENTS 5,882,944 A * 3/1999 Sadee .................... A61K 31/47
435/7.1

FOREIGN PATENT DOCUMENTS

| EP | 1134231 | 9/2001 |
| WO | 9404678 | 3/1994 |
| WO | 9425591 | 11/1994 |
| WO | 9504079 | 2/1995 |
| WO | 9634103 | 10/1996 |
| WO | 9749805 | 12/1997 |
| WO | 9937681 | 7/1999 |
| WO | 2000040968 | 7/2000 |
| WO | 2000043507 | 7/2000 |
| WO | 2000065057 | 11/2000 |
| WO | 2001021817 | 3/2001 |
| WO | 2001040310 | 6/2001 |
| WO | 2001044301 | 6/2001 |
| WO | 2001090190 | 11/2001 |
| WO | 2002048193 | 6/2002 |
| WO | 2002085945 | 10/2002 |
| WO | 2003025020 | 3/2003 |
| WO | 2003035694 | 5/2003 |
| WO | 2003054016 | 7/2003 |
| WO | 2003055527 | 7/2003 |
| WO | 2004049794 | 6/2004 |
| WO | 2004060965 | 7/2004 |
| WO | 2006079372 | 8/2006 |
| WO | 2006122786 | 11/2006 |

(Continued)

OTHER PUBLICATIONS

Mace et al., Identification of micro-Opioid Receptor Epitopes Recognized by Agonistic IgG, Biochemical and Biophysical Research Communications, 2001, pp. 1142-1147, vol. 280, Academic Press.
Gupta et al., Conformation State-sensitive Antibodies to G-protein-coupled Receptors, The Journal of Biological Chemistry, Feb. 23, 2007, pp. 5116-5124, vol. 282, No. 8, The American Society for Biochemistry and Molecular Biology, Inc.
Gupta et al., Post-activation-mediated Changes in Opioid Receptors Detected by N-terminal Antibodies, The Journal of Biological Chemistry, Apr. 18, 2008, pp. 10735-10744, vol. 283, No. 16, The American Society for Biochemistry and Molecular Biology, Inc.

(Continued)

*Primary Examiner* — Ruixiang Li
(74) *Attorney, Agent, or Firm* — Patent Law Works LLP

(57) ABSTRACT

Agents that specifically bind to an opioid receptor in a conformationally specific way can be used to induce a conformational change in the receptor. Such agents have therapeutic applications and can be used in X-ray crystallography studies of the receptor. Such agents can also be used to improve drug discovery via compound screening and/or structure-based drug design.

15 Claims, 9 Drawing Sheets

Specification includes a Sequence Listing.

(56) References Cited

FOREIGN PATENT DOCUMENTS

| WO | 2006122787 | 11/2006 |
|----|------------|---------|
| WO | 2006122825 | 11/2006 |
| WO | 2008020079 | 2/2008 |
| WO | 2008101985 | 8/2008 |
| WO | 2008142164 | 11/2008 |
| WO | 2010066740 | 6/2010 |
| WO | 2010070145 | 6/2010 |
| WO | 2011083141 | 7/2011 |
| WO | 2012030735 | 3/2012 |
| WO | 2012148586 | 11/2012 |
| WO | 2012158555 | 11/2012 |
| WO | 2014118297 | 8/2014 |
| WO | 2015121092 | 8/2015 |

OTHER PUBLICATIONS

Rasmussen, Soren G. F., et al., "Structure of a nanobody-stabilized active state of the .beta.2 adrenoceptor," Nature, Nature Publishing Group, United Kingdom, vol. 469, No. 7329, Jan. 13, 2011, pp. 175-180.

Kruse et al., Activation and allosteric modulation of muscarinic acetylcholine receptor, Nature, Dec. 5, 2013, pp. 101-106, vol. 504, No. 7478.

PCT International Search Report dated Aug. 5, 2015, PCT/EP2015/051991.

PCT Written Opinion dated Aug. 5, 2015, PCT/EP2015/051991.

\* cited by examiner

FIG. 7

OPIOID RECEPTOR BINDING AGENTS AND USES THEREOF

CROSS-REFERENCE TO RELATED APPLICATIONS

This application is a national phase entry under 35 U.S.C. § 371 of International Patent Application PCT/EP2015/051991, filed Jan. 30, 2015, designating the United States of America and published in English as International Patent Publication WO 2015/121092 A1 on Aug. 20, 2015, which claims the benefit under Article 8 of the Patent Cooperation Treaty to U.S. Provisional Patent Application Ser. No. 61/933,742, filed Jan. 30, 2014.

STATEMENT ACCORDING TO 37 C.F.R. § 1.821(c) OR (e)—SEQUENCE LISTING SUBMITTED AS ASCII TEXT FILE

Pursuant to 37 C.F.R. § 1.821(c) or (e), a file containing an ASCII text version of the Sequence Listing has been submitted concomitant with this application, the contents of which are hereby incorporated by reference.

TECHNICAL FIELD

This application relates generally to biotechnology and medicine. Many transmembrane receptors such as G protein-coupled receptors (GPCRs) exist in many interconvertible three-dimensional conformations depending on their activity or ligand-binding state. Agents that specifically bind to a transmembrane receptor in a conformationally specific way can be used to induce a conformational change in the transmembrane receptor. Such agents have therapeutic applications and can be used in X-ray crystallography studies of the transmembrane receptor. Such agents can also be used to improve drug discovery via compound screening and/or structure-based drug design.

BACKGROUND

Pain is a complex disorder with neurochemical and psychological components contributing to the severity, the persistence, and the difficulty in adequately treating the condition. Opioids and cannabinoids are two classes of analgesics that have been used to treat pain for centuries and are arguably the oldest of "pharmacological" interventions used by man. Unfortunately, they also produce several adverse side effects that can complicate pain management.

Opioids produce their pharmacological effects through activation of G protein-coupled receptors (GPCRs). There are four distinct genes coding for opioid receptors: the mu-, kappa-, and delta-opioid receptors (MOR, KOR, and DOR, respectively) and the opioid-like receptor1 [ORL-1 or the nociceptin receptor (NOP)] (Cox 2012; Pasternak 2013). The generation of genetic knockout mice has demonstrated that the majority of clinically used opioids including morphine produce their pharmacological effects primarily by activating the MOR (Matthes et al., 1996; Sora et al., 1997; Roy et al., 1998; Kieffer 1999; Kieffer and Gaveriaux-Ruff 2002). The MOR is widely distributed and expressed in neurons in the brain, spinal cord, and the periphery (Gutstein and Akil 2001).

The pharmacological and genetic studies of rodents to date suggests that the development of opioid agonists that bias MOR toward G protein signaling cascades and away from β-arrestin interactions may provide a novel mechanism by which to produce analgesia with less severe adverse effects. Presently, there have been a few reports of "biased" MOR agonists and their effects in vivo. One such compound herkinorin is a selective MOR agonist that does not recruit β-arrestin1 or β-arrestin2 in cell culture assays (Groer et al., 2007). In an inflammatory pain model in rat, herkinorin reduces formalin-induced flinching to the same degree as morphine when administered at the same dose (10 mg/kg, i.pl.), an effect that is reversed by the opioid antagonist naloxone (Lamb et al., 2012). Moreover, antinociceptive tolerance to herkinorin does not develop to repeated treatment over a 5-day period and it produces antinociception in morphine-tolerant rats (Lamb et al., 2012). The initial studies with these MOR "biased" agonists lend further support to the idea that developing a MOR agonist that does not engage β-arrestins but fully activates G protein signaling may provide a novel therapeutic avenue to improve pain treatment with opioids.

The binding of an activating ligand (agonist) to the extracellular side of a GPCR results in conformational changes that enable the receptor to activate heterotrimeric G proteins. Despite the importance of this process, only the β-adrenergic receptor, the M2 muscarinic receptor and rhodopsin have been crystallized and their structures solved in agonist-bound active-state conformations (Choe et al., 2011; Rasmussen et al., 2011a; Rasmussen et al., 2011b; Deupi et al., 2012; Scheerer et al., 2008; Kruse et al., 2013). Crystallization of agonist-bound active-state GPCRs has been extremely challenging due to their inherent conformational flexibility. Fluorescence and NMR experiments have shown that the conformational stabilization of the agonist-bound active-state conformation requires that the receptor must form a complex with an agonist and its G protein, or some other binding protein that stabilizes the active conformation (Yao et al., 2009; Nygaard et al., 2013).

The crystal structure of MOR available today will enable the application of structure-based approaches to design better drugs for the management of pain, addiction and other human diseases, where MORs play a key role. Though crystal structures were obtained for the μ-opioid receptor bound to an antagonist (Manglik et al., 2012), experimental data that reveal the agonist-bound active state opioid receptor protein structure have not been reported. Such information could greatly facilitate the development of novel agents, not only with increased potency and selectivity, but eventually also biased agonists.

The development of new straightforward tools for structural and pharmacological analysis of GPCR drug targets is therefore needed.

BRIEF DESCRIPTION OF THE FIGURES

The skilled artisan will understand that the drawings, described below, are for illustration purposes only. The drawings are not intended to limit the scope of the present teachings in any way.

FIG. 7. AA sequence alignment of the Mor1-specific Nanobodies. Delineation of complementarity-determining (CDR) and framework (FR) regions is according to IMGT numbering (Lefranc et al., 2003). Point mutations are indicated in grey shade (SEQ ID NOS: 82-87).

FIG. 11. Binding properties of monovalent and bivalent XA8635 in flow cytometry. The mean cell fluorescence values of monovalent XA8635 (mono) and bivalent XA8635 (bi 9GS) were determined on human Mori transfected CHO cells (Mor1/CHO) and on non-transfected parental CHO cells (CHO). As negative controls, background fluorescence detected in the phycoerythrin (PE) compatible channel was determined on non-stained cells (unstained) and on cells stained with the distinct detection reagents: Topro3 (topro), anti-cMyc tag mAb followed by anti-mouse-PE (a cMyc_PE), anti-Flag mab followed by anti-mouse-PE (aFlag_PE) or an anti mouse-PE conjugate (aMousePE).

FIG. 12. Binding properties of mu-opioid receptor agonist BU72 in presence of Gi or XA8639. Dose-dependent radioligand displacement curves are generated using cold BU72 in presence of Gi protein (upper panel) or G-protein mimetic XA8639 (indicated as Nb39; lower panel). The opioid receptor is reconstituted in high density lipoprotein particles (HDLs).

FIG. 13. XA8639 enables to solve the active state structure of the mu-opioid receptor bound to agonist BU72 by X-ray crystallography.

DEFINITIONS

Figure 1:
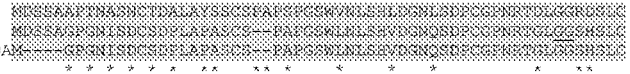
FIG. 1. AA sequence alignment of WT human Mor1 (Uniprot code P35372), WT mouse Mor1 (Uniprot code P42866) and recombinant Delta mMor1 used for insect cell expression. The introduced TEV and 3C cleavage sequences are not depicted in the figure but are introduced between the AA residues of the single underlined residues. The theoretical topological domains according to the Uniprot database are depicted: the N-terminus and the three extracellular loops in grey shade, the intracellular loops and the C-terminus are double underlined. Flag and His tags are indicated in bold. AA residues that are not conserved are indicated with an asterisk.

The disclosure will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun, e.g., "a," "an," or "the," this includes a plural of that noun unless something else is specifically stated. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments described herein are capable of operation in other sequences than described or illustrated herein.

Unless otherwise defined herein, scientific and technical terms and phrases used in connection with the disclosure shall have the meanings that are commonly understood by those of ordinary skill in the art. Generally, nomenclatures used in connection with, and techniques of molecular and cellular biology, structural biology, biophysics, pharmacology, genetics and protein and nucleic acid chemistry described herein are those well known and commonly used in the art. Singleton, et al., Dictionary of Microbiology and Molecular Biology, 2D ED., John Wiley and Sons, New York (1994), and Hale & Marham, The Harper Collins Dictionary of Biology, Harper Perennial, N.Y. (1991), provide one of skill with general dictionaries of many of the terms used in this invention. The methods and techniques of the disclosure are generally performed according to conventional methods well known in the art and as described in various general and more specific references that are cited and discussed throughout the present specification unless otherwise indicated. See, for example, Sambrook et al., Molecular Cloning: A Laboratory Manual, $3^{rd}$ ed., Cold Spring Harbor Laboratory Press, Cold Spring Harbor, N.Y. (2001); Ausubel et al., Current Protocols in Molecular Biology, Greene Publishing Associates (1992, and Supplements to 2002); Rup, Biomolecular crystallography: principles, Practice and Applications to Structural Biology, $1^{st}$ edition, Garland Science, Taylor & Francis Group, LLC, an informa Business, N.Y. (2009); Limbird, Cell Surface Receptors, 3d ed., Springer (2004).

As used herein, the terms "polypeptide," "protein," and "peptide" are used interchangeably herein, and refer to a polymeric form of amino acids of any length, which can include coded and non-coded amino acids, chemically or biochemically modified or derivatized amino acids, and polypeptides having modified peptide backbones. Throughout the application, the standard one letter notation of amino acids will be used. Typically, the term "amino acid" will refer to "proteinogenic amino acid," i.e., those amino acids that are naturally present in proteins. Most particularly, the amino acids are in the L isomeric form, but D amino acids are also envisaged.

As used herein, the terms "nucleic acid molecule," "polynucleotide," "polynucleic acid," and "nucleic acid" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

Any of the peptides, polypeptides, nucleic acids, compound, etc., disclosed herein, may be "isolated" or "purified." "Isolated" is used herein to indicate that the material referred to is (i) separated from one or more substances with which it exists in nature (e.g., is separated from at least some cellular material, separated from other polypeptides, separated from its natural sequence context), and/or (ii) is produced by a process that involves the hand of man such as recombinant DNA technology, chemical synthesis, etc.; and/ or (iii) has a sequence, structure, or chemical composition not found in nature. "Isolated" is meant to include compounds that are within samples that are substantially enriched for the compound of interest and/or in which the compound of interest is partially or substantially purified. "Purified" as used herein denote that the material referred to is removed from its natural environment and is at least 60% free, at least 75% free, or at least 90% free from other components with which it is naturally associated, also referred to as being "substantially pure."

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Determining the percentage of sequence identity can be done manually, or by making use of computer programs that are available in the art. Examples of useful algorithms are PILEUP (Higgins & Sharp, CABIOS 5:151 (1989), BLAST and BLAST 2.0 (Altschul et al., J. Mol. Biol. 215:403 (1990). Software for performing BLAST analyses is publicly available through the National Center for Biotechnology Information (on the World Wide web at ncbi.nlm.nih.gov/).

"Similarity" refers to the percentage number of amino acids that are identical or constitute conservative substitutions. Similarity may be determined using sequence comparison programs such as GAP (Deveraux et al., 1984). In this way, sequences of a similar or substantially different length to those cited herein might be compared by insertion of gaps into the alignment, such gaps being determined, for example, by the comparison algorithm used by GAP. As used herein, "conservative substitution" is the substitution of amino acids with other amino acids whose side chains have similar biochemical properties (e.g., are aliphatic, are aromatic, are positively charged, . . . ) and is well known to the skilled person. Non-conservative substitution is then the substitution of amino acids with other amino acids whose side chains do not have similar biochemical properties (e.g., replacement of a hydrophobic with a polar residue). Conservative substitutions will typically yield sequences which are not identical anymore, but still highly similar. By conservative substitutions is intended combinations such as gly, ala; val, ile, leu, met; asp, glu; asn, gln; ser, thr; lys, arg; cys, met; and phe, tyr, trp.

A "deletion" is defined here as a change in either amino acid or nucleotide sequence in which one or more amino acid or nucleotide residues, respectively, are absent as compared to an amino acid sequence or nucleotide sequence of a parental polypeptide or nucleic acid. Within the context of a protein, a deletion can involve deletion of about 2, about 5, about 10, up to about 20, up to about 30 or up to about 50 or more amino acids. A protein or a fragment thereof may contain more than one deletion. Within the context of a GPCR, a deletion may also be a loop deletion, or an N- and/or C-terminal deletion, or a combination thereof. As will be clear to the skilled person, an N- and/or C-terminal deletion of a GPCR is also referred to as a truncation of the amino acid sequence of the GPCR or a truncated GPCR.

An "insertion" or "addition" is that change in an amino acid or nucleotide sequences, which has resulted in the addition of one or more amino acid or nucleotide residues, respectively, as compared to an amino acid sequence or nucleotide sequence of a parental protein. "Insertion" generally refers to addition to one or more amino acid residues within an amino acid sequence of a polypeptide, while "addition" can be an insertion or refer to amino acid residues added at an N- or C-terminus, or both termini. Within the context of a protein or a fragment thereof, an insertion or addition is usually of about 1, about 3, about 5, about 10, up to about 20, up to about 30 or up to about 50 or more amino acids. A protein or fragment thereof may contain more than one insertion.

A "substitution," as used herein, results from the replacement of one or more amino acids or nucleotides by different amino acids or nucleotides, respectively, as compared to an amino acid sequence or nucleotide sequence of a parental protein or a fragment thereof. It is understood that a protein or a fragment thereof may have conservative amino acid substitutions which have substantially no effect on the protein's activity. By conservative substitutions is intended combinations such as gly, ala; val, ile, leu, met; asp, glu; asn, gln; ser, thr; lys, arg; cys, met; and phe, tyr, trp.

The term "recombinant," when used in reference to a cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express nucleic acids or polypeptides that are not found within the native (non-recombinant) form of the cell or express native genes that are otherwise abnormally expressed, under expressed, over expressed or not expressed at all.

As used herein, the term "expression" refers to the process by which a polypeptide is produced based on the nucleic acid sequence of a gene. The process includes both transcription and translation.

The term "operably linked" as used herein refers to a linkage in which the regulatory sequence is contiguous with the gene of interest to control the gene of interest, as well as regulatory sequences that act in trans or at a distance to control the gene of interest. For example, a DNA sequence is operably linked to a promoter when it is ligated to the promoter downstream with respect to the transcription initiation site of the promoter and allows transcription elongation to proceed through the DNA sequence. A DNA for a signal sequence is operably linked to DNA coding for a polypeptide if it is expressed as a pre-protein that participates in the transport of the polypeptide. Linkage of DNA sequences to regulatory sequences is typically accomplished by ligation at suitable restriction sites or adapters or linkers inserted in lieu thereof using restriction endonucleases known to one of skill in the art.

The term "regulatory sequence" as used herein refers to polynucleotide sequences which are necessary to affect the expression of coding sequences to which they are operably linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRMA; sequences that enhance translation efficiency (e.g., ribosome binding sites); sequences that enhance protein stability; and when desired, sequences that enhance protein secretion. The nature of such control sequences differs depending upon the host organism. The term "control sequences" is intended to include, at a minimum, all components whose presence is essential for expression, and can also include additional components whose presence is advantageous, for example, leader sequences and fusion partner sequences.

The term "vector" as used herein is intended to refer to a nucleic acid molecule capable of transporting another nucleic acid molecule to which it has been linked. The vector may be of any suitable type including, but not limited to, a phage, virus, plasmid, phagemid, cosmid, bacmid or even an artificial chromosome. Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of certain genes of interest. Such vectors are referred to herein as "recombinant expression vectors" (or simply, "expression vectors"). Suitable vectors have regulatory sequences, such as promoters, enhancers, terminator sequences, and the like as desired and according to a particular host organism (e.g., bacterial cell, yeast cell). Typically, a recombinant vector according to the disclosure comprises at least one "chimeric gene" or "expression cassette." Expression cassettes are generally DNA constructs preferably including (5' to 3' in the direction of transcription): a promoter region, a polynucleotide sequence, homologue, variant or fragment thereof of the disclosure operably linked with the transcription initiation region, and a termination sequence including a stop signal for RNA polymerase and a polyadenylation signal. It is understood that all of these regions should be capable of operating in biological cells, such as prokaryotic or eukaryotic cells, to be transformed. The promoter region comprising the transcription initiation region, which preferably includes the RNA polymerase binding site, and the polyadenylation signal may be native to the biological cell to be transformed or may be derived from an alternative source, where the region is functional in the biological cell.

The term "host cell," as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A host cell may be an isolated cell or cell line grown in culture or may be a cell which resides in a living tissue or organism. In particular, host cells are of bacterial or fungal origin, but may also be of plant or mammalian origin. The wordings "host cell," "recombinant host cell," "expression host cell," "expression host system," and "expression system" are intended to have the same meaning and are used interchangeably herein.

"G-protein coupled receptors" or "GPCRs" are polypeptides that share a common structural motif, having seven regions of between 22 to 24 hydrophobic amino acids that form seven alpha helices, each of which spans a membrane. Each span is identified by number, i.e., transmembrane-1 (TM1), transmembrane-2 (TM2), etc. The transmembrane helices are joined by regions of amino acids between transmembrane-2 and transmembrane-3, transmembrane-4 and transmembrane-5, and transmembrane-6 and transmembrane-7 on the exterior, or "extracellular" side, of the cell membrane, referred to as "extracellular" regions 1, 2 and 3 (EC1, EC2 and EC3), respectively. The transmembrane helices are also joined by regions of amino acids between transmembrane-1 and transmembrane-2, transmembrane-3 and transmembrane-4, and transmembrane-5 and transmembrane-6 on the interior, or "intracellular" side, of the cell membrane, referred to as "intracellular" regions 1, 2 and 3 (IC1, IC2 and IC3), respectively. The "carboxy" ("C") terminus of the receptor lies in the intracellular space within the cell, and the "amino" ("N") terminus of the receptor lies in the extracellular space outside of the cell. GPCR structure and classification is generally well known in the art, and further discussion of GPCRs may be found in Probst, DNA Cell Biol. 1992 11:1-20; Marchese et al., Genomics 23: 609-618, 1994; and the following books: Jürgen Wess (Ed) Structure-Function Analysis of G Protein-Coupled Receptors published by Wiley Liss (1st edition; Oct. 15, 1999); Kevin R. Lynch (Ed) Identification and Expression of G Protein-Coupled Receptors published by John Wiley & Sons (March 1998); Tatsuya Haga (Ed), G Protein-Coupled Receptors, published by CRC Press (Sep. 24, 1999); and Steve Watson (Ed) G-Protein Linked Receptor Factsbook, published by Academic Press (1st edition; 1994).

The term "biologically active," with respect to a GPCR, refers to a GPCR having a biochemical function (e.g., a binding function, a signal transduction function, or an ability to change conformation as a result of ligand binding) of a naturally occurring GPCR.

In general, the term "naturally occurring" in reference to a GPCR means a GPCR that is naturally produced (e.g., by a wild-type mammal such as a human). Such GPCRs are found in nature. The term "non-naturally occurring" in reference to a GPCR means a GPCR that is not naturally occurring. Naturally occurring GPCRs that have been made constitutively active through mutation and variants of naturally occurring transmembrane receptors, e.g., epitope-tagged GPCRs and GPCRs lacking their native N-terminus are examples of non-naturally occurring GPCRs. Non-naturally occurring versions of a naturally occurring GPCR are often activated by the same ligand as the naturally occurring GPCR. Non-limiting examples of either naturally occurring or non-naturally occurring GPCRs within the context of the disclosure are provided further herein, in particular for opioid receptors.

An "epitope," as used herein, refers to an antigenic determinant of a polypeptide. An epitope could comprise 3 amino acids in a spatial conformation, which is unique to the epitope. Generally an epitope consists of at least 4, 5, 6, 7 such amino acids, and more usually, consists of at least 8, 9, 10 such amino acids. Methods of determining the spatial conformation of amino acids are known in the art, and include, for example, x-ray crystallography and multi-dimensional nuclear magnetic resonance. A "conformational epitope," as used herein, refers to an epitope comprising amino acids in a spatial conformation that is unique to a folded three-dimensional conformation of the polypeptide. Generally, a conformational epitope consists of amino acids that are discontinuous in the linear sequence that come together in the folded structure of the protein. However, a conformational epitope may also consist of a linear sequence of amino acids that adopts a conformation that is unique to a folded three-dimensional conformation of the polypeptide (and not present in a denatured state).

The term "conformation" or "conformational state" of a protein refers generally to the range of structures that a protein may adopt at any instant in time. One of skill in the art will recognize that determinants of conformation or conformational state include a protein's primary structure as reflected in a protein's amino acid sequence (including modified amino acids) and the environment surrounding the protein. The conformation or conformational state of a protein also relates to structural features such as protein secondary structures (e.g., α-helix, β-sheet, among others), tertiary structure (e.g., the three-dimensional folding of a polypeptide chain), and quaternary structure (e.g., interactions of a polypeptide chain with other protein subunits). Post-translational and other modifications to a polypeptide chain such as ligand binding, phosphorylation, sulfation, glycosylation, or attachments of hydrophobic groups, among others, can influence the conformation of a protein. Furthermore, environmental factors, such as pH, salt concentration, ionic strength, and osmolality of the surrounding solution, and interaction with other proteins and co-factors, among others, can affect protein conformation. The conformational state of a protein may be determined by either functional assay for activity or binding to another molecule or by means of physical methods such as X-ray crystallography, NMR, or spin labeling, among other methods. For a general discussion of protein conformation and conformational states, one is referred to Cantor and Schimmel, Biophysical Chemistry, Part I: The Conformation of Biological. Macromolecules, W.H. Freeman and Company, 1980, and Creighton, Proteins: Structures and Molecular Properties, W.H. Freeman and Company, 1993.

A "functional conformation" or a "functional conformational state," as used herein, refers to the fact that proteins possess different conformational states having a dynamic range of activity, in particular ranging from no activity to maximal activity. It should be clear that "a functional conformational state" is meant to cover any conformational state of a protein, having any activity, including no activity, and is not meant to cover the denatured states of proteins. Non-limiting examples of functional conformations include active conformations or inactive conformations (as defined further herein). A particular class of functional conformations is defined as "druggable conformation" and generally refers to a unique therapeutically relevant conformational state of a target protein. As an illustration, the agonist-bound active conformation of the mu-opioid receptor corresponds to the druggable conformation of this receptor relating to pain. It will thus be understood that druggability is confined to particular conformations depending on the therapeutic indication. More details are provided further herein.

As used herein, the terms "active conformation" and "active form" refer to a GPCR, particularly an opioid receptor that is folded in a way so as to be active. A GPCR can be placed into an active conformation using an agonist of the receptor. For example, a GPCR in its active conformation binds to heterotrimeric G protein and catalyzes nucleotide exchange of the G-protein to activate downstream signaling pathways. Activated GPCRs bind to the inactive, GDP-bound form of heterotrimeric G-proteins and cause the G-proteins to release their GDP so GTP can bind. There is a transient "nucleotide-free" state that results from this process that enables GTP to bind. Once GTP is bound, the receptor and G-protein dissociate, allowing the GTP-bound G protein to activate downstream signaling pathways such as adenylyl cyclase, ion channels, RAS/MAPK, etc. The terms "inactive conformation" and "inactive form" refer to a GPCR, particularly opioid receptor, that is folded in a way so as to be inactive. A GPCR can be placed into an inactive conformation using an inverse agonist of the receptor. For example, a GPCR in its inactive conformation does not bind to heterotrimeric G protein with high affinity. The terms "active conformation" and "inactive conformation" will be illustrated further herein.

The term "stabilizing" or "stabilized," with respect to a functional conformational state of a GPCR, as used herein, refers to the retaining or holding of a GPCR protein in a subset of the possible conformations that it could otherwise assume, due to the effects of the interaction of the GPCR with the binding agent according to the invention. Within this context, a binding agent that selectively binds to a specific conformation or conformational state of a protein refers to a binding agent that binds with a higher affinity to a protein in a subset of conformations or conformational states than to other conformations or conformational states that the protein may assume. One of skill in the art will recognize that binding agents that specifically or selectively bind to a specific conformation or conformational state of a protein will stabilize this specific conformation or conformational state.

The term "affinity," as used herein, refers to the degree to which a ligand binds to an antigen on a receptor so as to shift the equilibrium of receptor and ligand toward the presence of a complex formed by their binding. Thus, for example, where an antigenic target and antibody (fragment) are combined in relatively equal concentration, an antibody (fragment) of high affinity will bind to the available antigen so as to shift the equilibrium toward high concentration of the resulting complex. The dissociation constant is commonly used to describe the affinity between the binding domain and the antigenic target. Typically, the dissociation constant is lower than 10-5 M. Preferably, the dissociation constant is lower than 10-6 M, more preferably, lower than 10-7 M. Most preferably, the dissociation constant is lower than 10-8 M. Other ways of describing the affinity between a ligand and its target protein are the association constant (Ka), the inhibition constant (Ki), or indirectly by evaluating the potency of ligands by measuring the half maximal inhibitory concentration (IC50) or half maximal effective concentration (EC50). Within the scope of the disclosure, the ligand may be a binding agent, preferably an immunoglobulin, such as an antibody, or an immunoglobulin fragment, such as a VHH or Nanobody, that binds a conformational epitope on a GPCR.

The term "specificity," as used herein, refers to the ability of a binding agent, in particular an immunoglobulin or an immunoglobulin fragment, such as a VHH or Nanobody, to bind preferentially to one antigen, versus a different antigen, and does not necessarily imply high affinity.

The terms "specifically bind" and "specific binding," as used herein, generally refers to the ability of a binding agent, in particular an immunoglobulin, such as an antibody, or an immunoglobulin fragment, such as a VHH or Nanobody, to preferentially bind to a particular antigen that is present in a homogeneous mixture of different antigens. In certain embodiments, a specific binding interaction will discriminate between desirable and undesirable antigens in a sample, in some embodiments more than about 10 to 100-fold or more (e.g., more than about 1000- or 10,000-fold). Within the context of the spectrum of conformational states of GPCRs, in particular opioid receptor, the terms particularly refer to the ability of a binding agent (as defined herein) to preferentially recognize and/or bind to a particular conformational state of a GPCR as compared to another conformational state.

As used herein, the term "conformation-selective binding agent" in the context of the disclosure refers to a binding agent that binds to a target protein in a conformation-selective manner. A binding agent that selectively binds to a particular conformation or conformational state of a protein refers to a binding agent that binds with a higher affinity to a protein in a subset of conformations or conformational states than to other conformations or conformational states that the protein may assume. One of skill in the art will recognize that binding agents that selectively bind to a specific conformation or conformational state of a protein will stabilize or retain the protein it this particular conformation or conformational state. For example, an active state conformation-selective binding agent will preferentially bind to a GPCR in an active conformational state and will not or to a lesser degree bind to a GPCR in an inactive conformational state, and will thus have a higher affinity for the active conformational state; or vice versa. The terms "specifically bind," "selectively bind," "preferentially bind," and grammatical equivalents thereof, are used interchangeably herein. The terms "conformational specific" or "conformational selective" are also used interchangeably herein.

The terms "compound," "test compound," "candidate compound," or "drug candidate compound," as used herein, describe any molecule, either naturally occurring or synthetic that is tested in an assay, such as a screening assay or drug discovery assay. As such, these compounds comprise organic or inorganic compounds. The compounds include polynucleotides, lipids or hormone analogs that are characterized by low molecular weights. Other biopolymeric organic test compounds include small peptides or peptide-like molecules (peptidomimetics) comprising from about 2 to about 40 amino acids and larger polypeptides comprising from about 40 to about 500 amino acids, such as antibodies, antibody fragments or antibody conjugates. Test compounds can also be protein scaffolds. For high-throughput purposes, test compound libraries may be used, such as combinatorial or randomized libraries that provide a sufficient range of diversity. Examples include, but are not limited to, natural compound libraries, allosteric compound libraries, peptide libraries, antibody fragment libraries, synthetic compound libraries, fragment-based libraries, phage-display libraries, and the like. A more detailed description can be found further in the specification.

As used herein, the term "ligand" means a molecule that specifically binds to a GPCR, in particular an opioid receptor. A ligand may be, without the purpose of being limitative, a polypeptide, a lipid, a small molecule, an antibody, an antibody fragment, a nucleic acid, a carbohydrate. A ligand may be synthetic or naturally occurring. A ligand also includes a "native ligand," which is a ligand that is an endogenous, natural ligand for a native GPCR. Within the context of the disclosure, a ligand may bind to a GPCR, either intracellularly or extracellularly. A ligand may be an agonist, a partial agonist, an inverse agonist, an antagonist, an allosteric modulator, and may bind at either the orthosteric site or at an allosteric site. In particular embodiments, a ligand may be a "conformation-selective ligand" or "conformation-specific ligand," meaning that such a ligand binds the GPCR in a conformation-selective manner. A conformation-selective ligand binds with a higher affinity to a particular conformation of the GPCR than to other conformations the GPCR may adopt. For the sake of clarity, a neutral antagonist is not considered as a conformation-selective ligand, since a neutral antagonist does not distinguish between the different conformations of a GPCR.

An "orthosteric ligand," as used herein, refers to a ligand (both natural and synthetic), that binds to the active site of a GPCR, in particular opioid receptor, and are further classified according to their efficacy or in other words to the effect they have on signaling through a specific pathway. As used herein, an "agonist" refers to a ligand that, by binding a receptor protein, increases the receptor's signaling activity. Full agonists are capable of maximal protein stimulation; partial agonists are unable to elicit full activity even at saturating concentrations. Partial agonists can also function as "blockers" by preventing the binding of more robust agonists. An "antagonist," also referred to as a "neutral antagonist," refers to a ligand that binds a receptor without stimulating any activity. An "antagonist" is also known as a "blocker" because of its ability to prevent binding of other ligands and, therefore, block agonist-induced activity. Further, an "inverse agonist" refers to an antagonist that, in addition to blocking agonist effects, reduces a receptor's basal or constitutive activity below that of the unliganded protein.

Ligands, as used herein, may also be "biased ligands" with the ability to selectively stimulate a subset of a receptor's signaling activities, for example, in the case of GPCRs the selective activation of G-protein or β-arrestin function. Such ligands are known as "biased ligands," "biased agonists" or "functionally selective agonists." More particularly, ligand bias can be an imperfect bias characterized by a ligand stimulation of multiple receptor activities with different relative efficacies for different signals (non-absolute selectivity) or can be a perfect bias characterized by a ligand stimulation of one receptor protein activity without any stimulation of another known receptor protein activity.

Another kind of ligands is known as allosteric regulators. "Allosteric regulators" or otherwise "allosteric modulators," "allosteric ligands" or "effector molecules," as used herein, refer to ligands that bind at an allosteric site (that is, a regulatory site physically distinct from the protein's active site) of a GPCR, in particular opioid receptor. In contrast to orthosteric ligands, allosteric modulators are non-competitive because they bind receptor proteins at a different site and modify their function even if the endogenous ligand also is binding. Allosteric regulators that enhance the protein's activity are referred to herein as "allosteric activators" or "positive allosteric modulators" (PAMs), whereas those that decrease the protein's activity are referred to herein as "allosteric inhibitors" or otherwise "negative allosteric modulators" (NAMs).

As used herein, the terms "determining," "measuring," "assessing," and "assaying" are used interchangeably and include both quantitative and qualitative determinations.

The term "antibody" is intended to mean an immunoglobulin or any fragment thereof that is capable of antigen binding. The term "antibody" also refers to single chain antibodies and antibodies with only one binding domain.

As used herein, the terms "complementarity-determining region" or "CDR" within the context of antibodies refer to variable regions of either H (heavy) or L (light) chains (also abbreviated as VH and VL, respectively) and contains the amino acid sequences capable of specifically binding to antigenic targets. These CDR regions account for the basic specificity of the antibody for a particular antigenic determinant structure. Such regions are also referred to as "hypervariable regions." The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all canonical antibodies each have three CDR regions, each non-contiguous with the others (termed L1, L2, L3, H1, H2, H3) for the respective light (L) and heavy (H) chains. Immunoglobulin single variable domains, in particular Nanobodies, generally comprise a single amino acid chain that can be considered to comprise four "framework sequences or regions" or FRs and three "complementarity-determining regions" or CDRs. The nanobodies have three CDR regions, each non-contiguous with the others (termed CDR1, CDR2, CDR3). The delineation of the FR and CDR sequences can, for example, be based on the IMGT unique numbering system for V-domains and V-like domains (Lefranc et al., 2003, Developmental and Comparative Immunology 27:55).

DETAILED DESCRIPTION

Binding Agents Against Opioid Receptors and Complexes Comprising the Same

A first aspect of the disclosure relates to a binding agent that is directed against and/or capable of specifically binding to a GPCR of the opioid receptor family (OR or OP receptors). According to a preferred embodiment, the invention relates to a conformation-selective binding agent that is directed against and/or capable of specifically binding to a GPCR of the opioid receptor family (OR or OP receptors).

As used herein, the "opioid receptor" refers to a receptor belonging to the superfamily of GPCRs (as defined herein), more particularly to the family A GPCRs, and include four types, designated μ (mu or MOP or Mor1), δ (delta or DOP), κ (kappa or KOP) opioid receptors, and finally NOP; see also Table 1. The amino acid sequences (and the nucleotide sequences of the cDNAs which encode them) of the opioid receptors are readily available, for example, by reference to GenBank (on the World Wide Web at ncbi.nlm.nih.gov/entrez). HGNC standardized nomenclature to human genes; accession numbers of different isoforms from different organisms are available from Uniprot (www.uniprot.org), see also Table 4. Moreover, a comprehensive overview of receptor nomenclature, pharmacological, functional and pathophysiological information on opioid receptors can be retrieved from the IUPHAR database (on the World Wide Web at iuphar-db.org/).

TABLE 1

Opioid receptor type classification

| Current recommended nomenclature | Presumed endogenous ligands |
|---|---|
| μ, mu, MOP, MOR1 | β-endorphin enkephalins |

TABLE 1-continued

Opioid receptor type classification

| Current recommended nomenclature | Presumed endogenous ligands |
|---|---|
| | endomorphin-1 |
| | endomorphin-2 |
| δ, delta, DOP | enkephalines |
| | β-endorphin |
| κ, kappa, KOP | dynorphin A |
| | dynorphin B |
| | α-neoendorphin |
| NOP | nociception/orphanin FQ |

According to a preferred embodiment, the binding agent of the disclosure is directed against and/or specifically binds to an opioid receptor. The nature of the opioid receptor is not critical to the invention and can be from any organism including a fungus (including yeast), nematode, virus, insect, plant, bird (e.g., chicken, turkey), reptile or mammal (e.g., a mouse, rat, rabbit, hamster, gerbil, dog, cat, goat, pig, cow, horse, whale, monkey, camelid, or human). Preferably, the opioid receptor is of mammalian origin, even more preferably of human origin.

In a specific embodiment, the binding agent of the disclosure is directed against and/or specifically binds to mu opioid receptor, such as the human mu opioid receptor (SEQ ID NO: 50). In another specific embodiment, the binding agent of the disclosure is directed against and/or specifically binds to delta opioid receptor, such as the human delta opioid receptor (SEQ ID NO: 54). In yet another specific embodiment, the binding agent of the disclosure is directed against and/or specifically binds to kappa opioid receptor, such as the human kappa opioid receptor (SEQ ID NO: 53). In yet another specific embodiment, the binding agent of the disclosure is directed against and/or specifically binds to nociceptin receptor, such as the human nociceptin receptor (SEQ ID NO: 55). Preferably, the binding agent of the disclosure is directed against and/or specifically binds to the mu opioid receptor, in particular, the human mu opioid receptor (SEQ ID NO: 50). According to a particular embodiment, the binding agent that is directed against and/or specifically binds to the human mu opioid receptor is cross-reactive with the delta opioid receptor and/or with the kappa opioid receptor and/or with the nociceptin receptor. According to another particular embodiment, the binding agent that is directed against and/or specifically binds to the human mu opioid receptor is not cross-reactive with the delta opioid receptor nor with the kappa opioid receptor nor with the nociceptin receptor.

A prerequisite of the binding agent is its capability to specifically bind (as defined herein) to the opioid receptor, particularly the mu opioid receptor. Thus, the binding agent may be directed against any conformational epitope (as defined herein) of the opioid receptor. A binding agent that specifically binds to a "conformational epitope" specifically binds to a tertiary (i.e., three-dimensional) structure of a folded protein, and binds at much reduced (i.e., by a factor of at least 2, 5, 10, 50 or 100) affinity to the linear (i.e., unfolded, denatured) form of the protein. In particular, the conformational epitope can be part of an intracellular or extracellular region, or an intramembraneous region, or a domain or loop structure of the opioid receptor. Thus, according to particular embodiments, the binding agent may be directed against an extracellular region, domain, loop or other extracellular conformational epitope of the opioid receptor, but is preferably directed against the extracellular parts of the transmembrane domains or more preferably against the extracellular loops that link the transmembrane domains. Alternatively, the binding agent may be directed against an intracellular region, domain, loop or other intracellular conformational epitope of the opioid receptor, but is preferably directed against the intracellular parts of the transmembrane domains or more preferably against the intracellular loops that link the transmembrane domains. In other specific embodiments, the binding agent may be directed against a conformational epitope that forms part of the binding site of a natural ligand, including but limited to an endogenous orthosteric agonist. In still other embodiments, the binding agent may be directed against a conformational epitope, in particular an intracellular epitope, that is comprised in a binding site for a downstream signaling protein, including but not-limited to a G protein binding site or a β-arrestin binding site.

In one specific embodiment, the binding agent directed against and/or specifically binding to an opioid receptor binds to an extracellular conformational epitope of the receptor. In a more specific embodiment, the binding agent directed against and/or specifically binding to an opioid receptor is capable of displacing an orthosteric ligand bound to the opioid receptor or prevents binding of an orthosteric ligand to the opioid receptor. According to preferred embodiments, the binding agent of the disclosure can specifically displace an orthosteric ligand on the opioid receptor, with an average displacement of ligand binding signal of at least 40%, at least 50%, at least 60%, at least 70%, at least 80% or more. Percentages of average displacement can be determined in several ways, e.g., by a ligand displacement assay known in the art (see also Example section). Orthosteric ligands of opioid receptors are described further herein, and are well-known in the art.

In another specific embodiment, the binding agent directed against and/or specifically binding to an opioid receptor binds to an intracellular conformational epitope of the receptor.

It will be understood that the binding agent preferably is capable of stabilizing the opioid receptor in a particular conformation. With the term "stabilizing," or grammatically equivalent terms, as defined hereinbefore, is meant an increased stability of an opioid receptor with respect to the structure (e.g., conformational state) and/or particular biological activity (e.g., intracellular signaling activity, ligand binding affinity, . . . ). In relation to increased stability with respect to structure and/or biological activity, this may be readily determined by either a functional assay for activity (e.g., $Ca^{2+}$ release, cAMP generation or transcriptional activity, β-arrestin recruitment, . . . ) or ligand binding or by means of physical methods such as X-ray crystallography, NMR, or spin labeling, among other methods. The term "stabilize" also includes increased thermostability of the receptor under non-physiological conditions induced by denaturants or denaturing conditions. The terms "thermostabilize," "thermostabilizing," and "increasing the thermostability of," as used herein, refer to the functional rather than to the thermodynamic properties of a receptor and to the protein's resistance to irreversible denaturation induced by thermal and/or chemical approaches including, but not limited to, heating, cooling, freezing, chemical denaturants, pH, detergents, salts, additives, proteases or temperature. Irreversible denaturation leads to the irreversible unfolding of the functional conformations of the protein, loss of biological activity and aggregation of the denaturated protein. In relation to an increased stability to heat, this can be readily determined by measuring ligand binding or by using spectroscopic methods such as fluorescence, CD or light scattering that are sensitive to unfolding at increasing temperatures. It is preferred that the binding agent is capable of increasing the stability as measured by an increase in the thermal stability of an opioid receptor in a functional conformational state with at least 2° C., at least 5° C., at least 8° C., and more preferably at least 10° C. or 15° C. or 20° C. In relation to an increased stability to a detergent or to a chaotrope, typically the opioid receptor is incubated for a defined time in the presence of a test detergent or a test chaotropic agent and the stability is determined using, for example, ligand binding or a spectroscoptic method, optionally at increasing temperatures as discussed above. Otherwise, the binding agent is capable of increasing the stability to extreme pH of a functional conformational state of an opioid receptor. In relation to an extreme of pH, a typical test pH would be chosen, for example, in the range 6 to 8, the range 5.5 to 8.5, the range 5 to 9, the range 4.5 to 9.5, more specifically in the range 4.5 to 5.5 (low pH) or in the range 8.5 to 9.5 (high pH). The terms "(thermo)stabilize," "(thermo)stabilizing," "increasing the (thermo)stability of," as used herein, apply to opioid receptors embedded in lipid particles or lipid layers (for example, lipid monolayers, lipid bilayers, and the like) and to opioid receptors that have been solubilized in detergent.

It is thus particularly envisaged that the binding agent hereof stabilizes a particular conformation of the opioid receptor upon binding of the binding agent. According to one specific embodiment, the opioid receptor is stabilized in an active conformation upon binding of a binding agent that is conformation-selective for an active conformation. The term "active conformation," as used herein, refers to a spectrum of receptor conformations that allows signal transduction towards an intracellular effector system, including G protein-dependent signaling and G protein-independent signaling (e.g., β-arrestin signaling). An "active conformation" thus encompasses a range of ligand-specific conformations, including an agonist conformation, a partial agonist conformation or a biased agonist conformation. Alternatively, the opioid receptor is stabilized in an inactive conformation upon binding of a binding agent that is conformation-selective for an inactive conformation. The term "inactive conformation," as used herein, refers to a spectrum of receptor conformations that does not allow or blocks signal transduction towards an intracellular effector system. An "inactive conformation" thus encompasses a range of ligand-specific conformations, including an inverse agonist conformation. It will be understood that the site of binding of the ligand is not critical for obtaining an active or inactive conformation. Hence, orthosteric ligands as well as allosteric modulators may equally be capable of stabilizing an opioid receptor in an active or inactive conformation. According to a particular embodiment of the disclosure, the binding agent that is capable of stabilizing the opioid receptor may bind at the orthosteric site or an allosteric site. In other specific embodiments, the binding agent that is capable of stabilizing the opioid receptor may be an agonist conformation-selective ligand, or a partial agonist conformation-selective ligand or a biased agonist conformation-selective ligand, or an inverse agonist conformation-selective ligand, either by binding at the orthosteric site or at an allosteric site.

In general, a binding agent that stabilizes an active conformation of an opioid receptor will increase or enhance the affinity of the receptor for an agonist, more particularly for a full agonist, a partial agonist or a biased agonist, as compared to the receptor in the absence of the binding agent (or in the presence of a mock binding agent). Also, a binding agent that stabilizes an active conformation of an opioid receptor will decrease the affinity of the receptor for an inverse agonist, as compared to the receptor in the absence of the binding agent (or in the presence of a mock binding agent). In contrast, a binding agent that stabilizes an inactive conformation of an opioid receptor will enhance the affinity of the receptor for an inverse agonist and will decrease the affinity of the receptor for an agonist, particularly for a full agonist, a partial agonist or a biased agonist, as compared to the receptor in the absence of the binding agent (or in the presence of a mock binding agent). An increase or decrease in affinity for a ligand may be measured by a decrease or increase, respectively, in $EC_{50}$, $IC_{50}$, $K_d$, $K_i$, or any other measure of affinity or potency known to one of skill in the art. It is particularly preferred that the binding agent that stabilizes a particular conformation of an opioid receptor is capable of increasing or decreasing the affinity for a conformation-selective ligand at least two-fold, at least five-fold, at least ten-fold, at least fifty-fold, and more preferably at least one hundred-fold, even more preferably at least one thousand-fold or more, upon binding to the receptor. It will be appreciated that affinity measurements for conformation-selective ligands that trigger/inhibit particular signaling pathways may be carried out with any type of ligand, including natural ligands, small molecules, as well as biologicals; with orthosteric ligands as well as allosteric modulators; with single compounds as well as compound libraries; with lead compounds or fragments; etc.

According to a particularly preferred embodiment, the binding agent of the disclosure that is directed against and/or specifically binding to an opioid receptor is a G protein mimetic. The term "G protein mimetic," as used herein, refers to a binding agent that, upon binding to an opioid receptor, enhances the affinity of the receptor for orthosteric or allosteric agonists, to a similar extend as upon binding of the natural G protein to the opioid receptor. Preferably, a binding agent that is a G protein mimetic will occupy the G protein binding site of an opioid receptor. It will be understood that the natural G protein of an opioid receptor is the Gi protein. In a preferred embodiment, the binding agent of the disclosure that is directed against and/or specifically binding to an opioid receptor is a Gi protein mimetic (also as illustrated in Example section).

It will also be understood that the opioid receptor to which the binding agents hereof will bind, can be a naturally occurring or non-naturally occurring (i.e., altered by man) receptor (as defined herein). In particular, wild-type polymorphic variants and isoforms of the opioid receptor, as well as orthologs across different species are examples of naturally occurring proteins, and are found, for example, and without limitation, in a mammal, more specifically in a human, or in a virus, or in a plant, or in an insect, amongst others). Such receptors are found in nature. For example, a "human mu opioid receptor" has an amino acid sequence that is at least 95% identical to (e.g., at least 95% or at least 98% identical to) the naturally occurring "human mu opioid receptor" of Genbank accession number NM_000914. Wild-type opioid receptors that have been mutated and variants of naturally occurring opioid receptors are examples of non-naturally occurring proteins. Non-limiting examples of non-naturally occurring opioid receptors include, without limitation, opioid receptors that have been made constitutively active through mutation, opioid receptors with a loop deletion, opioid receptors with an N- and/or C-terminal deletion, opioid receptors with a substitution, an insertion or addition, or any combination thereof, in relation to their amino acid or nucleotide sequence, or other variants of naturally occurring opioid receptors. Also comprised within the scope of the disclosure are target opioid receptors comprising a chimeric or hybrid structure, for example, a chimeric opioid receptor with an N- and/or C-terminus from one opioid receptor and loops of a second opioid receptor, or comprising an opioid receptor fused to a moiety, such as T4 lysozyme, Flavodoxin, Xylanase, Rubredoxin or cytochrome b as an utility in GPCR crystallization (Chun et al., 2012 and also described in patent applications WO2012/158555, WO2012/030735, WO2012/148586). According to specific embodiments within the scope of the disclosure, a non-naturally occurring opioid receptor may have an amino acid sequence that is at least 80% identical to, at least 90% identical to, at least 95% identical to or at least 99% identical to, a corresponding naturally occurring opioid receptor.

Thus, according to a preferred embodiment, the binding agent is capable of recognizing both a naturally occurring as well as a non-naturally occurring opioid receptor. This may be particularly advantageous in certain circumstances, and depending on the purpose or application. For example, and for illustration purposes only, to increase the probability of obtaining crystals of an opioid receptor stabilized in a particular conformation enabled by the binding agents of the disclosure, it might be desired to perform some protein engineering without or only minimally affecting the conformation (e.g., active conformation with increased affinity for agonists). Or, alternatively or additionally, to increase cellular expression levels of an opioid receptor, or to increase the stability, one might also consider introducing certain mutations in the receptor of interest.

The term "binding agent," as used herein, means the whole or part of a proteinaceous (protein, protein-like or protein containing) molecule that is capable of binding using specific intermolecular interactions to an opioid receptor. In particular, the term "binding agent" is not meant to include a naturally occurring binding partner of the opioid receptor, such as a G protein, an arrestin, an endogenous ligand; or variants or derivatives (including fragments) thereof. More specifically, the term "binding agent" refers to a polypeptide, more particularly a protein domain. A suitable protein domain is an element of overall protein structure that is self-stabilizing and that folds independently of the rest of the protein chain and is often referred to as "binding domain." Such binding domains vary in length from between about 25 amino acids up to 500 amino acids and more. Many binding domains can be classified into folds and are recognizable, identifiable, 3-D structures. Some folds are so common in many different proteins that they are given special names. Non-limiting examples are binding domains selected from a 3- or 4-helix bundle, an armadillo repeat domain, a leucine-rich repeat domain, a PDZ domain, a SUMO or SUMO-like domain, a cadherin domain, an immunoglobulin-like domain, phosphotyrosine-binding domain, pleckstrin homology domain, src homology 2 domain, amongst others. A binding domain can thus be derived from a naturally occurring molecule, e.g., from components of the innate or adaptive immune system, or it can be entirely artificially designed.

In general, a binding domain can be immunoglobulin-based or it can be based on domains present in proteins, including but not limited to microbial proteins, protease inhibitors, toxins, fibronectin, lipocalins, single chain antiparallel coiled coil proteins or repeat motif proteins. Particular examples of binding domains which are known in the art include, but are not limited to: antibodies, heavy chain antibodies (hcAb), single domain antibodies (sdAb), mini-bodies, the variable domain derived from camelid heavy chain antibodies (VHH or nanobodies), the variable domain of the new antigen receptors derived from shark antibodies (VNAR), alphabodies, protein A, protein G, designed ankyrin-repeat domains (DARPins), fibronectin type III repeats, anticalins, knottins, engineered CH2 domains (nanoantibodies), engineered SH3 domains, affibodies, peptides and proteins, lipopeptides (e.g., pepducins) (see, e.g., Gebauer & Skerra, 2009; Skerra, 2000; Starovasnik et al., 1997; Binz et al., 2004; Koide et al., 1998; Dimitrov, 2009; Nygren et al., 2008; WO2010066740). Frequently, when generating a particular type of binding domain using selection methods, combinatorial libraries comprising a consensus or framework sequence containing randomized potential interaction residues are used to screen for binding to a molecule of interest, such as a protein.

According to a preferred embodiment, it is particularly envisaged that the binding agent hereof is derived from an innate or adaptive immune system. Preferably, the binding agent is derived from an immunoglobulin. Preferably, the binding agent according to the invention is derived from an antibody or an antibody fragment. The term "antibody" (Ab) refers generally to a polypeptide encoded by an immunoglobulin gene, or a functional fragment thereof, that specifically binds and recognizes an antigen, and is known to the person skilled in the art. An antibody is meant to include a conventional four-chain immunoglobulin, comprising two identical pairs of polypeptide chains, each pair having one "light" (about 25 kDa) and one "heavy" chain (about 50 kDa). Typically, in conventional immunoglobulins, a heavy chain variable domain (VH) and a light chain variable domain (VL) interact to form an antigen binding site. The term "antibody" is meant to include whole antibodies, including single-chain whole antibodies, and antigen-binding fragments. In some embodiments, antigen-binding fragments may be antigen-binding antibody fragments that include, but are not limited to, Fab, Fab' and F(ab')2, Fd, single-chain Fvs (scFv), single-chain antibodies, disulfide-linked Fvs (dsFv) and fragments comprising or consisting of either a VL or VH domain, and any combination of those or any other functional portion of an immunoglobulin peptide capable of binding to the target antigen. The term "antibodies" is also meant to include heavy chain antibodies, or fragments thereof, including immunoglobulin single variable domains, as defined further herein.

The term "immunoglobulin single variable domain" defines molecules wherein the antigen binding site is present on, and formed by, a single immunoglobulin domain (which is different from conventional immunoglobulins or their fragments, wherein typically two immunoglobulin variable domains interact to form an antigen binding site). It should however be clear that the term "immunoglobulin single variable domain" does comprise fragments of conventional immunoglobulins wherein the antigen binding site is formed by a single variable domain. Preferably, the binding agent within the scope of the disclosure is an immunoglobulin single variable domain.

Generally, an immunoglobulin single variable domain will be an amino acid sequence comprising four framework regions (FR1 to FR4) and three complementarity-determining regions (CDR1 to CDR3), preferably according to the following formula (1):

FR1-CDR1-FR2-CDR2-FR3-CDR3-FR4    (1)

or any suitable fragment thereof (which will then usually contain at least some of the amino acid residues that form at least one of the complementarity-determining regions).

Immunoglobulin single variable domains comprising four FRs and three CDRs are known to the person skilled in the art and have been described, as a non-limiting example, in Wesolowski et al., 2009. Typical, but non-limiting, examples of immunoglobulin single variable domains include light chain variable domain sequences (e.g., a VL domain sequence) or a suitable fragment thereof, or heavy chain variable domain sequences (e.g., a VH domain sequence or VHH domain sequence) or a suitable fragment thereof, as long as it is capable of forming a single antigen binding unit. Thus, according to a preferred embodiment, the binding agent is an immunoglobulin single variable domain that is a light chain variable domain sequence (e.g., a VL domain sequence) or a heavy chain variable domain sequence (e.g., a VH domain sequence); more specifically, the immunoglobulin single variable domain is a heavy chain variable domain sequence that is derived from a conventional four-chain antibody or a heavy chain variable domain sequence that is derived from a heavy chain antibody. The immunoglobulin single variable domain may be a domain antibody, or a single domain antibody, or a "dAB" or dAb, or a Nanobody (as defined herein), or another immunoglobulin single variable domain, or any suitable fragment of any one thereof. For a general description of single domain antibodies, reference is made to the following book: "Single domain antibodies," Methods in Molecular Biology, Eds. Saerens and Muyldermans, 2012, Vol. 911. The immunoglobulin single variable domains, generally comprise a single amino acid chain that can be considered to comprise four "framework sequences" or FRs and three "complementarity-determining regions" or CDRs (as defined hereinbefore). It should be clear that framework regions of immunoglobulin single variable domains may also contribute to the binding of their antigens (Desmyter et al., 2002; Korotkov et al., 2009). The delineation of the CDR sequences (and thus also the FR sequences) can be based on the IMGT unique numbering system for V-domains and V-like domains (Lefranc et al., 2003). Alternatively, the delineation of the FR and CDR sequences can be done by using the Kabat numbering system as applied to VHH domains from Camelids in the article of Riechmann and Muyldermans (2000).

It should be noted that the immunoglobulin single variable domains as binding agent in their broadest sense are not limited to a specific biological source or to a specific method of preparation. The term "immunoglobulin single variable domain" encompasses variable domains of different origin, comprising mouse, rat, rabbit, donkey, human, shark, camelid variable domains. According to specific embodiments, the immunoglobulin single variable domains are derived from shark antibodies (the so-called immunoglobulin new antigen receptors or IgNARs), more specifically from naturally occurring heavy chain shark antibodies, devoid of light chains, and are known as VNAR domain sequences. Preferably, the immunoglobulin single variable domains are derived from camelid antibodies. More preferably, the immunoglobulin single variable domains are derived from naturally occurring heavy chain camelid antibodies, devoid of light chains, and are known as VHH domain sequences or Nanobodies.

According to a particularly preferred embodiment, the binding agent hereof is an immunoglobulin single variable domain that is a Nanobody (as defined further herein, and including, but not limited to, a VHH). The term "Nanobody" (Nb), as used herein, is a single domain antigen binding fragment. It particularly refers to a single variable domain derived from naturally occurring heavy chain antibodies and is known to the person skilled in the art. Nanobodies are usually derived from heavy chain only antibodies (devoid of light chains) seen in camelids (Hamers-Casterman et al., 1993; Desmyter et al., 1996) and consequently are often referred to as VHH antibody or VHH sequence. Camelids comprise old world camelids (*Camelus bactrianus* and *Camelus dromedarius*) and new world camelids (for example, *Lama paccos, Lama glama, Lama guanicoe* and *Lama vicugna*). NANOBODY® and NANOBODIES® are registered trademarks of Ablynx N V (Belgium). For a further description of VHHs or Nanobodies, reference is made to the book "Single domain antibodies," Methods in Molecular Biology, Eds. Saerens and Muyldermans, 2012, Vol. 911, in particular, to the Chapter by Vincke and Muyldermans (2012), as well as to a non-limiting list of patent applications, which are mentioned as general background art, and include: WO 94/04678, WO 95/04079, WO 96/34103 of the Vrije Universiteit Brussel; WO 94/25591, WO 99/37681, WO 00/40968, WO 00/43507, WO 00/65057, WO 01/40310, WO 01/44301, EP 1 134 231 and WO 02/48193 of Unilever; WO 97/49805, WO 01/21817, WO 03/035694, WO 03/054016 and WO 03/055527 of the Vlaams Instituut voor Biotechnologie (VIB); WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N. V. and the further published patent applications by Ablynx N. V. As will be known by the person skilled in the art, the Nanobodies are particularly characterized by the presence of one or more Camelidae "hallmark residues" in one or more of the framework sequences (according to Kabat numbering), as described, for example, in WO 08/020079, on page 75, Table A-3, incorporated herein by reference). It should be noted that the "Nanobodies" in their broadest sense are not limited to a specific biological source or to a specific method of preparation. For example, Nanobodies® can generally be obtained: (1) by isolating the VHH domain of a naturally occurring heavy chain antibody; (2) by expression of a nucleotide sequence encoding a naturally occurring VHH domain; (3) by "humanization" of a naturally occurring VHH domain or by expression of a nucleic acid encoding a such humanized VHH domain; (4) by "camelization" of a naturally occurring VH domain from any animal species, and in particular from a mammalian species, such as from a human being, or by expression of a nucleic acid encoding such a camelized VH domain; (5) by "camelization" of a "domain antibody" or "Dab" as described in the art, or by expression of a nucleic acid encoding such a camelized VH domain; (6) by using synthetic or semi-synthetic techniques for preparing proteins, polypeptides or other amino acid sequences known per se; (7) by preparing a nucleic acid encoding a Nanobody using techniques for nucleic acid synthesis known per se, followed by expression of the nucleic acid thus obtained; and/or (8) by any combination of one or more of the foregoing. A further description of Nanobodies, including humanization and/or camelization of Nanobodies, can be found, e.g., in WO 08/101985 and WO 08/142164, as well as further herein. A particular class of Nanobodies binding conformational epitopes of native targets is called Xaperones and is particularly envisaged here. Xaperone™ is a trademark of VIB and VUB (Belgium). A Xaperone™ is a camelid single domain antibody that constrains a drug target into a unique, conformation.

Within the scope of the disclosure, the term "immunoglobulin single variable domain" also encompasses variable domains that are "humanized" or "camelized," in particular, Nanobodies that are "humanized" or "camelized." For example, both "humanization" and "camelization" can be performed by providing a nucleotide sequence that encodes a naturally occurring VHH domain or VH domain, respectively, and then changing, in a manner known per se, one or more codons in the nucleotide sequence in such a way that the new nucleotide sequence encodes a "humanized" or "camelized" immunoglobulin single variable domains hereof, respectively. This nucleic acid can then be expressed in a manner known per se, so as to provide the desired immunoglobulin single variable domains hereof. Alternatively, based on the amino acid sequence of a naturally occurring VHH domain or VH domain, respectively, the amino acid sequence of the desired humanized or camelized immunoglobulin single variable domains hereof, respectively, can be designed and then synthesized de novo using techniques for peptide synthesis known per se. Also, based on the amino acid sequence or nucleotide sequence of a naturally occurring VHH domain or VH domain, respectively, a nucleotide sequence encoding the desired humanized or camelized immunoglobulin single variable domains hereof, respectively, can be designed and then synthesized de novo using techniques for nucleic acid synthesis known per se, after which the nucleic acid thus obtained can be expressed in a manner known per se, so as to provide the desired immunoglobulin single variable domains hereof. Other suitable methods and techniques for obtaining the immunoglobulin single variable domains hereof and/or nucleic acids encoding the same, starting from naturally occurring VH sequences or preferably VHH sequences, will be clear from the skilled person, and may, for example, comprise combining one or more parts of one or more naturally occurring VH sequences (such as one or more FR sequences and/or CDR sequences), one or more parts of one or more naturally occurring VHH sequences (such as one or more FR sequences or CDR sequences), and/or one or more synthetic or semi-synthetic sequences, in a suitable manner, so as to provide a Nanobody hereof or a nucleotide sequence or nucleic acid encoding the same.

According to further specific embodiments, the disclosure encompasses conformational-selective binding agents, in particular conformational-selective immunoglobulin single variable domains, targeting the mu opioid receptor, comprising an amino acid sequence that comprises four framework regions (FR1 to FR4) and three complementarity-determining regions (CDR1 to CDR3), according to the following formula (1):

FR1-CDR1-FR2-CDR2-FR3-CDR3-FR4 (1)

and wherein CDR1 is chosen from the group consisting of:
a) SEQ ID NOs: 13-18, 76
b) A polypeptide that has at least 80% amino acid identity with SEQ ID NOs: 13-18, 76
c) A polypeptide that has 3, 2 or 1 amino acid difference with SEQ ID NOs: 13-18, 76
and wherein CDR2 is chosen from the group consisting of:
a) SEQ ID NOs: 25-30, 78
b) A polypeptide that has at least 80% amino acid identity with SEQ ID NOs: 25-30, 78
c) A polypeptide that has 3, 2 or 1 amino acid difference with SEQ ID NOs: 25-30, 78
and wherein CDR3 is chosen from the group consisting of:
a) SEQ ID NOs: 37-42, 80
b) A polypeptide that has at least 80% amino acid identity with SEQ ID NOs: 37-42, 80
c) A polypeptide that has 3, 2 or 1 amino acid difference with SEQ ID NOs: 37-42, 80.

In a particular embodiment of the disclosure, the immunoglobulin single variable domain directed against and/or specifically binding to the mu opioid receptor is a Nanobody or VHH, wherein the Nanobody has an amino acid sequence selected from the group consisting of SEQ ID NOs: 1-6, 74 or variants thereof. In a particularly preferred embodiment, the disclosure provides for an immunoglobulin single variable domain comprising an amino acid sequence that comprises four framework regions (FR1 to FR4) and three complementarity-determining regions (CDR1 to CDR3), according to the following formula (1):

FR1-CDR1-FR2-CDR2-FR3-CDR3-FR4 (1);

wherein CDR1 is SEQ ID NO: 13, and CDR2 is SEQ ID NO: 25, and CDR3 is SEQ ID NO: 37; or wherein CDR1 is SEQ ID NO: 14, and CDR2 is SEQ ID NO: 26, and CDR3 is SEQ ID NO: 38; or wherein CDR1 is SEQ ID NO: 15, and CDR2 is SEQ ID NO: 27, and CDR3 is SEQ ID NO: 39; or wherein CDR1 is SEQ ID NO: 16, and CDR2 is SEQ ID NO: 28, and CDR3 is SEQ ID NO: 40; or wherein CDR1 is SEQ ID NO: 17, and CDR2 is SEQ ID NO: 29, and CDR3 is SEQ ID NO: 41; or wherein CDR1 is SEQ ID NO: 18, and CDR2 is SEQ ID NO: 30, and CDR3 is SEQ ID NO: 42.

More preferably, the binding agents, in particular immunoglobulin single variable domains, directed against and/or specifically binding to mu opioid receptor has an amino acid sequence chosen from the group consisting of SEQ ID NOs: 1-6, 74. In one particular embodiment, the binding agents of the disclosure are defined by SEQ ID NOs: 1-6, 74.

In particular, non-limiting examples of binding agents directed against and/or specifically binding to mu opioid receptor, which are specifically characterized as G protein mimetics (as defined hereinbefore), are immunoglobulin single variable domains that have an amino acid sequence chosen from the group consisting of SEQ ID NOs: 1-4. Non-limiting examples of binding agents directed against and/or specifically binding to mu opioid receptor, that are specifically characterized as binding to an extracellular conformational epitope are immunoglobulin single variable domains that have an amino acid sequence chosen from the group consisting of SEQ ID NO: 5. Non-limiting examples of binding agents directed against and/or specifically binding to mu opioid receptor, that are specifically characterized as binding to an intracellular conformational epitope, are immunoglobulin single variable domains that have an amino acid sequence chosen from the group consisting of SEQ ID NOs: 6, 74.

Also within the scope of the disclosure are natural or synthetic analogs, mutants, variants, alleles, parts or fragments (herein collectively referred to as "variants") of the immunoglobulin single variable domains, in particular the nanobodies, as defined herein, and in particular variants of the immunoglobulin single variable domains of SEQ ID NOs: 1-6 (see Tables 2-3). Thus, according to one embodiment, the term "immunoglobulin single variable domain hereof" or "Nanobody hereof" in its broadest sense also covers such variants. Generally, in such variants, one or more amino acid residues may have been replaced, deleted and/or added, compared to the immunoglobulin single variable domains hereof, as defined herein. Such substitutions, insertions or deletions may be made in one or more of the FRs and/or in one or more of the CDRs and, in particular, variants of the FRs and CDRs of the immunoglobulin single variable domains of SEQ ID NOs: 1-6, 74 (see Tables 2-3). Variants, as used herein, are sequences wherein each or any framework region and each or any complementarity-determining region shows at least 80% identity, preferably at least 85% identity, more preferably 90% identity, even more preferably 95% identity or, still even more preferably 99% identity with the corresponding region in the reference sequence (i.e., FR1_variant versus FR1_reference, CDR1_variant versus CDR1_reference, FR2_variant versus FR2_reference, CDR2_variant versus CDR2_reference, FR3_variant versus FR3_reference, CDR3_variant versus CDR3_reference, FR4_variant versus FR4_reference), as can be measured electronically by making use of algorithms such as PILEUP and BLAST. Software for performing BLAST analyses is publicly available through the National Center for Biotechnology Information (on the World Wide Web at ncbi.nlm.nih.gov/). It will be understood that for determining the degree of amino acid identity of the amino acid sequences of the CDRs of one or more sequences of the immunoglobulin single variable domains, the amino acid residues that form the framework regions are disregarded. Similarly, for determining the degree of amino acid identity of the amino acid sequences of the FRs of one or more sequences of the immunoglobulin single variable domains hereof, the amino acid residues that form the complementarity regions are disregarded. Such variants of immunoglobulin single variable domains may be of particular advantage since they may have improved potency/affinity.

By means of non-limiting examples, a substitution may, for example, be a conservative substitution (as described herein) and/or an amino acid residue may be replaced by another amino acid residue that naturally occurs at the same position in another VHH domain. Thus, any one or more substitutions, deletions or insertions, or any combination thereof, that either improve the properties of the immunoglobulin single variable domains or that do not detract from the desired properties or from the balance or combination of desired properties of the immunoglobulin single variable domain (i.e., to the extent that the immunoglobulin single variable domains is no longer suited for its intended use) are included within the scope of the disclosure. A skilled person will generally be able to determine and select suitable substitutions, deletions or insertions, or suitable combinations of thereof, based on the invention herein and optionally after a limited degree of routine experimentation, which may, for example, involve introducing a limited number of possible substitutions and determining their influence on the properties of the immunoglobulin single variable domains thus obtained.

Also encompassed within the scope of the disclosure are immunoglobulin single variable domains that are in a "multivalent" form and are formed by bonding, chemically or by recombinant DNA techniques, together two or more monovalent immunoglobulin single variable domains. Non-limiting examples of multivalent constructs include "bivalent" constructs, "trivalent" constructs, "tetravalent" constructs, and so on. The immunoglobulin single variable domains comprised within a multivalent construct may be identical or different. In another particular embodiment, the immunoglobulin single variable domains hereof are in a "multispecific" form and are formed by bonding together two or more immunoglobulin single variable domains, of which at least one with a different specificity. Non-limiting examples of multi-specific constructs include "bi-specific" constructs, "tri-specific" constructs, "tetra-specific" constructs, and so on. To illustrate this further, any multivalent or multispecific (as defined herein) immunoglobulin single variable domain hereof may be suitably directed against two or more different epitopes on the same antigen, for example, against two or more different epitopes of the opioid receptor; or may be directed against two or more different antigens, for example, against an epitope of opioid receptor and an epitope of a natural binding partner of the opioid receptor (e.g., G protein, β-arrestin). In particular, a monovalent immunoglobulin single variable domain hereof is such that it will bind to the target receptor with an affinity less than 500 nM, preferably less than 200 nM, more preferably less than 10 nM, such as less than 500 pM. Multivalent or multispecific immunoglobulin single variable domains hereof may also have (or be engineered and/or selected for) increased avidity and/or improved selectivity for the desired receptor, and/or for any other desired property or combination of desired properties that may be obtained by the use of such multivalent or multispecific immunoglobulin single variable domains. In a particular embodiment, such multivalent or multispecific binding domains hereof may also have (or be engineered and/or selected for) improved efficacy in modulating signaling activity of a GPCR (see also further herein).

Further, and depending on the host organism used to express the binding agent hereof, deletions and/or substitutions within the binding agent may be designed in such a way that, e.g., one or more sites for post-translational modification (such as one or more glycosylation sites) are removed, as will be within the ability of the person skilled in the art. Alternatively, substitutions or insertions may be designed so as to introduce one or more sites for attachment of functional groups (as described further herein).

It is also expected that the binding agent will generally be capable of binding to all naturally occurring or synthetic analogs, variants, mutants, alleles, parts, fragments, and isoforms of an opioid receptor; or at least to those analogs, variants, mutants, alleles, parts, fragments, and isoforms of an opioid receptor that contain one or more antigenic determinants or epitopes that are essentially the same as the antigenic determinant(s) or epitope(s) to which the binding agents hereof bind to an opioid receptor.

In another aspect, the disclosure also provides a complex comprising an opioid receptor (as described hereinbefore), and a binding agent (as described hereinbefore) that is directed against and/or specifically binds to the opioid receptor. As a non-limiting example, a stable complex may be purified by size exclusion chromatography. According to one embodiment, the complex as described above further comprises at least one other receptor ligand, preferably a conformation-selective ligand (as defined herein). Non-limiting examples of ligands include full agonists, partial agonists, antagonists, inverse agonists, natural binding partners, allosteric modulators, and the like. To illustrate this further, without the purpose of being limitative, agonists of mu opioid receptor are known in the art and include sufentanil, fentanyl, etonitazene, DAMGO, PL017, (−)-methadone, morphine, amongst others. Antagonists of mu opioid receptor are known in the art and include naltrexone, nalmefene, diprenorphine, CTAP, amongst others. Also, without the purpose of being limitative, agonists of kappa opioid receptor are known in the art and include (−)-bremazocine, (−)-cyclazocine, etorphine, amongst others. Antagonists of kappa opioid receptor are known in the art and include naltrindole, naltrexone, nor-binaltorphimine amongst others. Also, agonists of delta opioid receptor are known in the art and include diprenorphine, nalmefene, nalorphine, morphine, amongst others. Antagonists of delta opioid receptor are known in the art and include naltrindole, naltrexone, naloxone, amongst others. Also, without the purpose of being limitative, agonists of NOP receptor are known in the art and include Ro64-6198, Ac-RYYRWK-NH2, UFP-112, amongst others. Antagonists of NOP receptor are known in the art and include SB 612111, peptide III-BTD, amongst others. Further examples can be found in the IUPHAR database (on the World Wide Web at iuphar-db.org/). Presumed endogenous ligands are listed in Table 1 (see above).

In a preferred embodiment, the binding agent and/or the complex, according to the invention, is in a solubilized form, such as in a detergent. In an alternative preferred embodiment, the binding agent and/or the complex, according to the invention, is immobilized to a solid support. Non-limiting examples of solid supports as well as methods and techniques for immobilization are described further in the detailed description. In still another embodiment, the binding agent and/or complex, according to the invention, is in a cellular composition, including an organism, a tissue, a cell, a cell line, or in a membrane composition or liposomal composition derived from the organism, tissue, cell or cell line. Examples of membrane or liposomal compositions include, but are not limited to, organelles, membrane preparations, viruses, Virus-Like Lipoparticles, and the like. It will be appreciated that a cellular composition, or a membrane-like or liposomal composition may comprise natural or synthetic lipids. In yet another preferred embodiment, the complex is crystalline. So, a crystal of the complex is also provided, as well as methods of making the crystal, which are described in greater detail below. Preferably, a crystalline form of a complex according to the invention and a receptor ligand is envisaged.

Screening and Selection of Binding Agents Against Opioid Receptors

Binding agents, in particular immunoglobulin single variable domains, can be identified in several ways, and will be illustrated hereafter in a non-limiting way for VHHs. Although naive or synthetic libraries of VHHs (for examples of such libraries, see WO9937681, WO0043507, WO0190190, WO03025020 and WO03035694) may contain binders against an opioid receptor in a functional conformation, a preferred embodiment of this invention includes the immunization of a Camelidae with an opioid receptor in a functional conformation, optionally bound to a receptor ligand, to expose the immune system of the animal with the conformational epitopes that are unique to the receptor in that particular conformation (for example, agonist-bound opioid receptor so as to raise antibodies directed against the receptor in its active conformational state). Optionally, a particular ligand can be coupled to the receptor of interest by chemical cross-linking. Thus, as further described herein, such VHH sequences can preferably be generated or obtained by suitably immunizing a species of Camelid with an opioid receptor, preferably a receptor in a functional conformational state (i.e., so as to raise a immune response and/or heavy chain antibodies directed against the receptor), by obtaining a suitable biological sample from the Camelid (such as a blood sample, or any sample of B-cells), and by generating VHH sequences directed against the receptor, starting from the sample. Such techniques will be clear to the skilled person. Yet another technique for obtaining the desired VHH sequences involves suitably immunizing a transgenic mammal that is capable of expressing heavy chain antibodies (i.e., so as to raise an immune response and/or heavy chain antibodies directed against an opioid receptor in a functional conformational state), obtaining a suitable biological sample from the transgenic mammal (such as a blood sample, or any sample of B-cells), and then generating VHH sequences directed against the receptor starting from the sample, using any suitable technique known per se. For example, for this purpose, the heavy chain antibody-expressing mice and the further methods and techniques described in WO 02085945 and in WO 04049794 can be used.

For the immunization of an animal with an opioid receptor, the receptor may be produced and purified using conventional methods that may employ expressing a recombinant form of the protein in a host cell, and purifying the protein using affinity chromatography and/or antibody-based methods. In particular embodiments, the baculovirus/Sf-9 system may be employed for expression, although other expression systems (e.g., bacterial, yeast or mammalian cell systems) may also be used. Exemplary methods for expressing and purifying GPCRs like the opioid receptor are described in, for example, Kobilka (1995), Eroglu et al. (2002), Chelikani et al. (2006) and the book "Identification and Expression of G Protein-Coupled Receptors" (Kevin R. Lynch (Ed.), 1998), among many others. A GPCR such as an opioid receptor may also be reconstituted in phospholipid vesicles. Likewise, methods for reconstituting an active GPCR in phospholipid vesicles are known, and are described in: Luca et al. (2003), Mansoor et al. (2006), Niu et al. (2005), Shimada et al. (2002), and Eroglu et al. (2003), among others. In certain cases, the GPCR and phospholipids may be reconstituted in phospholipids at high density (e.g., 1 mg receptor per mg of phospholipid). In particular embodiments, the phospholipids vesicles may be tested to confirm that the GPCR is active. In many cases, a GPCR may be present in the phospholipid vesicle in both orientations (in the normal orientation, and in the "upside down" orientation in which the intracellular loops are on the outside of the vesicle). Other immunization methods include, without limitation, the use of complete cells expressing an opioid receptor or fractions thereof, vaccination with a nucleic acid sequence encoding an opioid receptor (e.g., DNA vaccination), immunization with viruses or virus like particles expressing an opioid receptor, amongst others (e.g., as described in WO 2010070145, WO 2011083141).

Any suitable animal, in particular a mammal such as a rabbit, mouse, rat, camel, sheep, cow, shark, pig, amongst others, or a bird such as a chicken or turkey, may be immunized using any of the techniques well known in the art suitable for generating an immune response.

The selection for VHHs or Nanobodies, as a non-limiting example, specifically binding to a conformational epitope of a functional conformational state of an opioid receptor may, for example, be performed by screening a set, collection or library of cells that express heavy chain antibodies on their surface (e.g., B-cells obtained from a suitably immunized Camelid), or bacteriophages that display a fusion of genIII and Nanobody at their surface, or yeast cells that display a fusion of the mating factor protein Aga2p, by screening of a (naïve or immune) library of VHH sequences or Nanobody sequences, or by screening of a (naïve or immune) library of nucleic acid sequences that encode VHH sequences or Nanobody sequences, which may all be performed in a manner known per se, and which method may optionally further comprise one or more other suitable steps, such as, for example, and without limitation, a step of affinity maturation, a step of expressing the desired amino acid sequence, a step of screening for binding and/or for activity against the desired antigen (in this case, the opioid receptor in a particular conformation), a step of determining the desired amino acid sequence or nucleotide sequence, a step of introducing one or more humanizing substitutions, a step of formatting in a suitable multivalent and/or multispecific format, a step of screening for the desired biological and/or physiological properties (i.e., using a suitable assay known in the art), and/or any combination of one or more of such steps, in any suitable order.

Various methods may be used to determine specific binding (as defined hereinbefore) between the binding agent and a target opioid receptor, including, for example, enzyme linked immunosorbent assays (ELISA), flow cytometry, radioligand binding assays, surface plasmon resonance assays, phage display, and the like, which are common practice in the art, for example, in discussed in Sambrook et al. (2001), Molecular Cloning, A Laboratory Manual. Third Edition. Cold Spring Harbor Laboratory Press, Cold Spring Harbor, N.Y., and are further illustrated in the Example section. It will be appreciated that for this purpose often a unique label or tag will be used, such as a peptide label, a nucleic acid label, a chemical label, a fluorescent label, or a radio frequency tag, as described further herein.

A particularly preferred way of selecting for binding agents is as described in, for example, WO 2012/007593. In an alternative preferred embodiment, selection for conformation-selective binding agents can also be performed by using cell sorting to select, from a population of cells comprising a library of cell-surface tethered extracellular binding agents, cells that are specifically bound to either the opioid receptor in its active conformation or the opioid receptor in its inactive conformation, but not both. Without the purpose of being limitative, selection for (conformation-selective) binding agents is also further illustrated in the Example section.

Modifications of Binding Agents

The binding agents hereof may be further modified and/or may comprise (or can be fused to) other moieties, as described further herein. Examples of modifications, as well as examples of amino acid residues within the binding agent hereof that can be modified (i.e., either on the protein backbone but preferably on a side chain), methods and techniques that can be used to introduce such modifications and the potential uses and advantages of such modifications will be clear to the skilled person. For example, such a modification may involve the introduction (e.g., by covalent linking or in another suitable manner) of one or more functional groups, residues or moieties into or onto the binding agent. Examples of such functional groups and of techniques for introducing them will be clear to the skilled person, and can generally comprise all functional groups and techniques mentioned in the art as well as the functional groups and techniques known per se for the modification of pharmaceutical proteins, and in particular for the modification of antibodies or antibody fragments (including ScFvs and single domain antibodies), for which reference is, for example, made to Remington's Pharmaceutical Sciences, 16th ed., Mack Publishing Co., Easton, Pa. (1980). Such functional groups may, for example, be linked directly (for example, covalently) to the binding agent, or optionally via a suitable linker or spacer, as will again be clear to the skilled person.

One of the most widely used techniques for increasing the half-life and/or reducing immunogenicity of pharmaceutical proteins comprises attachment of a suitable pharmacologically acceptable polymer, such as poly(ethyleneglycol) (PEG) or derivatives thereof (such as methoxypoly(ethyleneglycol) or mPEG). Generally, any suitable form of pegylation can be used, such as the pegylation used in the art for antibodies and antibody fragments (including, but not limited to, (single) domain antibodies and ScFvs); reference is made to, for example, Chapman, Nat. Biotechnol., 54, 531-545 (2002); by Veronese and Harris, Adv. Drug Deliv. Rev. 54, 453-456 (2003), by Harris and Chess, Nat. Rev. Drug. Discov., 2, (2003) and in WO 04060965. Various reagents for pegylation of proteins are also commercially available, for example, from Nektar Therapeutics, USA. Preferably, site-directed pegylation is used, in particular via a cysteine-residue (see, for example, Yang et al., Protein Engineering, 16, 10, 761-770 (2003). For example, for this purpose, PEG may be attached to a cysteine residue that naturally occurs in an binding agent, or the binding agent may be modified so as to suitably introduce one or more cysteine residues for attachment of PEG, or an amino acid sequence comprising one or more cysteine residues for attachment of PEG may be fused to the N- and/or C-terminus of an binding agent, all using techniques of protein engineering known per se to the skilled person. Preferably, for the binding agents hereof, a PEG is used with a molecular weight of more than 5000, such as more than 10,000 and less than 200,000, such as less than 100,000; for example, in the range of 20,000-80,000. Another, usually less preferred modification comprises N-linked or O-linked glycosylation, usually as part of co-translational and/or post-translational modification, depending on the host cell used for expressing the immunoglobulin single variable domain or polypeptide hereof. Another technique for increasing the half-life of a binding agent may comprise the engineering into bifunctional constructs (for example, one Nanobody against the target opioid receptor and one against a serum protein such as albumin) or into fusions of binding agents with peptides (for example, a peptide against a serum protein such as albumin).

A usually less preferred modification comprises N-linked or O-linked glycosylation, usually as part of co-translational and/or post-translational modification, depending on the host cell used for expressing the binding agent hereof Yet another modification may comprise the introduction of one or more detectable labels or other signal-generating groups or moieties, depending on the intended use of the labeled binding agent. Suitable labels and techniques for attaching, using and detecting them will be clear to the skilled person, and, for example, include, but are not limited to, fluorescent labels, (such as IRDye800, VivoTag800, fluorescein, isothiocyanate, rhodamine, phycoerythrin, phycocyanin, allophycocyanin, o-phthaldehyde, and fluorescamine and fluorescent metals such as Eu or others metals from the lanthanide series), phosphorescent labels, chemiluminescent labels or bioluminescent labels (such as luminal, isoluminol, theromatic acridinium ester, imidazole, acridinium salts, oxalate ester, dioxetane or GFP and its analogs), radio-isotopes, metals, metals chelates or metallic cations or other metals or metallic cations that are particularly suited for use in in vivo, in vitro or in situ diagnosis and imaging, as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase). Other suitable labels will be clear to the skilled person and, for example, include moieties that can be detected using NMR or ESR spectroscopy. Such labeled binding agents hereof may, for example, be used for in vitro, in vivo or in situ assays (including immunoassays known per se, such as ELISA, RIA, EIA and other "sandwich assays," etc.) as well as in vivo diagnostic and imaging purposes, depending on the choice of the specific label. As will be clear to the skilled person, another modification may involve the introduction of a chelating group, for example, to chelate one of the metals or metallic cations referred to above. Suitable chelating groups, for example, include, without limitation, 2,2',2''-(10-(2-((2,5-dioxopyrrolidin-1-yl)oxy)-2-oxoethyl)-1,4,7,10-tetraazacyclododecane-1,4,7-triyl)triacetic acid (DOTA), 2,2'-(7-(2-((2,5-dioxopyrrolidin-1-yl)oxy)-2-oxoethyl)-1,4,7-triazonane-1,4-diyl)diacetic acid (NOTA), diethyl-enetriaminepentaacetic acid (DTPA) or ethylenediaminetetraacetic acid (EDTA). Yet another modification may comprise the introduction of a functional group that is one part of a specific binding pair, such as the biotin-(strept)avidin binding pair. Such a functional group may be used to link the binding agent to another protein, polypeptide or chemical compound that is bound to the other half of the binding pair, i.e., through formation of the binding pair. For example, a binding agent hereof may be conjugated to biotin, and linked to another protein, polypeptide, compound or carrier conjugated to avidin or streptavidin. For example, such a conjugated binding agent may be used as a reporter, for example, in a diagnostic system where a detectable signal-producing agent is conjugated to avidin or streptavidin. Such binding pairs may, for example, also be used to bind the binding agent hereof to a carrier, including carriers suitable for pharmaceutical purposes. One non-limiting example is the liposomal formulations described by Cao and Suresh, Journal of Drug Targetting, 8, 4, 257 (2000). Such binding pairs may also be used to link a therapeutically active agent to the binding agent hereof.

In case binding agents are modified by linking particular functional groups, residues or moieties (as described hereinabove) to the binding agent, then often linker molecules will be used. Preferred "linker molecules" or "linkers" are peptides of 1 to 200 amino acids length, and are typically, but not necessarily, chosen or designed to be unstructured and flexible. For instance, one can choose amino acids that form no particular secondary structure. Or, amino acids can be chosen so that they do not form a stable tertiary structure. Or, the amino acid linkers may form a random coil. Such linkers include, but are not limited to, synthetic peptides rich in Gly, Ser, Thr, Gln, Glu or further amino acids that are frequently associated with unstructured regions in natural proteins (Dosztányi, Z., Csizmok, V., Tompa, P., & Simon, I. (2005). IUPred: web server for the prediction of intrinsically unstructured regions of proteins based on estimated energy content. Bioinformatics (Oxford, England), 21(16), 3433-4.). Non-limiting examples of suitable linker sequences include (GS)5 (GSGSGSGSGS; SEQ ID NO: 56), (GS)10 (GSGSGSGSGSGSGSGSGSGS; SEQ ID NO: 57), (G4S)3 (GGGGSGGGGSGGGGS; SEQ ID NO: 58), llama IgG2 hinge (AHHSEDPSSKAPKAPMA; SEQ ID NO: 59) or human IgA hinge (SPSTPPTPSPSTPPAS; SEQ ID NO: 60) linkers.

Thus, according to specific embodiments, the amino acid (AA) linker sequence is a peptide of between 0 and 200 AA, between 0 and 150 AA, between 0 and 100 AA, between 0 and 90 AA, between 0 and 80 AA, between 0 and 70 AA, between 0 and 60 AA, between 0 and 50 AA, between 0 and 40 AA, between 0 and 30 amino acids, between 0 and 20 AA, between 0 and 10 amino acids, between 0 and 5 amino acids. Examples of sequences of short linkers include, but are not limited to, PPP, PP or GS.

For certain applications, it may be advantageous that the linker molecule comprises or consists of one or more particular sequence motifs. For example, a proteolytic cleavage site can be introduced into the linker molecule such that detectable label or moiety can be released. Useful cleavage sites are known in the art, and include a protease cleavage site such as Factor Xa cleavage site having the sequence IEGR (SEQ ID NO: 61), the thrombin cleavage site having the sequence LVPR (SEQ ID NO: 62), the enterokinase cleaving site having the sequence DDDDK (SEQ ID NO: 63), or the PreScission —or 3C— cleavage site LEVLFQGP (SEQ ID NO: 64).

Alternatively, in case the binding agent is linked to a detectable label or moiety using chemoenzymatic methods for protein modification, the linker moiety may exist of different chemical entities, depending on the enzymes or the synthetic chemistry that is used to produce the covalently coupled molecule in vivo or in vitro (reviewed in: Rabuka 2010, Curr. Opin. Chem. Biol. 14: 790-796).

Expression Systems

In one other aspect, the invention relates to a nucleic acid molecule comprising a nucleic acid sequence encoding any of the binding agents hereof as described hereinbefore. Further, the disclosure also envisages expression vectors comprising nucleic acid sequences encoding any of the binding agents hereof, as well as host cells expressing such expression vectors. Suitable expression systems include constitutive and inducible expression systems in bacteria or yeasts, virus expression systems, such as baculovirus, semliki forest virus and lentiviruses, or transient transfection in insect or mammalian cells. The cloning and/or expression of the binding agents hereof can be done according to techniques known by the skilled person in the art.

The "host cell" according to the disclosure can be of any prokaryotic or eukaryotic organism. According to a preferred embodiment, the host cell is a eukaryotic cell and can be of any eukaryotic organism, but in particular embodiments yeast, plant, mammalian and insect cells are envisaged. The nature of the cells used will typically depend on the ease and cost of producing the binding agent, the desired glycosylation properties, the origin of the binding agent, the intended application, or any combination thereof. Mammalian cells may, for instance, be used for achieving complex glycosylation, but it may not be cost-effective to produce proteins in mammalian cell systems. Plant and insect cells, as well as yeast typically achieve high production levels and are more cost-effective, but additional modifications may be needed to mimic the complex glycosylation patterns of mammalian proteins. Yeast cells are often used for expression of proteins because they can be economically cultured, give high yields of protein, and when appropriately modified are capable of producing proteins having suitable glycosylation patterns. Further, yeast offers established genetics allowing for rapid transformations, tested protein localization strategies, and facile gene knock-out techniques. Insect cells are also an attractive system to express GPCRs including opioid receptors because insect cells offer an expression system without interfering with mammalian GPCR signaling. Eukaryotic cell or cell lines for protein production are well known in the art, including cell lines with modified glycosylation pathways, and non-limiting examples will be provided hereafter.

Animal or mammalian host cells suitable for harboring, expressing, and producing proteins for subsequent isolation and/or purification include Chinese hamster ovary cells (CHO), such as CHO-K1 (ATCC CCL-61), DG44 (Chasin et al., 1986; Kolkekar et al., 1997), CHO-K1 Tet-On cell line (Clontech), CHO designated ECACC 85050302 (CAMR, Salisbury, Wiltshire, UK), CHO clone 13 (GEIMG, Genova, IT), CHO clone B (GEIMG, Genova, IT), CHO-K1/SF designated ECACC 93061607 (CAMR, Salisbury, Wiltshire, UK), RR-CHOK1 designated ECACC 92052129

(CAMR, Salisbury, Wiltshire, UK), dihydrofolate reductase negative CHO cells (CHO/-DHFR, Urlaub and Chasin, 1980), and dp12.CHO cells (U.S. Pat. No. 5,721,121); monkey kidney CV1 cells transformed by SV40 (COS cells, COS-7, ATCC CRL-1651); human embryonic kidney cells (e.g., HEK293 cells, or 293T cells, or 293 cells subcloned for growth in suspension culture, Graham et al., 1977, J. Gen. Virol., 36:59, or GnTI KO HEK293S cells, Reeves et al., 2002); baby hamster kidney cells (BHK, ATCC CCL-10); monkey kidney cells (CV1, ATCC CCL-70); African green monkey kidney cells (VERO-76, ATCC CRL-1587; VERO, ATCC CCL-81); mouse sertoli cells (TM4, Mather, 1980, Biol. Reprod., 23:243-251); human cervical carcinoma cells (HELA, ATCC CCL-2); canine kidney cells (MDCK, ATCC CCL-34); human lung cells (W138, ATCC CCL-75); human hepatoma cells (HEP-G2, HB 8065); mouse mammary tumor cells (MMT 060562, ATCC CCL-51); buffalo rat liver cells (BRL 3A, ATCC CRL-1442); TRI cells (Mather, 1982); MCR 5 cells; FS4 cells. According to a particular embodiment, the cells are mammalian cells selected from Hek293 cells or COS cells.

Exemplary non-mammalian cell lines include, but are not limited to, insect cells, such as Sf9 cells/baculovirus expression systems (e.g., review Jarvis, Virology Volume 310, Issue 1, 25 May 2003, Pages 1-7), plant cells such as tobacco cells, tomato cells, maize cells, algae cells, or yeasts such as *Saccharomyces* species, *Schizosaccharomyces* species, *Hansenula* species, *Yarrowia* species or *Pichia* species. According to particular embodiments, the eukaryotic cells are yeast cells from a *Saccharomyces* species (e.g., *Saccharomyces cerevisiae*), *Schizosaccharomyces* sp. (for example, *Schizosaccharomyces pombe*), a *Hansenula* species (e.g., *Hansenula polymorpha*), a *Yarrowia* species (e.g., *Yarrowia lipolytica*), a *Kluyveromyces* species (e.g., *Kluyveromyces lactis*), a *Pichia* species (e.g., *Pichia pastoris*), or a *Komagataella* species (e.g., *Komagataella pastoris*). According to a specific embodiment, the eukaryotic cells are *Pichia* cells and, in a most particular embodiment, *Pichia pastoris* cells.

Transfection of target cells (e.g., mammalian cells) can be carried out following principles outlined by Sambrook and Russel (Molecular Cloning, A Laboratory Manual, 3rd Edition, Volume 3, Chapter 16, Section 16.1-16.54). In addition, viral transduction can also be performed using reagents such as adenoviral vectors. Selection of the appropriate viral vector system, regulatory regions and host cell is common knowledge within the level of ordinary skill in the art. The resulting transfected cells are maintained in culture or frozen for later use according to standard practices.

Accordingly, another aspect hereof relates to a method for producing a binding agent according to the invention, the method comprising at least the steps of:
a) Expressing in a suitable cellular expression system (as defined hereinabove), a nucleic acid encoding a binding agent according to the invention, and optionally
b) Isolating and/or purifying the binding agent.

The above-described binding agents, as well as the complexes comprising the same, are particularly useful for screening and drug discovery (in its broadest sense), all of which is now detailed further herein.

Applications

The herein described binding agents can be used in a variety of contexts and applications, for example and without limitation: (1) for capturing and/or purification of an opioid receptor whereby upon binding, the binding agent maintains the receptor in a particular conformation; (2) for co-crystallization studies and high-resolution structural analysis of an opioid receptor in complex with the binding agent, and optionally additionally bound to another conformation-selective receptor ligand; (3) for ligand characterization, compound screening, and (structure-based) drug discovery; (4) as therapeutics or for diagnostic applications; (5) as biosensor, all of which will be described in further detail below.

Capturing, Separation and Purification Methods for Opioid Receptor in a Functional Conformation In another aspect, the invention provides a method for capturing and/or purifying an opioid receptor in a functional conformation, preferably an active or inactive conformation, by making use of any of the above described binding agents. Capturing and/or purifying a receptor in a particular conformation will allow subsequent crystallization, ligand characterization and compound screening, immunizations, amongst others.

Thus, in a particular embodiment, the invention relates to the use of a binding agent according to the invention to capture an opioid receptor in an active or inactive conformation. Optionally, but not necessarily, capturing of a receptor in a particular conformation as described above may include capturing a receptor in complex with another conformation-selective receptor ligand (e.g., an orthosteric ligand, an allosteric ligand, a natural binding partner such as a G protein or an arrestin, and the like).

In accordance, the invention also provides a method of capturing an opioid receptor in a functional conformation, the method comprising the steps of:
(i) bringing a binding agent according to the invention into contact with a solution comprising an opioid receptor, and
(ii) allowing the binding agent to specifically bind to the opioid receptor, whereby an opioid receptor is captured in a functional conformation.

More specifically, the invention also envisages a method of capturing an opioid receptor in a functional conformation, the method comprising the steps of:
(i) applying a solution containing an opioid receptor in a plurality of conformations to a solid support possessing an immobilized binding agent according to the invention, and
(ii) allowing the binding agent to specifically bind to the opioid receptor, whereby an opioid receptor is captured in a functional conformation, and
(iii) removing weakly bound or unbound molecules.

It will be appreciated that any of the methods as described above may further comprise the step of isolating the complex formed in step (ii) of the above-described methods, the complex comprising the binding agent and the opioid receptor in a particular conformation.

The above methods for isolating/purifying opioid receptors include, without limitation, affinity-based methods such as affinity chromatography, affinity purification, immunoprecipitation, protein detection, immunochemistry, surface-display, size exclusion chromatography, ion exchange chromatography, amongst others, and are all well known in the art.

Crystallography and Applications in Structure-based Drug Design

One aspect of the disclosure relates to the usefulness of the binding agents hereof in X-ray crystallography of opioid receptors and its applications in structure-based drug design. With the inactive-state structure of the mu opioid receptor that is available in the art, pharmaceutical chemists now have experimental data to guide the development of conformation-selective ligands, such as ligands that selectively bind active state and will activate opioid receptors. However, the value of these high-resolution structures for in silico screening is limited. On the other hand, and as a matter of illustration, agonist-bound receptor crystals may provide three-dimensional representations of the active states of opioid receptors. These structures will help clarify the conformational changes connecting the ligand-binding and G-protein-interaction sites, and lead to more precise mechanistic hypotheses and eventually new therapeutics. Given the conformational flexibility inherent to ligand-activated GPCRs, stabilizing such a state is not easy. Such efforts can benefit from the stabilization of the agonist-bound receptor conformation by the addition of binding agents that are specific for an active conformational state of the receptor. In that regard, it is a particular advantage of the disclosure that binding agents are found that show G-protein like behavior and exhibit cooperative properties with respect to agonist binding (see also Example section). This will also be of great advantage to help guide drug discovery. Especially methods for acquiring structures of receptors bound to lead compounds that have pharmacological or biological activity and whose chemical structure is used as a starting point for chemical modifications in order to improve potency, selectivity, or pharmacokinetic parameters are very valuable and are provided herein. Persons of ordinary skill in the art will recognize that the binding agent hereof is particularly suited for co-crystallization of receptor:binding agent with lead compounds that are selective for the druggable conformation induced by the binding agent because this binding agent is able to substantially increase the affinity for conformation-selective receptor ligands.

It is thus a particular advantage of the binding agents hereof that the binding agent binds a conformational epitope on the receptor, thus stabilizing the receptor in that particular conformation, reducing its conformational flexibility and increasing its polar surface, facilitating the crystallization of a receptor:binding agent complex. The binding agents of the disclosure are unique tools to increase the probability of obtaining well-ordered crystals by minimizing the conformational heterogeneity in the target opioid receptor.

Thus, according to one embodiment, it is envisaged to use the binding agents hereof for crystallization purposes. Advantageously, crystals can be formed of a complex of a binding agent and the opioid receptor, wherein the receptor is trapped in a particular receptor conformation, more particularly, a therapeutically relevant receptor conformation (e.g., an active conformation), as ensured by the choice of a binding agent. The binding agent will also reduce the flexibility of extracellular regions upon binding the receptor to grow well-ordered crystals. In particular, immunoglobulin single variable domains, including Nanobodies, are especially suitable binding agents for this purpose because they bind conformational epitopes and are composed of one single rigid globular domain, devoid of flexible linker regions unlike conventional antibodies or fragments derived such as Fabs.

Thus, according to a preferred embodiment, the disclosure provides for binding agents useful as tools for crystallizing a complex of a binding agent and an opioid receptor to which the binding agent will specifically bind, and eventually to solve the structure of the complex. According to a specific embodiment, the disclosure also envisages to crystallize a complex of binding agent, an opioid receptor to which the binding agent will specifically bind, and another conformation-selective receptor ligand (as defined hereinbefore). Thus, the complex comprising the binding agent according to the invention and the opioid receptor maintained in a particular conformation, may be crystallized using any of a variety of specialized crystallization methods for membrane proteins, many of which are reviewed in Caffrey (2003 & 2009). In general terms, the methods are lipid-based methods that include adding lipid to the complex prior to crystallization. Such methods have previously been used to crystallize other membrane proteins. Many of these methods, including the lipidic cubic phase crystallization method and the bicelle crystallization method, exploit the spontaneous self-assembling properties of lipids and detergent as vesicles (vesicle-fusion method), discoidal micelles (bicelle method), and liquid crystals or mesophases (in meso or cubic-phase method). Lipidic cubic phases crystallization methods are described in, for example: Landau et al., 1996; Gouaux 1998; Rummel et al., 1998; Nollert et al., 2004, Rasmussen et al., 2011a and b, which publications are incorporated by reference for invention of those methods. Bicelle crystallization methods are described in, for example: Faham et al., 2005; Faham et al., 2002, which publications are incorporated by reference for invention of those methods.

According to another embodiment, the invention relates to the use of a binding agent as described herein to solve the structure of an opioid receptor in complex with a binding agent, and optionally in complex with another receptor ligand. "Solving the structure" as used herein refers to determining the arrangement of atoms or the atomic coordinates of a protein, and is often done by a biophysical method, such as X-ray crystallography.

In many cases, obtaining a diffraction-quality crystal is the key barrier to solving its atomic-resolution structure. Thus, according to specific embodiments, the herein described binding agents can be used to improve the diffraction quality of the crystals so that the crystal structure of the receptor:binding agent complex can be solved.

In accordance, the disclosure encompasses a method of determining the crystal structure of an opioid receptor in a functional conformation, the method comprising the steps of:
  a) Providing a binding agent according to the invention and a target opioid receptor, and optionally a receptor ligand, and
  b) Allowing the formation of a complex of the binding agent, the opioid receptor and optionally a receptor ligand,
  c) Crystallizing the complex of step b) to form a crystal.

Determining the crystal structure may be done by a biophysical method such as X-ray crystallography. The method may further comprise a step for obtaining the atomic coordinates of the crystal (as defined hereinbefore).

Ligand Screening and Drug Discovery

Other applications are particularly envisaged that can make use of the binding agents hereof, including compound screening and immunizations, which will be described further herein.

In the process of compound screening, lead optimization and drug discovery (including peptide and antibody discovery), there is a requirement for faster, more effective, less expensive and especially information-rich screening assays that provide simultaneous information on various compound characteristics and their effects on various cellular pathways (i.e., efficacy, specificity, toxicity and drug metabolism). Thus, there is a need to quickly and inexpensively screen large numbers of compounds in order to identify new specific ligands of a protein of interest, preferably conformation-selective ligands, which may be potential new drug candidates. The disclosure solves this problem by providing binding agents that stabilize or lock an opioid receptor in a functional conformation, preferably in an active or inactive conformation. This will allow to quick and reliably screen for and differentiate between receptor agonists, inverse agonists, antagonists and/or modulators as well as inhibitors of opioid receptors, so increasing the likelihood of identifying a ligand with the desired pharmacological properties. In particular, the binding agents, the complexes comprising the same, the host cells comprising the same, as well as host cell cultures or membrane preparations derived thereof are provided, for which specific preferences have been described hereinbefore, are particularly suitable for this purpose, and can then be used as immunogens or selection reagents for screening in a variety of contexts.

To illustrate this further, the binding agents according to the invention that recognize the active conformation of an opioid receptor will preferably be used in screening assays to screen for agonists because they increase the affinity of the receptor for agonists, relative to inverse agonists or antagonists. Reciprocally, binding agents that stabilize the inactive state conformation of an opioid receptor will increase the affinity for an inverse agonist, relative to agonists or antagonists. Such binding agents will preferably be used to screen for inverse agonists.

Thus, according to a preferred embodiment, the disclosure encompasses the use of the binding agents, complexes comprising the same, host cells comprising the same, host cell cultures, or membrane preparations derived thereof, according to the invention and as described hereinbefore, in screening and/or identification programs for binding partners of an opioid receptor, which ultimately might lead to potential new drug candidates.

According to one embodiment, the invention envisages a method of identifying conformation-selective compounds, the method comprising the steps of:
(i) Providing a complex comprising an opioid receptor and a binding agent specifically binding to the receptor, and
(ii) Providing a test compound, and
(iii) Evaluating whether the test compound is a conformation-selective compound for the receptor.

Specific preferences for the binding agents, complexes, host cells, host cell cultures and membrane preparations thereof are as defined above with respect to earlier aspects hereof.

In a preferred embodiment, the binding agent, the opioid receptor or the complex comprising the binding agent and the opioid receptor, as used in any of the screening methods described herein, are provided as whole cells, or cell (organelle) extracts such as membrane extracts or fractions thereof, or may be incorporated in lipid layers or vesicles (comprising natural and/or synthetic lipids), high-density lipoparticles, or any nanoparticle, such as nanodisks, or are provided as virus or virus-like particles (VLPs), so that sufficient functionality of the respective proteins is retained. Methods for preparations of GPCRs from membrane fragments or membrane-detergent extracts are reviewed in detail in Cooper (2004), incorporated herein by reference. Alternatively, the receptor and/or the complex may also be solubilized in detergents. Non-limiting examples of liposome reconstituted receptor preparations are also provided in the Example section.

Often high-throughput screening for binding partners of receptors will be preferred. This may be facilitated by immobilization of either the binding agent according to the invention, the opioid receptor or the complex comprising the binding agent and the opioid receptor, onto a suitable solid surface or support that can be arrayed or otherwise multiplexed. Non-limiting examples of suitable solid supports include beads, columns, slides, chips or plates.

More particularly, the solid supports may be particulate (e.g., beads or granules, generally used in extraction columns) or in sheet form (e.g., membranes or filters, glass or plastic slides, microtiter assay plates, dipstick, capillary fill devices or such like) which can be flat, pleated, or hollow fibers or tubes. The following matrices are given as examples and are not exhaustive, such examples could include silica (porous amorphous silica), i.e., the FLASH series of cartridges containing 60A irregular silica (32-63 um or 35-70 um) supplied by Biotage (a division of Dyax Corp.), agarose or polyacrylamide supports, for example, the Sepharose range of products supplied by Amersham Pharmacia Biotech, or the Affi-Gel supports supplied by Bio-Rad. In addition there are macroporous polymers, such as the pressure-stable Affi-Prep supports as supplied by Bio-Rad. Other supports that could be utilized include: dextran, collagen, polystyrene, methacrylate, calcium alginate, controlled pore glass, aluminium, titanium and porous ceramics. Alternatively, the solid surface may comprise part of a mass dependent sensor, for example, a surface plasmon resonance detector. Further examples of commercially available supports are discussed in, for example, Protein Immobilization, R.F. Taylor ed., Marcel Dekker, Inc., New York, (1991).

Immobilization may be either non-covalent or covalent. In particular, non-covalent immobilization or adsorption on a solid surface of the binding agent, the opioid receptor or the complex comprising the binding agent and the opioid receptor, may occur via a surface coating with any of an antibody, or streptavidin or avidin, or a metal ion, recognizing a molecular tag attached to the binding agent, according to standard techniques known by the skilled person (e.g., biotin tag, Histidine tag, etc.).

In particular, the binding agent, the opioid receptor or the complex comprising the binding agent and the opioid receptor, may be attached to a solid surface by covalent cross-linking using conventional coupling chemistries. A solid surface may naturally comprise cross-linkable residues suitable for covalent attachment or it may be coated or derivatized to introduce suitable cross-linkable groups according to methods well known in the art. In one particular embodiment, sufficient functionality of the immobilized protein is retained following direct covalent coupling to the desired matrix via a reactive moiety that does not contain a chemical spacer arm. Further examples and more detailed information on immobilization methods of antibody (fragments) on solid supports are discussed in Jung et al. (2008); similarly, membrane receptor immobilization methods are reviewed in Cooper (2004); both herein incorporated by reference.

Advances in molecular biology, particularly through site-directed mutagenesis, enable the mutation of specific amino acid residues in a protein sequence. The mutation of a particular amino acid (in a protein with known or inferred structure) to a lysine or cysteine (or other desired amino acid) can provide a specific site for covalent coupling, for example. It is also possible to reengineer a specific protein to alter the distribution of surface available amino acids involved in the chemical coupling (Kallwass et al., 1993), in effect controlling the orientation of the coupled protein. A similar approach can be applied to the binding agents according to the invention, as well as to the conformationally stabilized opioid receptors, whether or not comprised in the complex, so providing a means of oriented immobilization without the addition of other peptide tails or domains containing either natural or unnatural amino acids. In case of an antibody or an antibody fragment, such as a Nanobody, introduction of mutations in the framework region is preferred, minimizing disruption to the antigen-binding activity of the antibody (fragment).

Conveniently, the immobilized proteins may be used in immunoadsorption processes such as immunoassays, for example, ELISA, or immunoaffinity purification processes by contacting the immobilized proteins according to the invention with a test sample according to standard methods conventional in the art. Alternatively, and particularly for high-throughput purposes, the immobilized proteins can be arrayed or otherwise multiplexed. Preferably, the immobilized proteins according to the invention are used for the screening and selection of compounds that selectively bind to a particular conformation of an opioid receptor.

It will be appreciated that either the binding agent or the target opioid receptor may be immobilized, depending on the type of application or the type of screening that needs to be done. Also, the choice of the binding agent (targeting a particular conformational epitope of the receptor), will determine the orientation of the receptor and accordingly, the desired outcome of the compound identification, e.g., compounds specifically binding to extracellular parts, intramembranal parts or intracellular parts of the conformationally stabilized receptor.

In an alternative embodiment, the test compound (or a library of test compounds) may be immobilized on a solid surface, such as a chip surface, whereas the binding agent and opioid receptor are provided, for example, in a detergent solution or in a membrane-like preparation.

Accordingly, in one specific embodiment, a solid support to which is immobilized a binding agent according to the invention is provided for use in any of the above screening methods.

Most preferably, neither the binding agent, nor the opioid receptor, nor the test compound are immobilized, for example, in phage-display selection protocols in solution, or radioligand binding assays.

Screening assays for drug discovery can be solid phase (e.g., beads, columns, slides, chips or plates) or solution phase assays, e.g., a binding assay, such as radioligand binding assays. In high-throughput assays, it is possible to screen up to several thousand different compounds in a single day in 96-, 384- or 1536-well formats. For example, each well of a microtiter plate can be used to run a separate assay against a selected potential modulator, or, if concentration or incubation time effects are to be observed, every 5-10 wells can test a single modulator. Thus, a single standard microtiter plate can assay about 96 modulators. It is possible to assay many plates per day; assay screens for up to about 6,000, 20,000, 50,000 or more different compounds are possible today. Preferably, a screening for opioid receptor conformation-selective compounds will be performed starting from host cells, or host cell cultures, or membrane preparations derived thereof.

Various methods may be used to determine binding between the stabilized opioid receptor and a test compound including, for example, flow cytometry, radioligand binding assays, enzyme linked immunosorbent assays (ELISA), surface plasmon resonance assays, chip-based assays, immunocytofluorescence, yeast two-hybrid technology and phage display, which are common practices in the art, for example, in Sambrook et al. (2001), Molecular Cloning, A Laboratory Manual. Third Edition. Cold Spring Harbor Laboratory Press, Cold Spring Harbor, N.Y. Other methods of detecting binding between a test compound and a membrane protein include ultrafiltration with ion spray mass spectroscopy/HPLC methods or other (bio)physical and analytical methods. Fluorescence Energy Resonance Transfer (FRET) methods, for example, well known to those skilled in the art, may also be used. It will be appreciated that a bound test compound can be detected using a unique label or tag associated with the compound, such as a peptide label, a nucleic acid label, a chemical label, a fluorescent label, or a radioactive isotope label, as described further herein.

The compounds to be tested can be any small chemical compound, or a macromolecule, such as a protein, a sugar, nucleic acid or lipid. Typically, test compounds will be small chemical compounds, peptides, antibodies or fragments thereof. It will be appreciated that in some instances the test compound may be a library of test compounds. In particular, high-throughput screening assays for therapeutic compounds such as agonists, antagonists or inverse agonists and/or modulators form part hereof. For high-throughput purposes, compound libraries or combinatorial libraries may be used such as allosteric compound libraries, peptide libraries, antibody libraries, fragment-based libraries, synthetic compound libraries, natural compound libraries, phage-display libraries and the like. Methodologies for preparing and screening such libraries are known to those of skill in the art.

The test compound may optionally be covalently or non-covalently linked to a detectable label. Suitable detectable labels and techniques for attaching, using and detecting them will be clear to the skilled person, and include, but are not limited to, any composition detectable by spectroscopic, photochemical, biochemical, immunochemical, electrical, optical or chemical means. Useful labels include magnetic beads (e.g., dynabeads), fluorescent dyes (e.g., all Alexa Fluor dyes, fluorescein isothiocyanate, Texas red, rhodamine, green fluorescent protein and the like), radiolabels (e.g., $^3$H, $^{125}$I, $^{35}$S, $^{14}$C, or $^{32}$P), enzymes (e.g., horse radish peroxidase, alkaline phosphatase), and colorimetric labels such as colloidal gold or colored glass or plastic (e.g., polystyrene, polypropylene, latex, etc.) beads. Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label. Other suitable detectable labels were described earlier within the context of the first aspect hereof relating to a binding agent.

Thus, according to specific embodiments, the test compound as used in any of the above screening methods is selected from the group comprising a polypeptide, a peptide, a small molecule, a natural product, a peptidomimetic, a nucleic acid, a lipid, lipopeptide, a carbohydrate, an antibody or any fragment derived thereof, such as Fab, Fab' and F(ab')2, Fd, single-chain Fvs (scFv), single-chain antibodies, disulfide-linked Fvs (dsFv) and fragments comprising either a VL or VH domain, a heavy chain antibody (hcAb), a single domain antibody (sdAb), a minibody, the variable domain derived from camelid heavy chain antibodies (VHH or Nanobody), the variable domain of the new antigen receptors derived from shark antibodies (VNAR), a protein scaffold including an alphabody, protein A, protein G, designed ankyrin-repeat domains (DARPins), fibronectin type III repeats, anticalins, knottins, engineered CH2 domains (nanoantibodies), as defined hereinbefore.

In one preferred embodiment, high throughput screening methods involve providing a combinatorial chemical or peptide library containing a large number of potential therapeutic ligands. Such "combinatorial libraries" or "compound libraries" are then screened in one or more assays, as described herein, to identify those library members (particular chemical species or subclasses) that display a desired characteristic activity. A "compound library" is a collection of stored chemicals usually used ultimately in high-throughput screening A "combinatorial library" is a collection of diverse chemical compounds generated by either chemical synthesis or biological synthesis, by combining a number of chemical "building blocks" such as reagents. Preparation and screening of combinatorial libraries are well known to those of skill in the art. The compounds thus identified can serve as conventional "lead compounds" or can themselves be used as potential or actual therapeutics. Thus, in one further embodiment, the screening methods as described herein above further comprises modifying a test compound which has been shown to selectively bind to an opioid receptor in a particular conformation, and determining whether the modified test compound binds to the receptor when residing in the particular conformation.

In one embodiment, it is determined whether the compound alters the binding of the opioid receptor to a receptor ligand (as defined herein). Binding of a receptor to its ligand can be assayed using standard ligand binding methods known in the art as described herein. For example, a ligand may be radiolabeled or fluorescently labeled. The assay may be carried out on whole cells or on membranes obtained from the cells or aqueous solubilized receptor with a detergent. The compound will be characterized by its ability to alter the binding of the labeled ligand. The compound may decrease the binding between the receptor and its ligand, or may increase the binding between the receptor and its ligand, for example, by a factor of at least two-fold, three-fold, four-fold, five-fold, ten-fold, twenty-fold, thirty-fold, fifty-fold, one hundred-fold.

Thus, according to more specific embodiments, a complex comprising a binding agent hereof, an opioid receptor and a receptor ligand may be used in any of the above screening methods. Preferably, the receptor ligand is chosen from the group comprising a small molecule, a polypeptide, an antibody or any fragment derived thereof, a natural product, and the like. More preferably, the receptor ligand is a full agonist, or a partial agonist, a biased agonist, an antagonist, or an inverse agonist, as described hereinbefore.

According to a particular embodiment, the test compound as used in any of the above screening methods is provided as a biological sample. In particular, the sample can be any suitable sample taken from an individual. For example, the sample may be a body fluid sample such as blood, serum, plasma, spinal fluid.

In addition to establishing binding to an opioid receptor in a particular conformation of interest, it will also be desirable to determine the functional effect of a compound on the receptor. For example, the compounds may bind to the opioid receptor resulting in the modulation (activation or inhibition) of the biological function of the receptor, in particular the downstream receptor signaling. This modulation of intracellular signaling can occur ortho- or allosterically. The compounds may bind to the opioid receptor so as to activate or increase receptor signaling; or alternatively so as to decrease or inhibit receptor signaling. The compounds may also bind to the opioid receptor in such a way that they block off the constitutive activity of the receptor. The compounds may also bind to the opioid receptor in such a way that they mediate allosteric modulation (e.g., bind to the receptor at an allosteric site). In this way, the compounds may modulate the receptor function by binding to different regions in the receptor (e.g., at allosteric sites). Reference is made, for example, to George et al., 2002; Kenakin 2002; Rios et al., 2001. The compounds hereof may also bind to the opioid receptor in such a way that they prolong the duration of the receptor-mediated signaling or that they enhance receptor signaling by increasing receptor-ligand affinity. Further, the compounds may also bind to the opioid receptor in such a way that they inhibit or enhance the assembly of receptor functional homomers or heteromers. The efficacy of the compounds and/or compositions comprising the same can be tested using any suitable in vitro assay, cell-based assay, in vivo assay and/or animal model known per se, or any combination thereof, depending on the specific disease or disorder involved.

It will be appreciated that the binding agents, complexes, host cells and derivatives thereof, according to the disclosure, may be further engineered and are thus particularly useful tools for the development or improvement of cell-based assays. Cell-based assays are critical for assessing the mechanism of action of new biological targets and biological activity of chemical compounds. For example, without the purpose of being limitative, current cell-based assays for GPCRs include measures of pathway activation ($Ca^{2+}$ release, cAMP generation or transcriptional activity); measurements of protein trafficking by tagging GPCRs and downstream elements with GFP; and direct measures of interactions between proteins using Förster resonance energy transfer (FRET), bioluminescence resonance energy transfer (BRET) or yeast two-hybrid approaches.

Further, it may be particularly advantageous to immunize an animal with a complex comprising an opioid receptor and a binding agent that is directed against and/or specifically binds to the receptor, or with a host cell comprising the complex, or derivative thereof, in order to raise antibodies, preferably conformation-selective antibodies against the opioid receptor. Thus, such immunization methods are also envisaged here. Methods for raising antibodies in vivo are known in the art, and are also described hereinbefore. Any suitable animal, for example, a mammal such as a rabbit, mouse, rat, camel, sheep, cow, pig, or a bird such as a chicken or turkey, or a fish such as a shark, may be immunized using any of the techniques well known in the art suitable for generating an immune response. Following immunization, expression libraries encoding immunoglobulin genes, or portions thereof, expressed in bacteria, yeast, filamentous phage, ribosomes or ribosomal subunits or other display systems, can be made according to well-known techniques in the art. Further to that, the antibody libraries that are generated comprise a collection of suitable test compounds for use in any of the screening methods as described hereinbefore. The antibodies that have been raised as described herein above may also be useful diagnostic tools to specifically detect opioid receptors in a particular conformation, and thus also form part of the disclosure.

In one embodiment, the complex comprising the opioid receptor and the binding agent that is directed against and/or specifically binds to the opioid receptor may be used for the selection of binding agents including antibodies or antibody fragments that bind the receptor by any of the screening methods as described above. Persons of ordinary skill in the art will recognize that such binding agents, as a non-limiting example, can be selected by screening a set, collection or library of cells that express binding agents on their surface, or bacteriophages that display a fusion of genIII and binding agent at their surface, or yeast cells that display a fusion of the mating factor protein Aga2p, or by ribosome display amongst others.

Therapeutic and Diagnostic Applications

A further aspect relates to a pharmaceutical composition comprising a therapeutically effective amount of a binding agent according to the invention and at least one of a pharmaceutically acceptable carrier, adjuvant or diluents.

A "carrier" or "adjuvant," in particular, a "pharmaceutically acceptable carrier" or "pharmaceutically acceptable adjuvant" is any suitable excipient, diluent, carrier and/or adjuvant which, by themselves, do not induce the production of antibodies harmful to the individual receiving the composition nor do they elicit protection. So, pharmaceutically acceptable carriers are inherently non-toxic and nontherapeutic, and they are known to the person skilled in the art. Suitable carriers or adjuvantia typically comprise one or more of the compounds included in the following non-exhaustive list: large slowly metabolized macromolecules such as proteins, polysaccharides, polylactic acids, polyglycolic acids, polymeric amino acids, amino acid copolymers and inactive virus particles. Carriers or adjuvants may be, as a non-limiting example, Ringer's solution, dextrose solution or Hank's solution. Non-aqueous solutions such as fixed oils and ethyl oleate may also be used. A preferred excipient is 5% dextrose in saline. The excipient may contain minor amounts of additives such as substances that enhance isotonicity and chemical stability, including buffers and preservatives.

The administration of a binding agent according to the invention or a pharmaceutical composition thereof may be by way of oral, inhaled or parenteral administration. In particular embodiments, the binding agent is delivered through intrathecal or intracerebroventricular administration. The active compound may be administered alone or preferably formulated as a pharmaceutical composition. An amount effective to treat a certain disease or disorder that express the antigen recognized by the protein binding domain depends on the usual factors such as the nature and severity of the disorder being treated and the weight of the mammal. However, a unit dose will normally be in the range of 0.1 mg to 1 g, for example, to 0.1 to 500 mg, for example, 0.1 to 50 mg, or 0.1 to 2 mg of protein binding domain or a pharmaceutical composition thereof. Unit doses will normally be administered once a month, once a week, bi-weekly, once or more than once a day, for example, 2, 3, or 4 times a day, more usually 1 to 3 times a day. It is greatly preferred that the binding agent or a pharmaceutical composition thereof is administered in the form of a unit-dose composition, such as a unit dose oral, parenteral, or inhaled composition. Such compositions are prepared by admixture and are suitably adapted for oral, inhaled or parenteral administration, and as such may be in the form of tablets, capsules, oral liquid preparations, powders, granules, lozenges, reconstitutable powders, injectable and infusable solutions or suspensions or suppositories or aerosols. Tablets and capsules for oral administration are usually presented in a unit dose, and contain conventional excipients such as binding agents, fillers, diluents, tabletting agents, lubricants, disintegrants, colorants, flavorings, and wetting agents. The tablets may be coated according to well-known methods in the art. Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate. These solid oral compositions may be prepared by conventional methods of blending, filling, tabletting or the like. Repeated blending operations may be used to distribute the active agent throughout those compositions employing large quantities of fillers. Such operations are, of course, conventional in the art. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example, sorbitol, syrup, methyl cellulose, gelatin, hydroxyethylcellulose, carboxymethyl cellulose, aluminium stearate gel or hydrogenated edible fats, emulsifying agents, for example, lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example, methyl or propyl p-hydroxybenzoate or sorbic acid and, if desired, conventional flavoring or coloring agents. Oral formulations also include conventional sustained release formulations, such as tablets or granules having an enteric coating. Preferably, compositions for inhalation are presented for administration to the respiratory tract as a snuff or an aerosol or solution for a nebulizer, or as a microfine powder for insufflation, alone or in combination with an inert carrier such as lactose. In such a case, the particles of active compound suitably have diameters of less than 50 microns, preferably less than 10 microns, for example, between 1 and 5 microns, such as between 2 and 5 microns. A favored inhaled dose will be in the range of 0.05 to 2 mg, for example, 0.05 to 0.5 mg, 0.1 to 1 mg or 0.5 to 2 mg. For parenteral administration, fluid unit dose forms are prepared containing a compound of the disclosure and a sterile vehicle. The active compound, depending on the vehicle and the concentration, can be either suspended or dissolved. Parenteral solutions are normally prepared by dissolving the compound in a vehicle and filter sterilizing before filling into a suitable vial or ampoule and sealing. Advantageously, adjuvants such as a local anesthetic, preservatives and buffering agents are also dissolved in the vehicle. To enhance the stability, the composition can be frozen after filling into the vial and the water removed under vacuum. Parenteral suspensions are prepared in substantially the same manner except that the compound is suspended in the vehicle instead of being dissolved and sterilized by exposure to ethylene oxide before suspending in the sterile vehicle. Advantageously, a surfactant or wetting agent is included in the composition to facilitate uniform distribution of the active compound. Where appropriate, small amounts of bronchodilators, for example, sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included. As is common practice, the compositions will usually be accompanied by written or printed directions for use in the medical treatment concerned.

In the case of a biological, delivery of binding agents into cells may be performed as described for peptides, polypeptides and proteins. If the epitope is extracellular, the binding agent may exert its function by binding to the extracellular part, without need for intracellular delivery. The binding agents of the disclosure as described herein may target intracellular conformational epitopes of the opioid receptor. To use these binding agents as effective and safe therapeutics inside a cell, intracellular delivery may be enhanced by protein transduction or delivery systems know in the art. Protein transduction domains (PTDs) have attracted considerable interest in the drug delivery field for their ability to translocate across biological membranes. The PTDs are relatively short (1-35 amino acid) sequences that confer this apparent translocation activity to proteins and other macromolecular cargo to which they are conjugated, complexed or fused (Sawant and Torchilin 2010). The HIV-derived TAT peptide (YGRKKRRQRRR) (SEQ ID NO:88), for example, has been used widely for intracellular delivery of various agents ranging from small molecules to proteins, peptides, range of pharmaceutical nanocarriers and imaging agents. Alternatively, receptor-mediated endocytic mechanisms can also be used for intracellular drug delivery. For example, the transferrin receptor-mediated internalization pathway is an efficient cellular uptake pathway that has been exploited for site-specific delivery of drugs and proteins (Qian et al., 2002). This is achieved either chemically by conjugation of transferrin with therapeutic drugs or proteins or genetically by infusion of therapeutic peptides or proteins into the structure of transferrin. Naturally existing proteins (such as the iron-binding protein transferrin) are very useful in this area of drug targeting since these proteins are biodegradable, nontoxic, and non-immunogenic. Moreover, they can achieve site-specific targeting due to the high amounts of their receptors present on the cell surface. Still other delivery systems include, without the purpose of being limitative, polymer- and liposome-based delivery systems.

The efficacy of the binding agents hereof, and of compositions comprising the same, can be tested using any suitable in vitro assay, cell-based assay, in vivo assay and/or animal model known per se, or any combination thereof, depending on the specific disease or disorder involved.

Another aspect relates to the use of the binding agent or the pharmaceutical composition as described hereinbefore to modulate opioid receptor signaling activity.

The binding agents hereof as described herein may bind to the opioid receptor so as to activate or increase receptor signaling; or alternatively so as to decrease or inhibit receptor signaling. The binding agents hereof may also bind to the receptor in such a way that they block off the constitutive activity of the receptor. The binding agents hereof may also bind to the receptor in such a way that they mediate allosteric modulation (e.g., bind to the receptor at an allosteric site). In this way, the binding agents hereof may modulate the receptor function by binding to different regions in the receptor (e.g., at allosteric sites). Reference is made, for example, to George et al. (2002), Kenakin (2002) and Rios et al. (2001). The binding agents hereof may also bind to the receptor in such a way that they prolong the duration of the receptor-mediated signaling or that they enhance receptor signaling by increasing receptor-ligand affinity. Further, the binding agents hereof may also bind to the receptor in such a way that they inhibit or enhance the assembly of receptor functional homomers or heteromers.

In one particular embodiment, the binding agent or the pharmaceutical composition as described hereinbefore blocks G-protein mediated signaling.

In another embodiment, the invention also envisages the binding agent or the pharmaceutical composition as described hereinbefore for use in the treatment of an opioid receptor-related disease, in particular an opioid receptor-related disease indication.

It will thus be understood that certain of the above-described binding agents may have therapeutic utility and may be administered to a subject having a condition in order to treat the subject for the condition. The therapeutic utility for a binding agent may be determined by the opioid receptor to which the binding agent binds in that signaling via that receptor is linked to the condition. A binding agent may be employed for the treatment of an opioid receptor-mediated condition, such as pain, amongst others. Further exemplary opioid receptor-related conditions at the On-line Mendelian Inheritance in Man database found at the world wide website of the NCBI. So, a particular embodiment of the disclosure also envisions the use of a binding agent or of a pharmaceutical composition for the treatment of an opioid receptor-related disease or disorder.

In certain embodiments, the binding agents may be employed as co-therapeutic agents for use in combination with other drug substances, for example, as potentiators of therapeutic activity of such drugs or as a means of reducing required dosaging or potential side effects of such drugs. A binding agent may be mixed with the other drug substance in a fixed pharmaceutical composition or it may be administered separately, before, simultaneously with or after the other drug substance. In general terms, these protocols involve administering to an individual suffering from an opioid receptor-related disease or disorder, an effective amount of a binding agent that modulates an opioid receptor to modulate the receptor in the host and treat the individual for the disorder.

In some embodiments, where a reduction in activity of an opioid receptor is desired, one or more compounds that decrease the activity of the receptor may be administered, whereas when an increase in activity of an opioid receptor is desired, one or more compounds that increase the activity of the receptor activity may be administered.

A variety of individuals are treatable according to the subject methods. Generally, such individuals are mammals or mammalian, where these terms are used broadly to describe organisms, which are within the class mammalia, including the orders carnivore (e.g., dogs and cats), rodentia (e.g., mice, guinea pigs, and rats), and primates (e.g., humans, chimpanzees, and monkeys). In many embodiments, the individuals will be humans. Subject treatment methods are typically performed on individuals with such disorders or on individuals with a desire to avoid such disorders.

According to still another embodiment, the binding agents may also be useful for the diagnosis or prognosis of an opioid receptor-related disease indication, as described hereinbefore.

Kit of Parts

Still another aspect relates to a kit comprising a binding agent targeting an opioid receptor or a kit comprising a host cell or a host cell culture or a membrane preparation comprising a binding agent targeting an opioid receptor according to the invention. The kit may further comprise a combination of reagents such as buffers, molecular tags, vector constructs, reference sample material, as well as a suitable solid supports, and the like. Such a kit may be useful for any of the applications of the disclosure, as described herein. For example, the kit may comprise (a library of) test compounds useful for compound screening applications.

EXAMPLES

Example 1

Overexpression and Purification of Recombinant Mouse Mor1

To identify VHHs that interact with conformational epitopes of native μ-opioid receptor (Mor1), we overexpressed recombinant Mor1 in Sf9 insect cells. The mouse Mor1 AA sequence (uniprot code P42866) was optimized for recombinant expression in insect cells and purification: at the extreme N-terminus, the Flag tag encoding AA sequence DYKDDDDA (SEQ ID NO: 69) was introduced and AA residues 2-5 (DSSA) (SEQ ID NO: 70) were truncated. A TEV cleavage site "ENLYFQ" (SEQ ID NO: 71) was introduced after G51 and a 3C site "LEVLFQGP" (SEQ ID NO: 72) immediately after I358. At the extreme C-terminus, a histidine tag coding sequence DIHHHHHH (SEQ ID NO: 73) was introduced. The complete coding sequence of the recombinant mouse Mor1 variant used for recombinant expression in insect cells (Delta mMor1) is provided in Table 4 and an AA sequence alignment of WT mouse Mor1, Delta mMor1 and WT human Mor1 is depicted in FIG. 1.

To purify recombinant mouse Mor1, Delta mMor1 is expressed in Sf9 insect cells using the BestBac expression system (Expression Systems) according to the manufacturer's instructions. Recombinant expression of N-terminally Flag tagged Delta mMor1 was accomplished by infecting cultures of freshly grown Sf9 cells at a density of 1-4E6/ml with 200-fold diluted P2 Delta mMor1 baculovirus stocks. Infected cells were cultured for 48-60 hours at 27° C. (130 rpm) and were harvested by centrifugation for 5 minutes at 500×g. Cells overexpressing Delta mMor1 were washed twice with ice cold PBS, pelleted again by centrifugation and stored at −80° C. or immediately processed.

Delta mMor1 is solubilized from these pellets using detergents and purified by affinity chromatography steps using nickel and anti-Flag antibody (Manglik et al., 2012) using Mor1 ligand to stabilize the folded receptor. N- and C-termini are removed by enzymatic proteolysis, resulting in truncDelta mMor1. Finally, truncDelta mMor1 is purified to homogeneity by a subsequent polishing step via size exclusion chromatography.

After the receptor was bound to the M1 flag resin, the detergent in the buffer was changed from 0.1% dodecyl maltoside (DDM) to 0.01% lauryl maltose neopentyl glycol (MNG; Anatrace) through a gradual exchange as previously described (Kruse et al., 2013). In the end of the detergent exchange step, the receptor is washed with 20 mL ligand-free buffer (0.01% MNG, 0.001% cholesterol hemisuccinate, 25 mM HEPES pH 7.5, 100 mM NaCl). Receptor was eluted with addition of flag peptide. Agonist (Dmt1-Dalda) doped purified truncDelta mMor1 was reconstituted into lipid vesicles, consisting of synthetic lipids (DOPC, CHS Avanti Polar Lipids) and containing lipid A (Sigma) to stabilize truncDelta mMor1 in a membrane-mimicking environment as previously described for β2AR (Rasmussen 2011b). The liposome reconstituted truncDelta mMor1 was stored in aliquots at −80° C. prior to be used for immunization (Example 3), identification of Mor1-specific VHHs via phage display (Example 4) or confirmation of Mor1 specificity of these VHHs via ELISA (Example 5).

Example 2

Membrane Preparation of Sf9 Insect Cells Overexpressing Mouse Mor1 and the Pharmacological Characterization of the Recombinant Receptor Membranes containing a functional Mor1 receptor can be prepared from Sf9 cells that express recombinant N-terminally Flag tagged Delta mMor1 (Example 1). To prepare these membranes, freshly grown Sf9 cell cultures are infected at a density of 3E6 cells/ml with 200-fold diluted P2 baculovirus stocks expressing the target gene. Infected cells were cultured for 48 hours or 72 hours at 27° C. (130 rpm) and harvested by centrifugation for 5 minutes at 500×g and room temperature (RT). Cells overexpressing Delta mMor1 were washed twice with ice cold PBS pH7.4 supplemented with 1.5 mM EDTA, pelleted again by centrifugation and stored at −80° C. Overexpression of N-terminally Flag tagged mouse Mor1 (Delta mMor1) on the surface of intact Sf9 cells (48 hours incubation) was monitored via flow cytometry by measuring the specific binding of a FITC-labeled Flag-tag-specific mAb to cells that do not accumulate Topro3.

Figure 2:
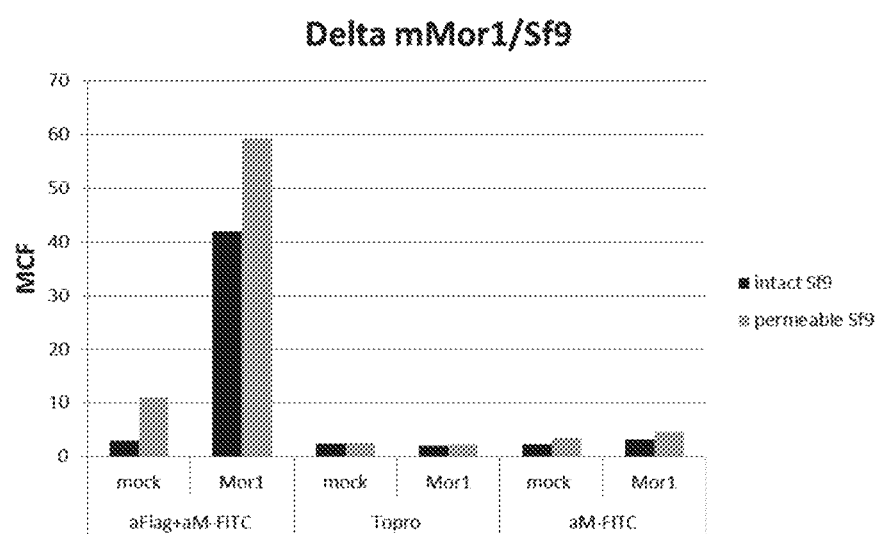
FIG. 2. Expression of recombinant Delta mMor1 in baculovirus-infected Sf9 cells. Mean cell fluorescence values (MCF) are depicted for cells stained with an anti-Flag mouse mAb (aFlag) followed by a secondary anti mouse-FITC conjugate (aM-FITC). Insect cells expressing an untagged (without FLAG) class B GPCR (mock) were stained as negative control. As additional negative controls, background fluorescence detected in the FITC channel was also determined on cells after staining with the secondary mAb alone (aM-FITC) or with Topro3 (Topro) alone.

For flow cytometry experiments, 2.5E5 of freshly harvested Delta mMor1 overexpressing Sf9 cells are transferred to 96-well V-bottom culture plates (Greiner) and are washed with 250 µl of FACS buffer (PBS+10% fetal calf serum). Sf9 cells expressing an irrelevant class B GPCR (mock GPCR) were included as a negative control. After removal of the supernatant, cells are incubated for 1 hour at 4° C. with 100 µl of FACS buffer containing 1 µg anti Flag tag mouse mAb clone M2 (Sigma, cat nr F3165). To remove excess mAb, cells were washed twice with 250 µl of ice cold FACS buffer and the supernatant was removed. Cells were subsequently incubated for minimally 30 minutes at 4° C. with ice cold FACS buffer containing 1 µg of a goat anti-mouse FITC-conjugated secondary detection mAb (eBiosciences, cat nr 11-4011-85). Cells were washed twice with 250 µl of ice cold FACS buffer and supernatant was removed. Immediately before analysis on the flow cytometer, cells were resuspended in 200 µl of ice cold FACS buffer supplemented with 1 µM of Topro3 (Molecular Probes cat nr T3605) to discriminate the intact from the permeable cell population. The mean cell fluorescence intensity (MCF) due to FITC fluorescence was independently gated for the permeable and the intact cell population following Topro3 staining (approximately 50-50 ratio of intact and permeable cells). The cell fluorescence consequent to anti Flag tag detection was calculated for each sample using the FlowJo software (TreeStar Inc., OR, USA) and is depicted in FIG. 2. The MCF of intact or permeable Sf9 cells transfected with Delta mMor1 was significantly higher than the MCF of cells transfected with the mock receptor or of Delta mMor1-infected cells stained only with the secondary antibody. The robust specific signal on intact, non-permeable Delta mMor1 cells confirms the recombinant overexpression of Mor1 at the surface of baculovirus-infected Sf9 cells (FIG. 2).

To prepare membranes containing functional Mor, −80° C. aliquots of 1E7 Delta mMor1 Sf9 cells were resuspended in 1 ml of ice cold 75 mM Tris HCl pH 7.4, 1 mM EDTA, 5 mM MgCl2 and supplemented with leupeptine (10 µg/ml final) and 0.2 mM PMSF protease inhibitors. This cell suspension was homogenized on ice applying six 10-second pulses with a small volume Ultraturrax cell mixer (IKA). The cell homogenate was centrifuged for 35 minutes at 15000×g in a pre-cooled centrifuge. The supernatant was discarded and the membrane pellet was resuspended in 75 mM Tris HCl pH 7.4, 1 mM EDTA, 5 mM $MgCl_2$, 10% sucrose and stored at −80° C. until further use. The total protein content of the membrane prep was determined using the BCA protein assay kit (Thermo Scientific Pierce, cat. nr 23225) according to the manufacturer's instructions. The functionality of the recombinant Delta mMor1, expressed in Sf9 cells (72 hours incubation) was assessed via a radioligand competition assay to verify the native Mor1 folding by measuring specific binding of selective ligands to Mor1.

The pharmacological properties of recombinant Mor1 present in these membrane preparations was assessed in a radioligand competition assay as described by Manglik et al.

(2012) using [3H]-Diprenorphine, a neutral Mor1 antagonist (Perkin Elmer) as the radioligand and increasing concentrations of Dmt1-Dalda (agonist) or Naloxone (antagonist) as cold competitors.

Figure 3:
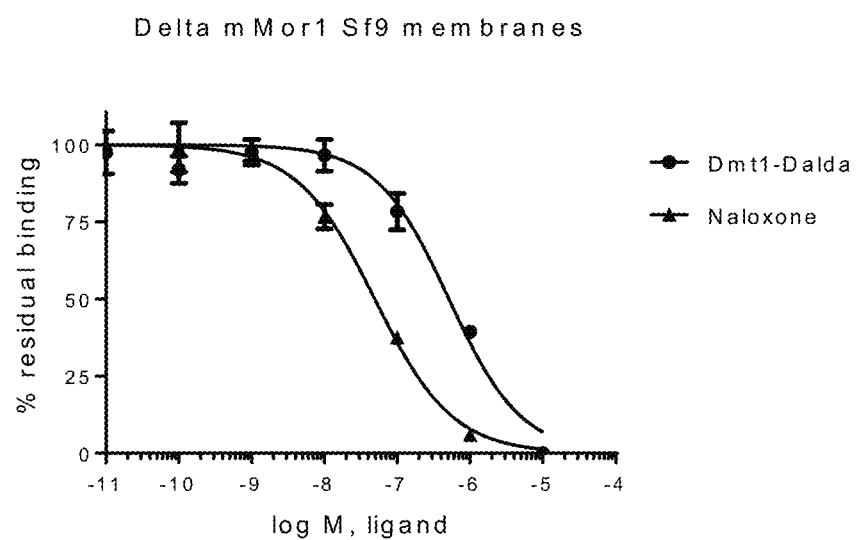
FIG. 3. Functional characterization of recombinant Delta mMor1 in Sf9 insect cells. Dose-dependent binding of Dmt1-Dalda (agonist) or naloxone (antagonist) to membranes derived from Sf9 cells expressing recombinant Delta mMor1 as determined via a radioligand competition assay.

Delta mMor1/Sf9 membranes aliquots containing 7 μg of total protein are diluted in 75 μL TBS (75 mM Tris-HCl pH 7.4, 1 mM EDTA, 5 mM MgCl2, 100 mM NaCl) containing 1% BSA as the binding buffer and transferred to a 96-well plate. Subsequently, a serial dilution of cold competitor agonist Dmt1-Dalda or antagonist Naloxone diluted in 25 μl TBS containing 1% BSA is added. Following, 25 μl TBS containing 1% BSA and 5 nM of [$^3$H]-diprenorphine (final concentration of 1 nM) is added and the reaction mix is incubated for 1 hour at room temperature. Membrane bound [$^3$H]-diprenorphine is separated from unbound radioligand on a 96-well FilterMate harvester (Perkin Elmer) by passing all samples over a Whatman GF/C filter (Perkin Elmer, cat nr 6005174) (presoaked in TBS with 1% BSA). Filters are then washed with cold TBS and subsequently dried for 1 hour at 50° C. After adding 35 μl of a scintillation fluid (MICROSCINT™-O, Perkin Elmer), the radioactivity (cpm) retained on the filters was measured using a Wallac MicroBeta TriLux scintillation counter. FIG. 3 gives the residual radioligand bound (in %) to the receptor in function of increasing concentrations of the cold competing ligand. Each value in the graph represents the average of at least four data points. The IC50 values were determined by nonlinear regression analysis, with the log(agonist) vs response—variable slope (four parameters) equation using Prism (GraphPad Software, San Diego, Calif.). The IC50s of the agonist and antagonist were calculated as 511 nM and 49 nM, respectively, indicating that Dmt1-Dalda and Naloxone specifically interact with membranes containing recombinant Delta mMor1.

Example 3

Induction of a mu-opioid Receptor-specific Humoral Immune Response in Llama and Cloning of the VHH Repertoire All llama immunization experiments were performed according to the European legislation on animal welfare and animal experiments and have been approved by an ethical committee affiliated to the local immunization facility. All llamas were manipulated by experienced veterinary staff.

In order to generate a humoral immune response in llama against the native mu-opioid 1 receptor, three parallel immunization strategies were followed applying different Mor1 immunogens. Llamas Blanco, Jumper and Venus were immunized with purified mouse Mor1 reconstituted in liposomes (truncDelta mMor1, prepared as in Example 1), membranes prepared of CHO cells overexpressing wild-type human Mor1 (WT hMor1/CHO membranes from Perkin Elmer, cat. Nr ES-542-M400UA) and membranes prepared of Sf9 insect cells overexpressing mouse Mor1 (Delta mMor1/Sf9, prepared as in Example 2), respectively.

Figure 4:
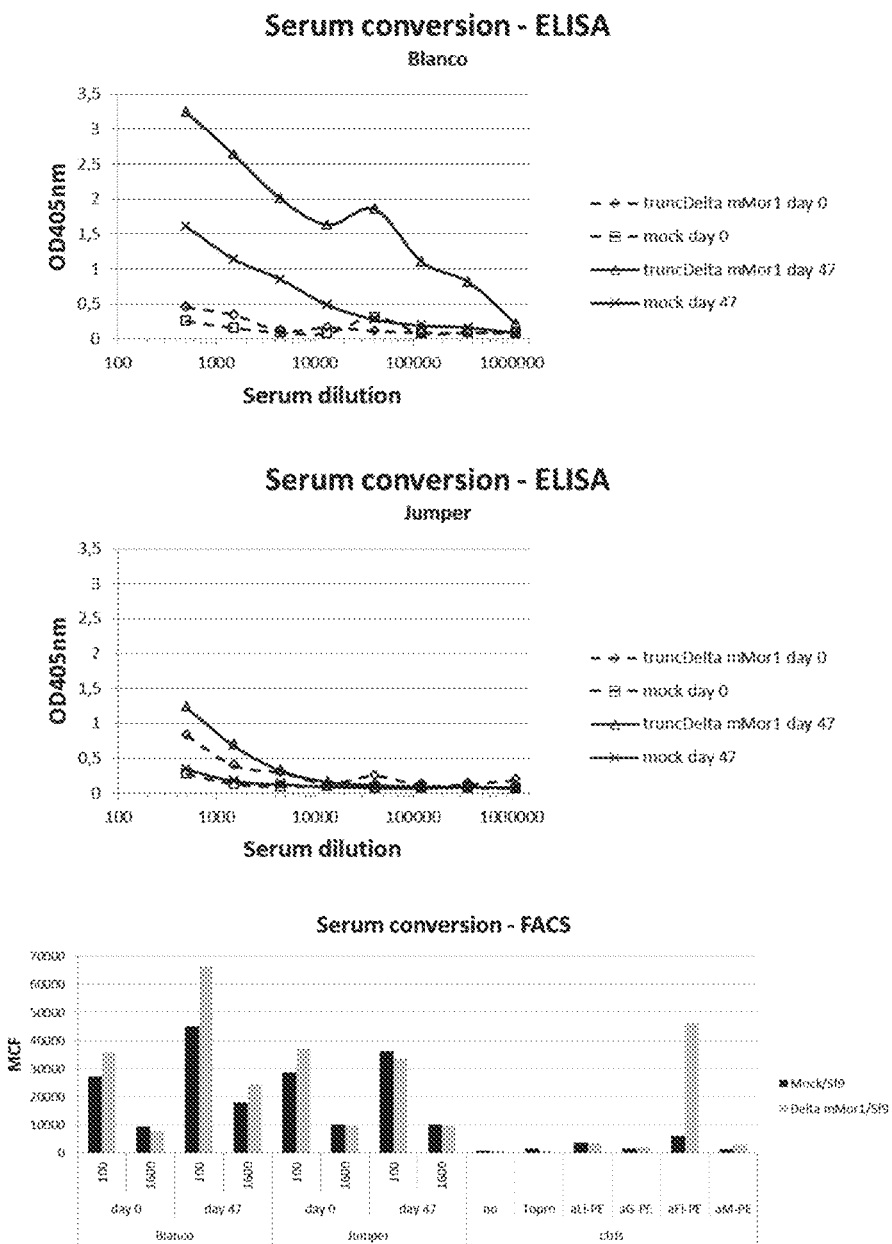
FIG. 4. Mor1-specific serum conversion in llamas Blanco and Jumper upon immunization with TruncDelta mMor1 reconstituted in liposomes or membranes prepared of hMor1/CHO cells, respectively. Serum conversions were analyzed by comparing the mMor1-specific titers of the pre-immune sera (day 0) and immune sera (day 47) by ELISA (top and middle panel) and flow cytometry (bottom panel). As negative control in the ELISA, the absorbance on an irrelevant recombinant GPCR reconstituted in liposomes (mock) was determined. As a positive control for mMor1 expression in flow cytometry, the Flag tagged Delta mMor1/Sf9 cells were stained with an anti-Flag mouse mAb followed by a goat anti-mouse-PE conjugate (aF1-PE). As negative control in flow cytometry, the MCF of an untagged GPCR expressed in Sf9 (Mock/Sf9) was determined. As additional negative controls, background fluorescence detected in the phycoerythrin (PE) compatible channel was determined on non-stained cells (no) and on cells not incubated with llama serum but only stained with the distinct detection reagents: Topro3 (Topro), goat anti-llama IgG followed by anti-goat-PE (aL1-PE), anti-goat-PE (aG-PE) or an anti mouse-PE conjugate (aM-PE).

All llamas were subcutaneously injected with the respective immunogen in intervals of two weeks according to the immunization schedule provided in Table 5. Prior to injection the immunogens were pre-incubated for minimally 1 hour on ice with the high affinity Mor1 agonist Dmt1-Dalda (20-200 μM final) and GTPγS (100 μM final). For llamas Blanco and Jumper, immunogen was separately injected with the adjuvant GERBU LQ at an adjacent but non-overlapping spot near the same draining lymph node. No adjuvant was used for immunization of llama Venus. Pre-immune (collected immediately before the first immunogen administration; day 0) and immune (day 47) serum samples were collected to monitor the serum conversion. To monitor the Mor1-specific serum conversion in llamas Blanco and Jumper, binding of serial dilutions of pre- and post-immune serum samples to truncDelta mMor1 liposomes was assessed via ELISA. For these ELISAs, truncDelta mMor1 liposomes or mock liposomes containing an irrelevant GPCR (100 μl of a 2 μg/ml solution) are solid phase immobilized overnight on a 96-well Maxisorp plate (Nunc) at 4° C. Plates were washed three times with wash buffer (PBS supplemented with 100 nM Dmt1-Dalda). Wells were blocked for 2 hours at RT with 250 μl of 2% PBSM (PBS containing 2% non-fat commercial milk powder; Nestlé) supplemented with 1 μM of Dmt1-Dalda. After three washes in wash buffer, the immobilized liposomes were incubated for 1 hour at RT with serial dilutions of the pre-immune and the immune sera (diluted serum samples were prepared in 100 μL of 0.1% PBSM and 1 μM Dmt1-Dalda). After three wash steps in wash buffer, llama IgGs bound to the immobilized samples were detected using a goat anti-llama-HRP conjugate (100 μl of 1 μg/ml in 0.1% PBSM and 1 μM Dmt1-Dalda). The goat anti-llama_HRP conjugate (Bethyl Laboratories, cat nr A160-100P) binds to the conventional and the heavy chain only IgGs of llama. TMB one solution (Promega, cat nr G7431) was used to develop the colorimetric signal. After 10 minutes of development, the reaction was stopped by adding 100 μl of 1 M H$_2$SO$_4$ and absorbance was measured at OD$_{405\ nm}$. The serum conversion results are depicted in FIG. 4 (upper and middle graph). For llama Blanco —immunized with truncDelta mMor1 liposomes— the signal obtained for the immune serum (day 47) on immobilized truncDelta mMor1 liposomes is systematically higher compared to the signals obtained with the pre-immune serum or on liposomes containing a mock receptor, indicative for a robust Mor1-specific serum conversion (FIG. 4, upper panel). For llama Jumper—immunized with WT hMor1/CHO membranes—the signal obtained for the immune serum (day 47) serum on immobilized truncDelta mMor1 liposomes is minimally two-fold higher compared to the signals obtained with the pre-immune serum or on liposomes containing a mock receptor up to 4.5E3-fold serum dilutions, suggesting a low but Mor1-specific serum conversion (FIG. 4, middle panel).

For llamas Blanco and Jumper, the Mor1-specific serum conversion was also assessed via flow cytometry by comparing the capacity of the pre-immune (day 0) and the immune (day 47) sera to stain Sf9 cells transfected with Delta mMor1. Mock cells, transfected with a mock GPCR were used as a negative control. Sf9 cells were stained with 100 and 1600-fold dilutions of the sera as described in Example 2 (except that bound llama IgG was detected). Bound llama IgG was detected using 1 μg of goat anti-llama IgG (Bethyl Laboratories, cat nr A160-100A-5) in combination with a secondary donkey anti-goat IgG PE conjugate (Jackson ImmunoResearch Labs, cat nr 705-116-147). For llama Blanco, mean fluorescence (only the fluorescence of intact cells that do not accumulate Topro3 was measured) caused by the immune serum (day 47) was significantly higher compared to the signals obtained with the pre-immune serum or on cells expressing a mock (FIG. 4, lowest panel). The fluorescence increase is dose dependent and fluorescence on Delta mMor1>> mock GPCR-infected Sf9 cells, confirming that a humoral immune response is induced to Mor1. No detectable serum conversion is measured in llama Jumper via flow cytometry.

After immunization, the VHH repertoire of each immunized llama was cloned into a phage display vector, resulting in three separate libraries. The display vector allows (after helper phage infection) the production of recombinant phage particles displaying a VHH as a protein III fusion at the tip of the phage but also allows the expression of soluble VHH in the periplasm of E. coli. For the cloning of the VHH repertoire, 100 ml blood was collected five days after the last immunization (day 47) and peripheral blood lymphocytes (PBLs) were separated via density gradient centrifugation using Leucosep tubes (Greiner cat nr 227 288) according to the manufacturer's instructions and as described in Pardon et al. (2014). Total RNA was extracted from PBLs using the RNeasy Midi Kit (Qiagen, cat nr 75142) according to the manufacturer's instructions.

cDNA was synthesized starting from 40-60 µg of total RNA and dN6 random primers using the SuperScript III First-Strand Synthesis System kit (Life Technologies, cat nr 18080-051) following the manufacturer's instructions. Using cDNA as the template, the coding sequences of the VHH repertoire is amplified by RT-PCR via nested PCR as described by Pardon et al. (2014) with minor modifications. Using an adapted primer set, the amplified VHH repertoire was ligated as SfiI-BstEII fragments in phage display vector pXAP100. pXAP100 is similar to pMES4 (genbank GQ907248) but contains a C-terminal His6-cMyc tag and allows cloning of the VHH repertoire via SfiI-BstEII. After electroporation into E. coli TG1 cells, three separate libraries were generated containing 4E8 (Blanco), 4E8 (Jumper) or 1.2E9 (Venus) clones. For each library, the minimal percentage of insert corresponding to the size of a VHH was >91% (evaluated for minimally 23 randomly picked clones per library). Libraries were rescued as described by Pardon et al. (2014) and recombinant phage particles were stored in PBS+20% glycerol at −80° C. until further use.

Example 4

Parallel Panning Approaches to Enrich Mor1-specific VHHs with Distinct Receptor Modulating Behavior Panning experiments were performed on individual libraries. Mor1-specific VHHs are enriched from the immune library by the process of phage display and panning as described by Verheesen and Laeremans (2012).

To identify VHHs selective for the target's active conformation, all incubation and wash steps are performed in presence of saturating amounts of the agonist Dmt1-Dalda to stabilize the receptor in its agonist-bound active-state conformation. Hundred µl of a 10 µg/ml PBS solution containing truncDelta mMor1 liposomes (Example 1) in the presence of 1-10 µM Dmt1-Dalda were solid phase immobilized overnight at 4° C. on a 96-well Maxisorp ELISA plate (Nunc, cat nr 439454). Non-bound liposomes were removed by three wash steps with 250 µl of wash buffer (PBS containing 0.1-1 µM Dmt1-Dalda agonist). Wells were blocked for 2 hours at RT with 250 µl of 2% PBSM (PBS containing 2% non-fat commercial milk powder; Nestlé) supplemented with 1-10 µM of Dmt1-Dalda. After five washes in wash buffer, 1E11 to 1E12 phage particles, diluted in 100 µl of 0.1% PBSM and 1-10 µM Dmt1-Dalda were incubated during 2 hours at RT. To eliminate binders that bind the lipids that reconstitute the liposomes separate Mor1 liposome-coated wells were also incubated with phage solution containing an excess (30 µg/ml) of a mock GPCR reconstituted in liposomes. For both panning conditions, non-bound phage was removed by 20 wash steps in wash buffer. Bound phage was eluted by incubating the wells for 20 minutes at RT with 100 µl of 0.25 mg/ml trypsin solution. To identify VHHs that interact with any Mor1 epitope (independent of an orthosteric ligand), parallel selections were performed under conditions where no Mor1 agonist was added.

Following phage elution, the Mor1-enriched phage subrepertoire is re-infected into E. coli TG1 and titrations are performed to calculate the amount of eluted phage in a particular selection well (allowing to determine Mor1 enrichments; see below). After overnight growth of superinfected TG1 cells to produce phage particles, phage is recovered from the culture supernatant, concentrated and used for a second round of panning following the same enrichment strategies as described above for the first round. After two rounds of panning, 468 individual TG1 clones expressing recombinant VHH were picked for further analysis including sequence analysis of the VHH encoding gene. TG1 clones were only picked from those conditions that show robust enrichment of recombinant phage to the Mor1 liposomes (>10). Mor1 enrichments were calculated as the ratio of the number of eluted phage from a Mor1 containing selection well compared to a parallel well coated with mock liposomes.

Example 5

Screening for Active State Stabilizing VHHs: a FACS-based Binding Assay to Identify Panels of VHHs with Distinct Mor1 Ligand Modulating Behavior We were particularly interested in VHHs that allosterically stabilize the active state of mouse Mor1 by interacting with intracellular Mor1 conformational epitopes -similar to those G-protein mimicking VHHs described by Rasmussen et al. (2011b) and Krüse et al. (2013). Such Nanobodies are expected to increase the affinity of the receptor for agonists and reciprocally, agonists that bind to the receptor increase the affinity for the Nanobody. To identify G-protein mimicking VHHs, we comparatively assessed VHH binding (as crude periplasmic extracts) to Sf9 cells expressing Delta mMor1 cells in presence or absence of Dmt1-Dalda agonist by flow cytometry, including cells expressing a mock receptor as the negative control.

Figure 5:
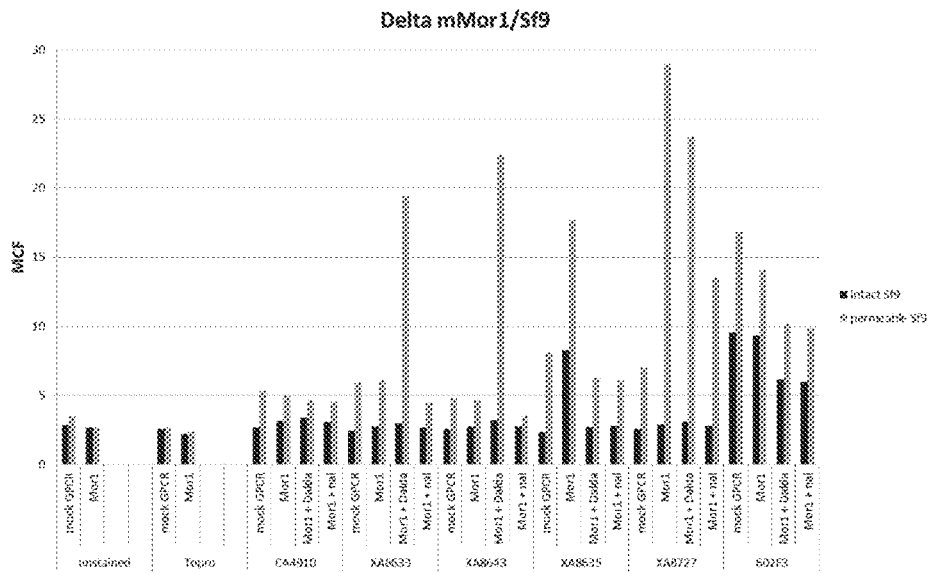
FIG. 5. Screening for Mor1-specific agonist-bound active-state stabilizing Nanobodies by flow cytometry. Delta mMor1-specific Nanobodies that selectively bind the agonist-bound active state of the receptor were identified by comparing the specific binding to Mor1 transfected Sf9 cells in the absence of ligand (Mor1), in the presence of excess Dmt1-Dalda agonist (Mor1+Dalda) or in the presence of excess naloxone antagonist (Mor1+nal). Sf9 cells expressing an irrelevant GPCR were used as negative controls (mock GPCR). To determine whether Nanobodies bind intracellular or extracellular epitopes on Mor1, we compared the mean cell fluorescence values (MCF) caused by FITC fluorescence on intact (intact Sf9) and permeable (permeable Sf9) cell populations. Intact and permeable Sf9 cell populations were determined by Topro3 staining: intact cells do not bind the fluorescent dye Topro3 while permeable cells are stained by Topro3. CA4910 is a (mock) VHH against a non-related GPCR. As additional negative controls, background fluorescence detected in the FITC channel was also determined on cells after staining with Topro3 (Topro) alone or on non-stained cells.

For the preparation of periplasmic extracts, clones encoding monoclonal VHHs are grown separately in 96 deepwell plates containing 1 ml of selective liquid culture (2×TY containing 100 µg/ml ampicillin) and VHH expression was induced as described in Pardon et al. (2014). VHHs are expressed as a soluble His6-cMyc-tagged protein in the periplasm of the TG1 cells. For the flow cytometry assay, 2.5E5 of freshly harvested Delta mMor1/Sf9 or mock GPCR overexpressing Sf9 cells are transferred to 96-well V-bottom culture plates (Greiner, cat nr 651101) and are washed with 250 µl of FACS buffer (PBS+10% fetal calf serum). For VHH binding, cells are incubated for 1 hour at 4° C. with 100 µl of FACS buffer containing five-fold diluted periplasm—premixed for 30 minutes at 4° C. with 1 µg of anti c-Myc tag detection mouse mAb clone 9E10 (Roche, cat nr 11 667 203 001)—and 20 µM of Mor1 ligand. For each periplasmic extract, four parallel incubation conditions are assessed: Delta mMor1/Sf9 cells+Dmt1-Dalda agonist (condition 1); Delta mMor1/Sf9 cells+naloxone antagonist (condition 2); Delta mMor1/Sf9 cells without any ligand (condition 3); mock GPCR expressing Sf9 cells without any ligand (condition 4). After VHH binding, cells were washed twice with 250 µl of ice cold FACS buffer with or without excess of ligand. For those conditions where ligand was applied, the wash buffer was supplemented each time with 2 µM of the corresponding ligand. For fluorescent staining, cells were subsequently incubated for minimally 30 minutes at 4° C. with ice cold FACS buffer containing 1 µg of a goat anti-mouse FITC-conjugated secondary detection mAb in presence/absence of 20 µM of the appropriate Mor1 ligand. Cells were washed twice with 250 µl of the appropriate wash buffer (FACS buffer +/−2 µM of corresponding ligand). Immediately before analysis of VHH binding in the flow cytometer, cells were resuspended in 200 µl of ice cold FACS buffer containing 1 µM of Topro3 (Molecular Probes cat nr T3605) in presence/absence of 20 µM of the appropriate Mor1 ligand. Using the FlowJo software, the mean cell fluorescence intensity (MCF) caused by VHH binding (FITC fluorescence) was independently gated for the permeable and the intact cell population for each of the four parallel conditions. The MCF values of those VHH clones that show specific interaction with Delta mMor1 and have a distinct AA sequence are represented in FIG. 5, upper panel.

Based on this analysis, we discriminate three groups of VHHs. The first group of VHHs ("Profile I") only show significant binding to the Mor1 expressing insect cells (and showing low-background-fluorescence signal on mock GPCR expressing Sf9) in excess of agonist. These are candidate active state stabilizing VHHs (XA8633, XA8639, XA8641 and XA8643). The typical MCF profile for two of these VHHs (XA8633 and XA8643) is shown in FIG. 5. Topro3 mediated gating of the permeable/intact cell population indicates that these VHHs interact with intracellular epitopes: only a Mor1-specific signal is detected on permeable cells (grey bars; in presence of agonist) but not on intact cells (black bars; in presence of agonist). Following sequence analysis, we identified four VHHs belonging to "profile I" and showing a distinct AA sequence. They all belong to the same sequence family but differ in sequence. A VHH sequence family is defined as a group of antibody fragments with a highly similar CDR3 AA sequence (identical length and >80% sequence identity). VHHs belonging to the same sequence family derive from the same B-cell lineage and are anticipated to interact with a similar epitope. All these "Profile I"-VHHs are candidate G-protein mimicking VHHs since they i) show only robust Mor1 binding in presence of agonist and ii) interact with intracellular Mor1 epitopes. An AA sequence alignment of all unique Mor1 VHHs of Profile I is provided in FIG. 7.

Besides the identification of G-protein mimicking VHHs, this screening assay enables the identification of a highly diverse panel of Mor1-specific VHHs with other ligand modulating effects or even simple binders that do not affect receptor function or conformation. "Profile II" is exemplified by XA8635 (FIG. 5): this VHH interacts with the extracellular part of the receptor and is displaced by both an agonistic or antagonistic ligand. After sequence analysis of all Mor1 binders, several clones belonging to "Profile II" were identified, all with the same unique AA sequence (FIG. 7). Clones with "Profile III" like XA8727 interact with the intracellular part of Mor1 (no Mor1-specific signal on intact Mor1 cells) and still show significant binding in presence of agonist or antagonist (FIG. 5). Following sequence analysis, clones belonging to "Profile III" all showed the same unique AA sequence (FIG. 7).

As a parallel method to identify Mor1-specific VHHs, detergent-soluble opioid receptor—reconstituted in liposomes—was used for phage display selections. Selections were performed on library Blanco in presence of excess amounts of Dmt1-Dalda and monoclonal VHHs were assessed for Mor1 specificity via flow cytometry similarly as described in this example. Once more, "Profile I" VHHs were identified belonging to the same sequence family as XA8633. Additionally, a new "Profile III" VHH was identified belonging to a new sequence family (XA9644, SEQ ID NO: 74).

As an alternative approach to assess Mor1 specificity, periplasmic extracts of VHHs were assessed for binding to truncDelta mMor1 reconstituted in liposomes via ELISA. All VHH AA sequence variants that were identified as Mor1-specific clones via flow cytometry were tested and confirmed to bind Mor1 in ELISA: XA8633, XA8639, XA8641 and XA8643 (Profile I), XA8635 (Profile II) and XA8727 (Profile III).

Figure 6:
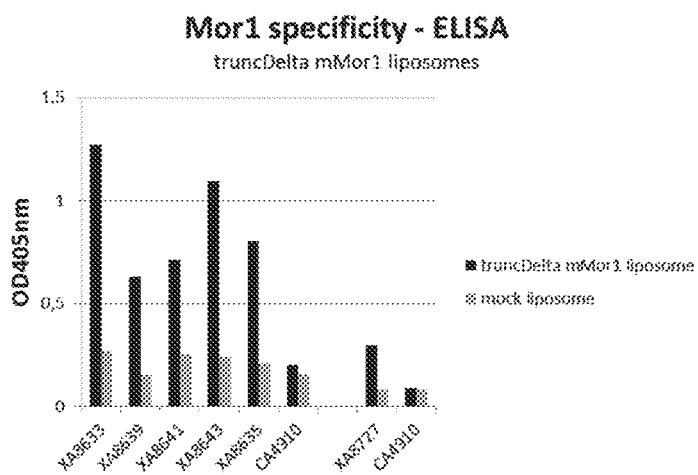
FIG. 6. Screening for Mor1-specific Nanobodies. Mor1-specific Nanobodies were identified by ELISA by comparing the binding of the antibodies to recombinant mMOR1 reconstituted in liposomes (truncDelta mMor1 liposome) and to an irrelevant recombinant GPCR reconstituted in liposomes (mock liposome). CA4910 is a Nanobody that binds an unrelated GPCR (see as in FIG. 5) and was used as a negative control. The absorbance values of the VHHs tested were assembled into one graph but originate from two different experiments each with a slightly different absorbance value for the negative control CA4910: XA8633, XA8639, XA8641, XA8643 and XA8635 (tested in experiment 1) and XA8727 (tested in experiment 2). The absorbance value for CA4910 corresponding to experiment 1 and 2 is represented immediately right of the VHHs tested in that particular experiment.

For the ELISA, truncDelta mMor1 liposomes or mock liposomes (100 µl of a 2 µg/ml solution supplemented with 10 µM of Dmt1-Dalda) are solid phase immobilized overnight in a 96-well Maxisorp plate at 4° C. Plates were washed three times with wash buffer (PBS supplemented with 1 µM Dmt1-Dalda). Wells were blocked for 2 hours at RT with 250 µl of 2% PBSM (PBS containing 2% non-fat commercial milk powder; Nestlé) supplemented with 10 µM of Dmt1-Dalda. After three washes in wash buffer, 100 µl of five-fold diluted periplasm containing the VHHs in 0.1% PBSM (PBS containing 0.1% non-fat commercial milk powder; Nestlé) and 10 µM Dmt1-Dalda was incubated during 1 hour at RT. After three additional wash steps in wash buffer, bound VHHs were detected using a primary anti-cMyc mAb followed by a secondary goat anti-mouse-AP conjugate (both 100 µl of 1 µg/ml in 0.1% PBSM and 10 µM Dmt1-Dalda) incubation. DNPP (Sigma, cat nr 71768) was used to develop the colorimetric signal. Absorbance was measured at OD405 nm and results are depicted in FIG. 6. Absorbance values for all VHHs tested are minimally three-fold higher on truncDelta mMor1 liposomes compared to the mock liposomes, strongly indicating that all tested VHHs specifically bind to Mor1. All VHHs tested confirm specific binding to truncDelta mMor1 reconstituted in liposomes. As truncDelta mMor1 is truncated at its N- and C-terminus, most likely these VHHs interact with extracellular or intracellular Mor1 conformational epitopes.

Display vector pXAP100 permits the inducible periplasmic expression of VHHs as a soluble C-terminally His6-cMyc tagged protein in the periplasm of E. coli strain WK6 without the need for recloning. For further characterization, VHHs expression constructs are transformed to E. coli WK6 and the VHHs purified by immobilized metal affinity chromatography (IMAC). Cultures are grown in baffled flasks to OD600=0.5-1 at 37° C. in TB medium containing 0.1% glucose and 100 µg/ml ampicillin. One tenth volume of TB medium is added containing 100 µg/ml ampicillin and 10 mM IPTG (final concentration of 1 mM). VHHs are purified by IMAC, using Talon beads (Clontech) according to the manufacturer's protocol. Next, purified proteins are dialyzed against PBS and spin concentrated. For all VHHs, the purity was ≥90% as judged by SDS-PAGE and subsequent Coomassie staining.

Example 6

VHHs of "Profile I" Stabilize the Agonist-bound Active-state of Mor1

Figure 8:
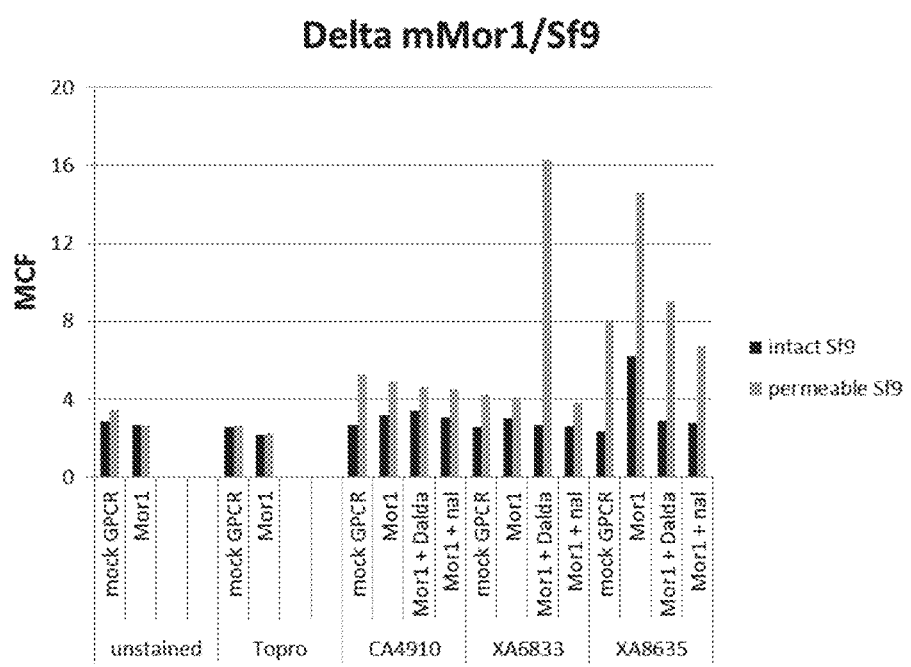
FIG. 8. Binding properties of the purified Mor1-specific VHHs XA8633 and XA8635 in flow cytometry. The specificities of purified XA8633 and XA8635 were confirmed in flow cytometry by comparing their binding to Delta mMor1 transfected sf9 cells in the absence of ligand (Mor1), in the presence of excess Dmt1 Dalda agonist (Mor1+Dalda) or in the presence of excess naloxone antagonist (Mor1+nal). To identify if they bind intracellular or extracellular epitopes, we compared the mean cell fluorescence values (MCF) of intact Sf9 cells that do not accumulate fluorescent dye Topro (intact cells) with the population of cells that accumulate Topro (permeable Sf9). CA4910 is a (mock) Nanobody against a non-related GPCR. To determine the ratio of intact versus permeable cells, transfected SD cells were stained separately with Topro3 dye alone (Topro).

Following purification, binding of 1 µM of XA8633 to cell surface expressed Mor1 (Delta mMor1/Sf9) was assessed by flow cytometry exactly as described in Example 5, except that not the periplasmic extract was incubated but purified XA8633 was added. Using purified XA8633, an identical fluorescence profile is detected (FIG. 8) compared to the one obtained with periplasm (FIG. 5). VHHs that allosterically stabilize the active state of mouse Mor1 by interacting with intracellular Mor1 conformational epitopes—similar to those G-protein mimicking VHHs as described by Rasmussen et al. (2011b) and Krüse et al. (2013)—are expected to increase the affinity of the receptor for agonists.

Figure 9:
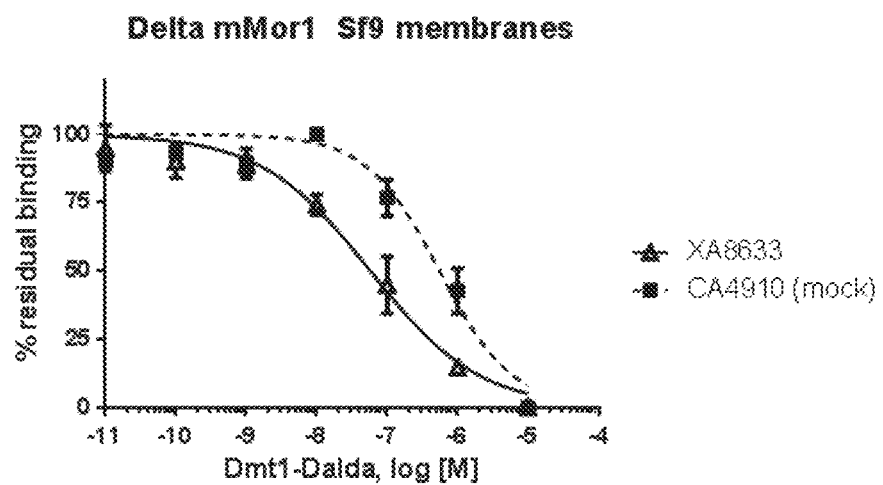
FIG. 9. Similar to G proteins, Nanobody XA8633 causes a substantial enhancement of Dmt1-Dalda affinity to Mor1 in radioligand competition binding assays. The effect of XA8633 on the affinity of agonists for recombinant Delta mMor1 was measured by monitoring the residual binding of the radiolabeled antagonist at increasing Dmt1-Dalda concentrations. CA4910, a Nanobody that binds an unrelated GPCR was used as a negative control. IC50 values obtained with VHH XA8633 and mock VHH CA4910 are 57 and 550 nM, respectively, under the conditions tested.

To further confirm that the VHHs, belonging to "Profile I," are able to stabilize the agonist-bound active-state of the Mor1, we performed radioligand competition assays as described by Rasmussen et al. (2011b) and Kruse et al. (2013) to confirm that binding of XA8633 to Mor1 increases the affinity of the receptor for the MOR agonist Dmt1-Dalda. To analyze the pharmacological properties of the MOR1-XA8633 complex, Delta mMor1/Sf9 membranes were pre-incubated with excess of purified VHH, a single concentration of antagonistic radioligand [3H]-Diprenorphine (a neutral Mor1 antagonist), and a dilution series of the well-characterized Mor1 agonist as the competitor (Dmt1-Dalda). In a volume of 75 µl, 8.33 µM of VHH is pre-incubated with 7 µg of Sf9/mouse delta mMor1 membranes for 30 minutes at RT in TBS (75 mM Tris-HCl pH 7.4, 1 mM EDTA, 5 mM MgCl2, 100 mM NaCl) containing 1% BSA as the binding buffer. Next, 25 µl binding buffer containing a serial dilution of cold agonist competitor Dmt1-Dalda (ranging from $10^{-12}$ to $10^{-5}$ M) is added. Following, five nM [$^3$H]-diprenorphine of radioligand in 25 µl binding buffer (1 nM final concentration) is added and the reaction mix is incubated for 1 hour at room temperature. Receptor bound [$^3$H]-diprenorphine is separated from unbound radioligand on 96-well FilterMate harvester by passing all samples over a Whatman GF/C filter (presoaked in TBS with 1% BSA) and washed in cold TBS. Filters were prepared and cpms were measured as described in Example 2. The percentage of residual radioligand binding in presence of the candidate active state stabilizing Nanobody XA8633 vs a mock VHH is calculated and represented in FIG. 9. Data on the graph represent the mean±s.e. of each value (average of three datapoints). The IC50 values were determined by nonlinear regression analysis, with the log(agonist) vs response—variable slope (four parameters) equation using Prism (GraphPad Software, San Diego, Calif.). In presence of XA8633 or a mock VHH (CA4910), the calculated IC50s are 5.7E-8 and 5.5E-7 M, respectively. In presence of 5 µM XA8633, the IC50 of Mor1 agonist Dmt1-Dalda is approximately ten-fold decreased (leftward shifted) compared to a mock VHH CA4910, demonstrating that XA8633 increases the affinity of Dmt1-Dalda agonist for its receptor. XA8633 thus stabilizes the agonist-bound active state of the Mor1 receptor.

Example 7

"Profile II"-VHHs Displace Orthosteric Ligands Bound to mu-opioid Receptor

As for the "Profile-I" VHHs, binding of 1 µM purified XA8635 (Profile II) to cell surface expressed Mor1 (Delta mMor1/Sf9) was assessed by flow cytometry, described in Example 6. Also for purified XA8635, an identical fluorescence profile is detected (FIG. 8) compared to the one obtained with periplasm (FIG. 5). In presence of Mor1 ligand (agonist or antagonist), XA8635 loses its ability to specifically bind to intact and permeable Sf9 cells overexpressing Mor1, suggesting that XA8635 is an inhibitor of Mor1 signaling by preventing binding of ligand to the orthosteric pocket.

Figure 10:
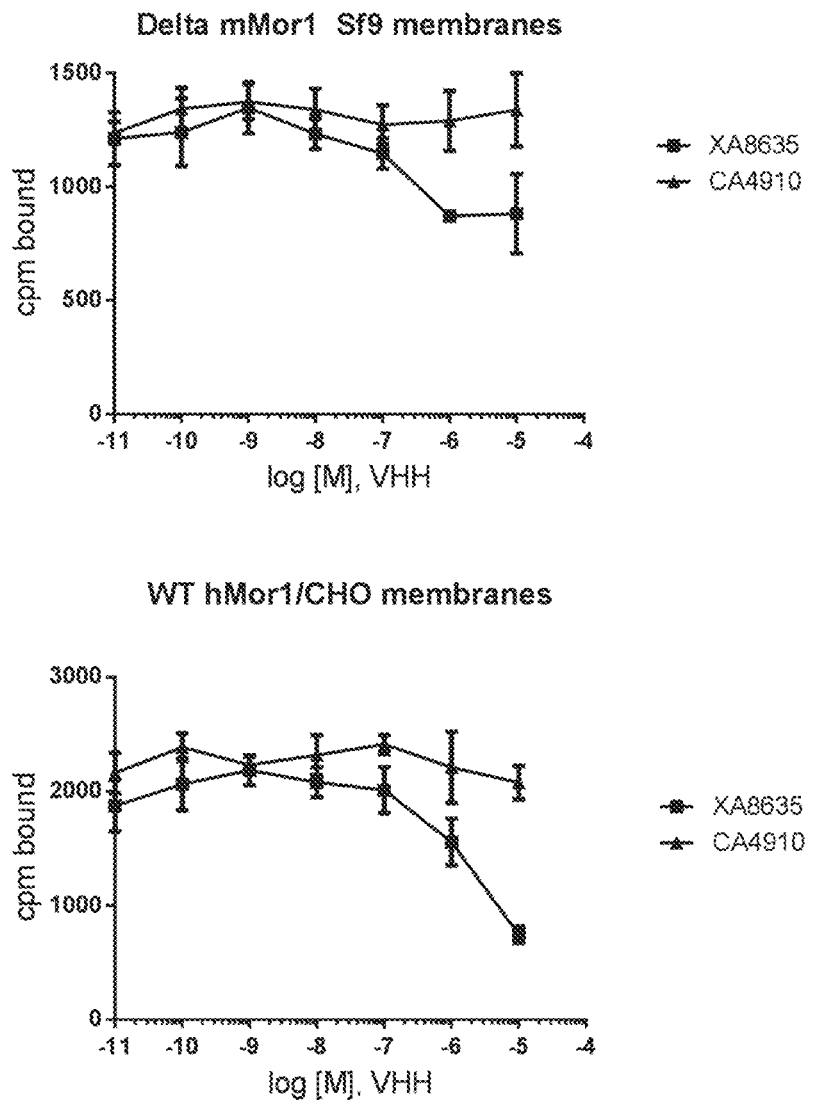
FIG. 10. Radioligand displacement of dose-dependent XA8635 (or mock VHH CA4910) on membranes derived of mouse or human Mor1 overexpressing Sf9 cells.

A radioligand competition assay was performed as described in Example 6 with minor modifications: 5 µg of WT human hMor1/CHO membranes or 7 µg of Delta mMor1/Sf9 membranes were incubated with a concentration range of purified XA8635 and 1 nM of the radioligand (no agonist was added). The mixture was incubated for 1 hour at RT and after washing, filter bound radioligand was measured. A dose-dependent increase in radioligand displacement is demonstrated for XA8635 on both membrane types (FIG. 10), indicating that this VHH interacts both with the human and mouse Mor1 orthologue and confirms once more that this VHH prevents binding of ligand to the orthosteric pocket.

Example 8

Bivalent XA8635 and Cross-reactivity with Human Mor1

A bivalent XA8635 expression construct was generated by making a genetic head to tail fusion of XA8635, separated by a 9GS linker (Table 2). XA8635 was reamplified using the display construct pXAP100 harboring XA8635 cDNA as template. Primer set XAP1-FW-MfeI and VHH1-Rv-BamHI was used to amplify the N-terminal VHH while the combination VHH2-FW-BamHI and VHH2-Rv-BstEII for C-terminal VHH amplification (Table 6). Appropriate restriction enzyme recognition sequences are introduced into the individual primers to clone the N- and C-terminal VHH as an MfeI-BamHI and BamHI-BstEII fragment, respectively, in MfeI-BstEII digested expression vector. The primers VHH1-Rv-BamHI and VHH2-FW-BamHI incorporate the coding sequence for the GS linker after BamHI digestion. To amplify both VHH fragments, 5 ng of template and standard PCR reagents were used in the following amplification reaction: 2 minutes at 94° C., 25 cycles of [30 seconds at 94° C., 30 seconds at 55° C., 1 minute at 72° C.] and 7 minutes at 94° C. Amplicons are purified using the Wizard SV Gel and PCR Clean-up System (Promega, cat nr A9282) according to the manufacturer's instructions and were subsequently double digested with the appropriate set of enzymes. The digested and purified insert and vector fragments were ligated in a single ligation mixture, resulting in construct XA8635-9GS-XA8635. The ligation was subsequently transformed into E. coli WK6 and sequence analysis allowed to identify correct bivalent XA8635. The vector backbone allows expression of soluble XA8635-9GS-XA8635 containing a cMyc-His6 tag at the C-terminus. The bivalent VHH was expressed and purified as described in Example 5, resulting in 9.9 mg of purified protein with purity >95% purity (Coomassie staining) from a 3-L culture after single IMAC purification step. Binding of mono and bivalent XA8635 was assessed via flow cytometry on Mor overexpressing CHO cells vs parental non-transfected CHO cells, similarly as described in Example 5 (but in absence of any Mor1 ligand). A dose-dependent specific binding to Mor overexpressing CHO cells is demonstrated for mono- and bivalent XA8635, confirming in a separate assay that XA8635 is cross-reactive to human and mouse Mor1 orthologues. At 1 µM, bivalent XA8635 showed approximately 34% increased fluorescence versus monovalent XA8635 (FIG. 11).

Example 9

The "Profile I" VHH XA8639 is a G-protein Mimetic and Enables the Solution of High Resolution Structure of the Agonist Bound Active State mu-opioid Receptor-XA8639-BU72 Complex by X-ray Crystallography Active states of many ligand-activated GPC s are relatively unstable, even when bound to full agonists. Active states can be stabilized by interactions of the GPCR with its cognate G protein. This stabilization is reflected in a higher affinity for agonists when GPCRs are in complex with their cognate G protein. In the case of Mor1, agonist affinity is enhanced by 220-fold when coupled to the G protein Gi (FIG. 12 upper panel), indicating a stabilization of active state Mor1 receptor conformation. The ability of XA8639 to stabilize the high affinity state for Mor1 agonists was examined.

Purified Mor1 was reconstituted into high-density lipoprotein (HDL) particles comprised of apolipoprotein Al and POPC/POPG (Avanti Polar Lipids) lipid mixture in a 3:2 molar ratio and agonist competition assays were performed in the presence or absence of nanobody. In the competition assay, 0.02 nM functional receptor and 2.3 nM [$^3$H] Diprenorphine (DPN) were mixed in binding buffer (100 mM NaCl, 25 mM HEPES 7.4, 0.1% BSA) with indicated concentration of BU72 and XA8639 or G protein. Heterotrimeric Gi was prepared by co-expressing human G$\alpha$i1, human G$\beta$1 and G$\gamma$2 subunits in HighFive insect cells using baculovirus system (Expression System). The G protein was purified as previously described (Rasmussen 2011b). Reactions were incubated for 4 hours at room temperature before being filtered by a 48-well harvester (Brandel) onto a filter paper that was treated with 0.1% polyethylenimine. Radioligand activity was measured by liquid scintillation counting. Data was processed and analyzed by Prism (GraphPad Software).

In the presence of 5 μM nanobody XA8639, the inhibition constant (Ki) of BU72 shifts from 1.5 nM to 8.5 pM (FIG. 12, lower panel). Thus, XA8639 enhances affinity for BU72 by 176-fold, comparable to the enhancement observed with Gi.

To improve the quality of purified Mor1 for agonist-Mor1-XA8639 complex crystal formation, a functional selection was performed using "Profile II" XA8635 that binds to the extracellular surface and extends into the orthosteric binding pocket. Ligand-free Mor1 was mixed with 1:2.5-fold stoichiometric excess of XA8635, which binds to the receptor with high affinity (Ki of approximately 12 nM). XA8635 bound receptor was re-loaded to nickel resin and washed with 20 mM imidazole supplemented ligand-free buffer. Functional Mor1-XA8635 complexes were eluted with buffer containing 250 mM imidazole, 0.01% MNG, 0.001% cholesterol hemisuccinate, 25 mM HEPES pH 7.5 and 100 mM NaCl. BU72 and XA8639 were then added in excess. BU72 displaced XA8635 and a BU72-MOR-XA8639 complex was formed. The mixture was concentrated and subjected to size exclusion chromatography to separate the BU72-MOR-XA8639 complex from free XA8635 and XA8639. The purified complex was concentrated to approximately 50 mg/mL before crystallization trials.

To crystallize the active state of Mor1, efforts to obtain a structure of the Mor1-Gi complex have not been successful. An alternative to G protein stabilization has been the use of G protein mimetic nanobodies (camelid variable domain antibody fragments). Purified Mor1 was reconstituted into 10:1 mixture of monoolein and cholesterol (w:w, Sigma) by combining the protein solution (50 mg/ml) and lipid in a 1:1.5 ratio (w:w). Protein and lipid were loaded into glass syringes (Art Robbins Instruments) and mixed until homogeneous. 30 nL of samples was dispensed onto 96-well glass plates and overlaid with 500 nL precipitant solution using a Gryphon LCP robot (Art Robbins Instruments). Crystals grew in a mixture of 15-25% PEG300, 0.1 M HEPES pH 7.0-7.5, 1% 1,2,3-heptanetriol, 0.5-1.0% Polyethylene glycol 400 (Hampton Research) and 0.1-0.3 M $(NH_4)_2HPO_4$. Crystals were observed after 2 days and reached full size in 1 week. Crystals were harvested with mesh grid loops (MiTeGen) and flash frozen in liquid nitrogen. Loops were screened at Advanced Photon Source GM/CA beamlines 23ID-B and 23ID-D. Data were collected using a 10 μm beam with 5% attenuation and exposed for 0.5-1 second. An oscillation width of 0.1-0.5 degree was used and diffraction images from four crystals were merged to create the final data sets.

Crystals of the Mor1 bound to Bu72 and Nb39 were obtained in a monoolein mesophase, a lipid medium that mimics a lipid bilayer. A complete data set to 2.1 Å was obtained by merging diffraction data from four crystals, and the structure was determined by molecular replacement using the inactive MOR and a nanobody as search models. Diffraction images were scaled and processed by XDS (W. Kabsch et al., 2010). The structure was determined by molecular replacement with the structure of inactive MOR (Protein Data Bank accession 4DKL) and Nb80 (Protein Data Bank accession 3P0G) as searching models in Phaser (McCoy et al., 2007). The model was rebuilt in Coot (Emsley et al., 2004) and refined using Phenix (Afonine 2012) to a resolution of 2.1 Å and the figures were prepared using PyMol.

As expected, XA8639 binds to the intracellular surface (FIG. 13). In the crystal lattice, XA8639 mediates the majority of packing interactions between layers and adjacent XA8639-Mor1 complexes, there are no packing interactions involving the extracellular surface (data not shown). A weak dimeric packing interaction was observed (buried surface area of 460 Å$^2$) involving the extracellular end of first transmembrane (TM) helice 1 (TM1), TM2 and the first extracellular loop (ECL1). This contrasts with the more extensive parallel dimer interaction (1460 Å$^2$) involving TM5 and TM6 observed in the crystal structure of the inactive state. It is of interest, that the dimeric interaction observed in the inactive structure would not be compatible with the conformational changes observed in the active state.

XA8639 does not penetrate as deeply into the core of the Mor1 when compared with the Nb80-β2AR complex and the Nb9-8-M2R complex (Kruse et al., 2013; Rasmussen et al., 2011b). XA8639 interacts primarily through hydrogen bonds with residues from ICL2, ICL3 and ICL4 of the Mor1. Unlike Nb80 and Nb9-8, which stabilize the active state primarily through interactions with their complementarity-determining regions (CDRs), there are more extensive interactions of the Mor1 with the framework of XA8639, with only a small contribution from CDR2 and CDR3 (FIG. 13).

Structural differences between inactive and active Mor1 on the extracellular surface are relatively small, with the exception of the proximal N-terminus. Conformational changes at the cytoplasmic surface of the Mor1 observed upon activation are similar to those observed for the β2AR, M2R and rhodopsin, with large outward movement of TM6, a smaller outward movement of TM5 and an inward movement of TM7. The conserved DRY motif at the intracellular end of TM3 plays a role in maintaining GPCRs in the inactive state. Interactions with these conserved amino acids in the active state are less well conserved than are interactions with NPxxY. In rhodopsin, ERY maintains rhodopsin in an inactive conformation through an ionic interaction with $E247^{6.30}$ in TM6. In the inactive state of Mor1, $R165^{3.50}$ forms a hydrogen bond with $Y252^{5.58}$, stabilizing the inward movement of TM5, similar to what is observed for the M2R, the β2AR-Gs complex and metarhodopsin II.

TABLE 2

List of VHH AA sequences.

| Nanobody reference number | SEQ ID NO: | AMINO ACID SEQUENCE |
| --- | --- | --- |
| XA8633 (=598H7) | 1 | QVQLVESGGGLVRPGGSRRLSCVDSERTSYPMGWFRRAP GKEREFVASITWSGIDPTYADSVADRFTISRDVANNTLYL QMNSLKHEDTAVYYCAARAPVGQSSSPYDYDYWGQGT QVTVSSAAAHHHHHHGAAEQKLISEEDLNGAA |
| XA8639 (=598A7) | 2 | QVQLVESGGGLVRPGGSLRLSCVDSERTSYPMGWFRRAP GKEREFVASITWSGIDPTYADSVADRFTTSRDVANNTLYL QMNSLKHEDTAVYYCAARAPVGQSSSPYDYDYWGQGT QVTVSSAAAHHHHHHGAAEQKLISEEDLNGAA |
| XA8641 (=598A2) | 3 | QVQLVESGGGLVRPGGSLRLSCVDSGRTSYPMGWFRRAP GKEREFVASITWSGIDPTYADSVADRFTISRDVANNTLYL QMNSLKHEDTAVYYCAARAPVGQSSSPYDYDYWGQGT QVTVSSAAAHHHHHHGAAEQKLISEEDLNGAA |
| XA8643 (=598G11) | 4 | QVQLVESGGGLVRPGGSLRLSCVDSERTSYPMGWFRRAP GKEREFVASITWSGIDPTYADSVADRFTISRDVANNTLYL QMNSLKHEDTAVYYCAARAPVGQSSSPYDYDYWGQGT QVTVSSAAAHHHHHHGAAEQKLISEEDLNGAA |
| XA8635 (=601H10) | 5 | QVQLVESGGGLVQAGGSLRLSCAASGSISSISTMGWYRQ APGNERELVAAITSGGSTNYADSVKGRFTISRDNAKNTV YLQMNSLKPEDTAVYYCNEKYYSGSYFYKSEYDYWGQG TQVTVSSAAAHHHHHHGAAEQKLISEEDLNGAA |
| XA8727 (=599D2) | 6 | QVQLVESGGGLVQAGGSLRLSCAASGETEDDYAIAWERQ APGKEREGVSCISSSDGSTYYADSVKGRFTISNDNAKNTV YLQMNSLKPEDTAVYYCADLSRSCGRGYRYLEVWGQ GTQVTVSSAAAHHHHHHGAAEQKLISEEDLNGAA |
| Biv XA8635 | 49 | QVQLVESGGGLVQAGGSLRLSCAASGSISSISTMGWYRQ APGNERELVAAITSGGSTNYADSVKGRFTISRDNAKNTV YLQMNSLKPEDTAVYYCNEKYYSGSYFYKSEYDYWGQG TQVTVSSGGGGSGGGSQVQLQESGGGLVQAGGSLRLSC AASGSISSISTMGWYRQAPGNERELVAAITSGGSTNYADS VKGRFTISRDNAKNTVYLQMNSLKPEDTAVYYCNFKYY SGSYFYKSEYDYWGQGTQVTVSSAAAEQKLISEEDLNGA AHHHHHH |
| XA9644 | 74 | QVQLVESGGGLVQAGGSLRLSCVASGSIFSISAMGWYRQ APGKQRELVATITSGGTTNYADSVKGRFTISGDTAKNMV YLQMSSLKPEDTAVYYCAADMEVWDYTDGDDDDYWG QGTQVTVSSAAAHHHHHHGAAEQKLISEEDLNGAA |

TABLE 3

FRs and CDRs of MOR1 Nanobodies.

| Nanobody reference number | SEQ ID NO: | FR1 | SEQ ID NO: | CDR1 | SEQ ID NO: | FR2 | SEQ ID NO: | CDR2 | SEQ ID NO: | FR3 | SEQ ID NO: | CDR3 | SEQ ID NO: | FR4 |
|---|---|---|---|---|---|---|---|---|---|---|---|---|---|---|
| XA8633 | 1 | QVQLVES GGGLVRP GGSRRLSC VDS | 7 | ERTSYP | 13 | MGWFRR APGKEREF VAS | 19 | ITWSGIDP | 25 | TYADSVA DRFTISRD VANNTLYL QMNSLKH EDTAVYYC | 31 | AARAPVG QSSSPYDY DY | 37 | WGQGTQ VTVSSAAA HHHHHH GAAEQKLI SEEDLNGA A | 43 |
| XA8639 | 2 | QVQLVES GGGLVRP GGSLRLSC VDS | 8 | ERTSYP | 14 | MGWFRR APGKEREF VAS | 20 | ITWSGIDP | 26 | TYADSVA DRFTISRD VANNTLYL QMNSLKH EDTAVYYC | 32 | AARAPVG QSSSPYDY DY | 38 | WGQGTQ VTVSSAAA HHHHHH GAAEQKLI SEEDLNGA A | 44 |
| XA8641 | 3 | QVQLVES GGGLVRP GGSLRLSC VDS | 9 | GRTSYP | 15 | MGWFRR APGKEREF VAS | 21 | ITWSGIDP | 27 | TYADSVA DRFTISRD VANNTLYL QMNSLKH EDTAVYYC | 33 | AARAPVG QSSSPYDY DY | 39 | WGQGTQ VTVSSAAA HHHHHH GAAEQKLI SEEDLNGA A | 45 |
| X8643 | 4 | QVQLVES GGGLVRP GGSLRLSC VDS | 10 | ERTSYP | 16 | MGWFRR APGKEREF VAS | 22 | ITWSGIDP | 28 | TYADSVA DRFTISRD VANNTLYL QMNSLKH EDTAVYYC | 34 | AARAPVG QSSSPYDY DY | 40 | WGQGTQ VTVSSAAA HHHHHH GAAEQKLI SEEDLNGA A | 46 |
| XA8635 | 5 | QVQLVES GGGLVQA GGSLRLSC AAS | 11 | GSISSIST | 17 | MGWYRQ APGNERE LVAA | 23 | ITSGGST | 29 | NYADSVK GRFTISRD NAKNTVY LQMNSLK PEDTAVYY C | 35 | NFKYYSGS YFYKSEYD Y | 41 | WGQGTQ VTVSSAAA HHHHHH GAAEQKLI SEEDLNGA A | 47 |
| XA8727 | 6 | QVQLVES GGGLVQA GGSLRLSC AAS | 12 | GFTFDDY A | 18 | IAWFRQA PGKEREG VSC | 24 | ISSSDGST | 30 | YYADSVK GRFTISRD NAKNTVY LQMNSLK PEDTAVYY C | 36 | AADLSRSC GRGYRYLE V | 42 | WGQGTQ VTVSSAAA HHHHHH GAAEQKLI SEEDLNGA A | 48 |

TABLE 3-continued

FRs and CDRs of MOR1 Nanobodies.

| Nanobody reference number | FR1 | SEQ ID NO: | CDR1 | SEQ ID NO: | FR2 | SEQ ID NO: | CDR2 | SEQ ID NO: | FR3 | SEQ ID NO: | CDR3 | SEQ ID NO: | FR4 | SEQ ID NO: |
|---|---|---|---|---|---|---|---|---|---|---|---|---|---|---|
| XA9644 | QVQLVES GGGLVQA GGSLRLSC AAS | 74 | GSIFSISA | 76 | MGWYRQ APGKQRE LVAT | 77 | ITSGGTT | 78 | NYADSVK GRFTISRD TAKNMVY LQMSSLKP EDTAVYYC | 79 | AADMEV WDYTDGD DDDY | 80 | WGQGTQ VTVSSAAA HHHHHH GAAEQKLI SEEDLNGA A | 81 |

TABLE 4

Examples of opioid receptors.

| Protein/subunit | Accession number (SEQ ID NO:) | AA sequence |
|---|---|---|
| P35372 (OPRM_HUMAN) Human mu-type opioid receptor | 50 | MDSSAAPTNASNCTDALAYSScSPAPSPGSWVNLSH LDGNLSDPCGPNRTDLGGRDSLCPPTGSPSMITAITIM ALYSIVCVVGLFGNFLVMYVIVRYTKMKTATNIYIFN LALADALATSTLPFQSVNYLMGTWPFGTILCKIVISID YYNMFTSIFTLCTMSVDRYIAVCHPVKALDFRTPRNA KIINVCNWILSSAIGLPVMFMATTKYRQGSIDCTLTFS HPTWYWENLLKICVFIFAFIMPVLIITVCYGLMILRLK SVRMLSGSKEKDRNLRRITRMVLVVVAVFIVCWTPI HIYVIIKALVTIPETTFQTVSWHFCIALGYTNSCLNPVL YAFLDENFKRCFREFCIPTSSNIEQQNSTRIRQNTRDH PSTANTVDRTNHQLENLEAETAPLP |
| P42866 (OPRM_MOUSE) Mouse mu-type receptor | 51 | MDSSAGPGNISDCSDPLAPASCSPAPGSWLNLSHVDG NQSDPCGPNRTGLGGSHSLCPQTGSPSMVTAITIMAL YSIVCVVGLFGNFLVMYVIVRYTKMKTATNIYIFNLA LADALATSTLPFQSVNYLMGTWPFGNILCKIVISIDYY NMFTSIFTLCTMSVDRYIAVCHPVKALDFRTPRNAKI VNVCNWILSSAIGLPVMFMATTKYRQGSIDCTLTFSH PTWYWENLLKICVFIFAFIMPVLIITVCYGLMILRLKS VRMLSGSKEKDRNLRRITRMVLVVVAVFIVCWTPIHI YVIIKALITIPETTFQTVSWHFCIALGYTNSCLNPVLYA FLDENFKRCFREFCIPTSSTIEQQNSARIRQNTREHPST ANTVDRTNHQLENLEAETAPLP |
| Delta mMor1 Recombinant mouse mu-type receptor | 52 | DYKDDDDAMGPGNISDCSDPLAPASCSPAPGSWLNL SHVDGNQSDPCGPNRTGLGENLYFQGSHSLCPQTGS PSMVTAITIMALYSIVCVVGLFGNFLVMYVIVRYTKM KTATNIYIFNLALADALATSTLPFQSVNYLMGTWPFG NILCKIVISIDYYNMFTSIFTLCTMSVDRYIAVCHPVK ALDFRTPRNAKIVNVCNWILSSAIGLPVMFMATTKYR QGSIDCTLTFSHPTWYWENLLKICVFIFAFIMPVLIITV CYGLMILRLKSVRMLSGSKEKDRNLRRITRMVLVVV AVFIVCWTPIHIYVIIKALITIPETTFQTVSWHFCIALGY TNSCLNPVLYAFLDENFKRCFREFCIPTSSTILEVLFQ GPEQQNSARIRQNTREHPSTANTVDRTNHQLENLEA ETAPLPDIHHHHHH Included cleavage sites in bold |
| P41145 (OPRK_HUMAN) Kappa-type opioid receptor | 53 | MDSPIQIFRGEPGPTCAPSACLPPNSSAWFPGWAEPDS NGSAGSEDAQLEPAHISPAIPVIITAVYSVVFVVGLVG NSLVMFVIIRYTKMKTATNIYIFNLALADALVTTTMP FQSTVYLMNSWPFGDVLCKIVISIDYYNMFTSIFTLT MMSVDRYIAVCHPVKALDFRTPLKAKIINICIWLLSSS VGISAIVLGGTKVREDVDVIECSLQFPDDDYSWWDLF MKICVFIFAFVIPVLIIIVCYTLMILRLKSVRLLSGSREK DRNLRRITRLVLVVVAVFVVCWTPIHIFILVEALGSTS HSTAALSSYYFCIALGYTNSSLNPILYAFLDENFKRCF RDFCFPLKMRMERQSTSRVRNTVQDPAYLRDIDGMN KPV |
| P41143 (OPRD_HUMAN) Delta-type opioid receptor | 54 | MEPAPSAGAELQPPLFANASDAYPSACPSAGANASG PPGARSASSLALAIAITALYSAVCAVGLLGNVLVMFG IVRYTKMKTATNIYIFNLALADALATSTLPFQSAKYL METWPFGELLCKAVLSIDYYNMFTSIFTLTMMSVDR YIAVCHPVKALDFRTPAKAKLINICIWVLASGVGVPI MVMAVTRPRDGAVVCMLQFPSPSWYWDTVTKICVF LFAFVVPILIITVCYGLMLLRLRSVRLLSGSKEKDRSL RRITRMVLVVVGAFVVCWAPIHIFVIVWTLVDIDRRD PLVVAALHLCIALGYANSSLNPVLYAFLDENFKRCFR QLCRKPCGRPDPSSFSRAREATARERVTACTPSDGPG GGAAA |
| P41146 (OPRX_HUMAN) Nociceptin receptor | 55 | MEPLFPAPFWEVIYGSHLQGNLSLLSPNHSLLPPHLLL NASHGAFLPLGLKVTIVGLYLAVCVGGLLGNCLVMY VILRHTKMKTATNIYIFNLALADTLVLLTLPFQGTDIL LGFWPFGNALCKTVIAIDYYNMFTSTFTLTAMSVDR YVAICHPIRALDVRTSSKAQAVNVAIWALASVVGVP VAIMGSAQVEDEEIECLVEIPTPQDYWGPVFAICIFLF SFIVPVLVISVCYSLMIRRLRGVRLLSGSREKDRNLRR ITRLVLVVVAVFVGCWTPVQVFVLAQGLGVQPSSET |

TABLE 4-continued

Examples of opioid receptors.

| Protein/subunit | Accession number (SEQ ID NO:) | AA sequence |
|---|---|---|
| | | AVAILRFCTALGYVNSCLNPILYAFLDENFKACFRKFCCASALRRDVQVSDRVRSIAKDVALACKTSETVPRPA |

TABLE 5

Immunization schedules - applying distinct immunogens - to generate a Mor1-specific serum conversion.

| Day | Llama Blanco | Llama Jumper | Llama Venus | Sample collection |
|---|---|---|---|---|
| 0 | TruncDelta mMor1 liposomes (100 µg total protein) Dmt1-Dalda (20 µM) Gerbu | hMor1/CHO membranes (1000 µg total protein) GTPγS (10 µM) Dmt1-Dalda (20 µM) Gerbu | Delta mMOR1/Sf9 membranes (2000 µg total protein) GTPγS (10 µM) Dmt1-Dalda (200 µM) | Pre-immune blood |
| 14 | TruncDelta mMor1 liposomes (100 µg) Dmt1-Dalda (20 µM) Gerbu | hMor1/CHO membranes (1000 µg total protein) GTPγS (10 µM) Dmt1-Dalda (20 µM) Gerbu | Delta mMOR1/Sf9 membranes 1000 µg total protein) GTPγS (10 µM) Dmt1-Dalda (200 µM) | — |
| 28 | TruncDelta mMor1 liposomes (50 µg) Dmt1-Dalda (20 µM) Gerbu | hMor1/CHO membranes (500 µg total protein) GTPγS (10 µM) Dmt1-Dalda (20 µM) Gerbu | Delta mMOR1/Sf9 membranes (1000 µg total protein) GTPγS (10 µM) Dmt1-Dalda (200 µM) | — |
| 35 | — | — | — | Immune blood |
| 42 | TruncDelta mMor1 liposomes (50 µg) Dmt1-Dalda (20 µM) Gerbu | hMor1/CHO membranes (500 µg total protein) GTPγS (10 µM) Dmt1-Dalda (20 µM) Gerbu | Delta mMOR1/Sf9 membranes (1000 µg total protein) GTPγS (10 µM) Dmt1-Dalda (200 µM) | — |
| 47 | — | — | — | Immune blood |

TABLE 6

Primer sequences.

| XAP1-FW-MfeI | CAGGTGCAatTGGTGGAGTCTGGGGGAGG | SEQ ID NO: 65 |
|---|---|---|
| VHH1-Rv-BamHI | AGTAGGATCCGCCACCTCCTGAGGAGACCGTGACCTGGGT | SEQ ID NO: 66 |
| VHH2-FW-BamHI | TCTTGGATCCGGCGGAGGTAGTCAGGTGCAGCTGCAGGAGTCTGGGGGAGG | SEQ ID NO: 67 |
| VHH2-Rv-BstEII | TGAGGAGACGGTGACCTGGGT | SEQ ID NO: 68 |

REFERENCES

Afonine, P. V. et al. Towards automated crystallographic structure refinement with phenix.refine. Acta crystallographica. Section D, Biological crystallography 68:352-367, doi:10.1107/S0907444912001308 (2012).

Binz et al. Nature Biotech. 22:575-582 (2004).

Caffrey (2003). Membrane protein crystallization. J Struct. Biol. 142:108-32.

Caffrey, M. and V. Cherezov. Crystallizing membrane proteins using lipidic mesophases. Nat. Protoc. 4:706-731, doi:10.1038/nprot.2009.31 (2009).

Chasin et al., 1986. Som. Cell Molec. Genet. 12:555-556.

Chelikani et al. Protein Sci. 2006 15:1433-40.

Choe, H. W. et al. Crystal structure of meta rhodopsin II. Nature 471:651-655, (2011).

Chun, E., A. A. Thompson, W. Liu, C. B. Roth, M. T. Griffith, V. Katritch, J. Kunken, F. Xu, V. Cherezov, M. A. Hanson and R. C. Stevens (2012). "Fusion partner toolchest for the stabilization and crystallization of G protein-coupled receptors." Structure 20(6):967-976.

Cooper, M. A. (2004). J. Mol. Recognit. 17:286-315.

Cox B. M. (2012). Recent developments in the study of opioid receptors. Mol. Pharm. 83:723-728.

Desmyter A., S. Spinelli, F. Payan, M. Lauwereys, L. Wyns, S. Muyldermans, and C. Cambillau. Three camelid VHH domains in complex with porcine pancreatic alpha-amylase. Inhibition and versatility of binding topology. J. Biol. Chem. 2002 Jun. 28; 277(26):23645-50.

Desmyter A, T. R. Transue, M. A. Ghahroudi, M. H. Thi, F. Poortmans, R. Hamers, S. Muyldermans, and L. Wyns. Crystal structure of a camel single-domain VH antibody fragment in complex with lysozyme. Nat. Struct. Biol. 1996 September; 3(9):803-11.

Deupi, X. et al. Stabilized G protein binding site in the structure of constitutively active metarhodopsin-II. Proc. Natl. Acad. Sci. U.S.A. 109:119-124, doi: 10.1073/pnas.1114089108 (2012).

Deveraux et al., 1984. Nucleic Acids Research 12:387-395.

Dimitrov D. S. Engineered CH2 domains (nanoantibodies). MAbs. 2009 January-February; 1(1):26-8.

Dosztányi, Z., V. Csizmok, P. Tompa, and I. Simon (2005).

Emsley, P. and K. Cowtan. Coot: model-building tools for molecular graphics. Acta crystallographica. Section D, Biological crystallography 60:2126-2132, doi: S0907444904019158 [pii] 10.1107/S0907444904019158 (2004).

Eroglu et al. EMBO 2002 3:491-496.

Eroglu et al. Proc. Natl. Acad. Sci. 2003 100:10219-10224.

Faham et al. Crystallization of bacteriorhodopsin from bicelle formulations at room temperature. Protein Sci. 2005 14:836-40.

Faham et al. Bicelle crystallization: a new method for crystallizing membrane proteins yields a monomeric bacteriorhodopsin structure. J. Mol. Biol. 2002 Feb. 8; 316(1):1-6.

Gebauer M. and A. Skerra. Engineered protein scaffolds as next-generation antibody therapeutics. Curr. Opin. Chem. Biol. 2009 June; 13(3):245-55.

George et al. Nat. Rev. Drug Discov. 1:808-820 (2002).

Gouaux, It's not just a phase: crystallization and X-ray structure determination of bacteriorhodopsin in lipidic cubic phases. Structure. 1998 6:5-10.

Groer C. E., K. Tidgewell, R. A. Moyer, W. W. Harding, R. B. Rothman, T. E. Prisinzano, and L. M. Bohn (2007). An opioid agonist that does not induce mu-opioid receptor/arrestin interactions or receptor internalization. Mol. Pharmacol. 71:549-557.

Gutstein H. B., and H. Akil (2001). Opioid analgesics. In: J. G. Hardman, L. E. Limbird, A. G. Gilman (eds), Goodman and Gilman's The pharmacological basis of therapeutics, 10th edn. McGraw Hill, New York, pp. 569-620.

Hamers-Casterman, C., T. Atarhouch, S. Muyldermans et al. Naturally occurring antibodies devoid of light chains. Nature 363:446-448, doi:10.1038/363446a0 (1993).

Jung Y., J. Y. Jeong, and B. H. Chung. Recent advances in immobilization methods of antibodies on solid supports. Analyst. 2008 June; 133(6):697-701. doi: 10.1039/b800014j. Epub 2008 Apr. 17.

Kabsch, W. Xds. Acta crystallographica. Section D, Biological crystallography 66:125-132, doi:10.1107/S0907444909047337 (2010).

Kallwass et al. Biotechnol. Lett., 15(1):29-34, 1993.

Kenakin, Trends Pharmacol. Sci. 25:186-192 (2002).

Kieffer B. L. (1999). Opioids: first lessons from knockout mice. Trends Pharmacol. Sci. 20:19-26.

Kieffer B. L., and C. Gaveriaux-Ruff (2002). Exploring the opioid system by gene knockout. Prog. Neurobiol. 66:285-306.

Kobilka, B. K. Amino and carboxyl terminal modifications to facilitate the production and purification of a G protein-coupled receptor. Anal. Biochem. 231:269-271 (1995).

Koide et al. J. Mol. Biol., 284:1141-1151 (1998).

Kolkekar et al., 1997, Biochemistry, 36:10901-10909.

Korotkov K. V., E. Pardon, J. Steyaert, and W. G. Hol. Crystal structure of the N-terminal domain of the secretin GspD from ETEC determined with the assistance of a nanobody. Structure 2009 Feb. 13; 17(2): 255-65.

Kruse A. C., A. M. Ring, A. Manglik, J. Hu, K. Hu, K. Eitel, H. Hubner, E. Pardon, C. Valant, P. M. Sexton, A. Christopoulos, C. C. Felder, P. Gmeiner, J. Steyaert, W. I. Weis, K. C. Garcia, J. Wess, and B. K. Kobilka. Activation and allosteric modulation of a muscarinic acetylcholine receptor. Nature 2013 504:101-6.

Lamb K., K. Tidgewell, D. S. Simpson, L. M. Bohn, and T. E. Prisinzano (2012). Antinociceptive effects of herkinorin, a MOP receptor agonist derived from salvinorin A in the formalin test in rats: new concepts in mu opioid receptor pharmacology. Drug Alcohol Depend. 121:181-188.

Landau et al. Lipidic cubic phases: a novel concept for the crystallization of membrane proteins. Proc. Natl. Acad. Sci. 1996 93:14532-5.

Lefranc, M. P., C. Pommie, et al. (2003). "IMGT unique numbering for immunoglobulin and T cell receptor variable domains and Ig superfamily V-like domains." Developmental and Comparative Immunology 27(1): 55-77.

Luca et al. Proc. Natl. Acad. Sci. 2003 100:10706-I 1.

Manglik A., A. C. Kruse, T. S. Kobilka, F. S. Thian, J. M. Mathiesen, R. K. Sunahara, L. Pardo, W. I. Weis, B. K. Kobilka, and S. Granier (2012). Crystal structure of the μ-opioid receptor bound to a morphinan antagonist. Nature, [Epub ahead of print]. [PMID:22437502].

Mansoor et al. Proc. Natl. Acad. Sci. 2006 103:3060-3065.

Mather, 1980, Biol. Reprod., 23:243-251.

Mather, 1982, Annals N.Y. Acad. Sci., 383:44-68.

Matthes H. W., R. Maldonado, F. Simonin, O. Valverde, S. Slowe, I. Kitchen, K. Befort, A. Dierich, M. LeMeur, P. Dolle', E. Tzavara, J. Hanoune, B. P. Rogues, and B. L. Kieffer (1996). Loss of morphine-induced analgesia, reward effect and withdrawal symptoms in mice lacking the mu-opioidreceptor gene. Nature 383:819-823.

McCoy, A. J. et al. Phaser crystallographic software. Journal of applied crystallography 40, 658-674, doi: 10.1107/S0021889807021206 (2007).

Niu et al. Biophys. J. 2005 89:1833-1840.

Nollert et al. Lipidic cubic phases as matrices for membrane protein crystallization. Methods 2004 34:348-53.

Nygaard, R. et al. The dynamic process of beta(2)-adrenergic receptor activation. Cell 152:532-542, doi: 10.1016/j.cell.2013.01.008 (2013).

Nygren, P.-A. (2008). Alternative binding proteins: affibody binding proteins developed from a small three-helix bundle scaffold. FEBS J. 275:2668-2676.

Pardon E., T. Laeremans, S. Triest, S. G. F. Rasmussen, A. Wohlkonig, A. Ruf, S. Muyldermans, W. G. J. Hol, B. K. Kobilka, and J. Steyaert. A general protocol for the generation of Nanobodies for structural biology. Nature Protocols (2014), in press.

Park J. H., P. Scheerer, K. P. Hofmann, H. W. Choe, and O. P. Ernst. Crystal structure of the ligand-free G-protein-coupled receptor opsin. Nature. 2008 Jul. 10; 454 (7201):183-7. doi: 10.1038/nature07063. Epub 2008 Jun. 18.

Pasternak G. W. (2013). Molecular biology of opioid analgesia. J. Pain Symptom Manage. 29:2-9.

Qian Z. M., H. Li, H. Sun and K. Ho (2002). Targeted drug delivery via the transferring receptor-mediated endocytosis pathway. Pharmacol. Rev. 54:561-587.

Rasmussen, S. G. et al. Crystal structure of the beta2 adrenergic receptor-Gs protein complex. *Nature* 477: 549-555, doi:10.1038/nature10361 (2011a).

Rasmussen, S. G., H. J. Choi, J. J. Fung, E. Pardon, P. Casarosa, P. S. Chae, B. T. Devree, D. M. Rosenbaum, F. S. Thian, T. S. Kobilka, A. Schnapp, I. Konetzki, R. K. Sunahara, S. H. Gellman, A. Pautsch, J. Steyaert, W. I. Weis and B. K. Kobilka (2011b). "Structure of a nanobody-stabilized active state of the beta(2) adrenoceptor." Nature 469(7329): 175-180.

Reeves et al., 2002. PNAS, 99:13419.

Riechmann and Muyldermans, J. Immunol. Methods 2000; 240:185-195.

Rios et al. Pharmacol. Ther. 92:71-87 (2001)).

Roy S., H. C. Liu, and H. H. Loh (1998). Mu-opioid receptor-knockout mice: the role of mu-opioid receptor in gastrointestinal transit. Brain Res. 56:281-283.

Rummel et al. Lipidic Cubic Phases: New Matrices for the Three-Dimensional Crystallization of Membrane Proteins. J. Struct. Biol. 1998 121:82-91.

Sawant R, and V. Torchilin. Intracellular transduction using cell-penetrating peptides. Mol. Biosyst. 2010 April; 6(4):628-40. Epub 2009 Dec. 21.

Scheerer, P. et al. Crystal structure of opsin in its G-protein-interacting conformation. *Nature* 455:497-502, doi:10.1038/nature07330 (2008).

Shimada et al. J. Biol. Chem. 2002 277:31774-80.

Skerra, J. Molecular Recognition, 13:167-187 (2000).

Sora I., N. Takahashi, M. Funada, H. Ujike, R. S. Revay, D. M. Donovan, L. L. Miner, and G. R. Uhl (1997). Opiate receptor knockout mice define mu receptor roles in endogenous nociceptive responses and morphine-induced analgesia. Proc. Natl. Acad. Sci. U.S.A. 94:1544-1549.

Starovasnik M. A., A. C. Braisted, and J. A. Wells. Structural mimicry of a native protein by a minimized binding domain. Proc. Natl. Acad. Sci. U.S.A. 1997 Sep. 16; 94(19): 10080-5.

Urlaub and Chasin, 1980, Proc. Natl. Acad. Sci. U.S.A., 77:4216.

Verheesen P., and T. Laeremans. Selection by phage display of single domain antibodies specific to antigens in their native conformation. In: D. Saerens and S. Muyldermans (eds), Single Domain Antibodies-Methods and Protocols. Springer protocols, Humana Press, pp 81-104.

Wesolowski, J., V. Alzogaray, J. Reyelt, M. Unger, K. Juarez, M. Urrutia, A. Cauerhiff, W. Danquah, B. Rissiek, F. Scheuplin, N. Schwarz, S. Adriouch, O. Boyer, M. Seman, A. Licea, D. V. Serreze, F. A. Goldbaum, F. Haag, and F. Koch-Nolte (2009). Single domain antibodies: promising experimental and therapeutic tools in infection and immunity. Med. Microbiol. Immunol. 198:157-174.

---

The invention claimed is:

1. A VHH antibody that binds specifically to an opioid receptor;
wherein the VHH antibody comprises an amino acid sequence comprising four framework regions (FR1 to FR4) and three complementary determining regions (CDR1 to CDR3); and
wherein CDR3 comprises the sequence of AARAPVGQSSSPYDYDY (SEQ ID NO:37).

2. The VHH antibody of claim 1, wherein the opioid receptor is from mammalian origin.

3. The VHH antibody of claim 1, wherein the opioid receptor is the mu-opioid receptor (MOR).

4. The VHH antibody of claim 1, wherein the VHH antibody is immobilized on a solid support.

5. A complex comprising an opioid receptor and the VHH antibody of claim 1.

6. The complex of claim 5, further comprising at least one other receptor ligand.

7. A composition comprising the complex of claim 5.

8. The composition of claim 7, wherein the composition is a cellular composition or a membrane composition.

9. A method for producing the VHH antibody of claim 1, the method comprising:
introducing a nucleic acid molecule encoding the VHH antibody into a host cell, and
expressing the nucleic acid molecule in the host cell so as to produce the VHH antibody.

10. A method of identifying conformation-selective compounds targeting an opioid receptor, the method comprising the steps of:
(i) providing a complex comprising an opioid receptor and the VHH antibody of claim 1;
(ii) providing a test compound; and
(iii) determining whether the test compound selectively binds the conformation of the opioid receptor as comprised in the complex.

11. A pharmaceutical composition comprising a therapeutically effective amount of the VHH antibody of claim 1 and at least one of a pharmaceutically acceptable carrier, adjuvant or diluents.

12. The VHH antibody of claim 1, wherein the opioid receptor is of human origin.

13. The VHH antibody of claim 1, wherein CDR1 is SEQ ID NO:14, and CDR2 is SEQ ID NO:26; or wherein CDR1 is SEQ ID NO:13 and CDR2 is SEQ ID NO: 25; or wherein CDR1 is SEQ ID NO:15 and CDR2 is SEQ ID NO:27; or wherein CDR1 is SEQ ID NO:16 and CDR2 is SEQ ID NO:28.

14. The VHH antibody of claim 1, wherein the VHH antibody comprises an amino acid sequence of SEQ ID NO: 2, 1, 3, or 4.

15. The VHH antibody of claim 1, wherein the VHH antibody interacts with residues from intracellular loop 2 (ICL2), ICL3, ICL4, or any combination thereof, of the opioid receptor.

* * * * *

SEQUENCE LISTING

```
<160> NUMBER OF SEQ ID NOS: 88

<210> SEQ ID NO 1
<211> LENGTH: 148
<212> TYPE: PRT
<213> ORGANISM: Lama glama

<400> SEQUENCE: 1

Gln Val Gln Leu Val Glu Ser Gly Gly Gly Leu Val Arg Pro Gly Gly
1               5                   10                  15

Ser Arg Arg Leu Ser Cys Val Asp Ser Glu Arg Thr Ser Tyr Pro Met
            20                  25                  30

Gly Trp Phe Arg Arg Ala Pro Gly Lys Glu Arg Glu Phe Val Ala Ser
        35                  40                  45

Ile Thr Trp Ser Gly Ile Asp Pro Thr Tyr Ala Asp Ser Val Ala Asp
    50                  55                  60

Arg Phe Thr Ile Ser Arg Asp Val Ala Asn Asn Thr Leu Tyr Leu Gln
65                  70                  75                  80

Met Asn Ser Leu Lys His Glu Asp Thr Ala Val Tyr Tyr Cys Ala Ala
                85                  90                  95

Arg Ala Pro Val Gly Gln Ser Ser Pro Tyr Asp Tyr Asp Tyr Trp
                100                 105                 110

Gly Gln Gly Thr Gln Val Thr Val Ser Ser Ala Ala Ala His His His
            115                 120                 125
```

```
His His His Gly Ala Ala Glu Gln Lys Leu Ile Ser Glu Glu Asp Leu
        130                 135                 140

Asn Gly Ala Ala
145

<210> SEQ ID NO 2
<211> LENGTH: 148
<212> TYPE: PRT
<213> ORGANISM: Lama glama

<400> SEQUENCE: 2

Gln Val Gln Leu Val Glu Ser Gly Gly Gly Leu Val Arg Pro Gly Gly
1               5                   10                  15

Ser Leu Arg Leu Ser Cys Val Asp Ser Glu Arg Thr Ser Tyr Pro Met
            20                  25                  30

Gly Trp Phe Arg Arg Ala Pro Gly Lys Glu Arg Glu Phe Val Ala Ser
        35                  40                  45

Ile Thr Trp Ser Gly Ile Asp Pro Thr Tyr Ala Asp Ser Val Ala Asp
    50                  55                  60

Arg Phe Thr Thr Ser Arg Asp Val Ala Asn Asn Thr Leu Tyr Leu Gln
65                  70                  75                  80

Met Asn Ser Leu Lys His Glu Asp Thr Ala Val Tyr Tyr Cys Ala Ala
                85                  90                  95

Arg Ala Pro Val Gly Gln Ser Ser Pro Tyr Asp Tyr Asp Tyr Trp
            100                 105                 110

Gly Gln Gly Thr Gln Val Thr Val Ser Ser Ala Ala Ala His His His
        115                 120                 125

His His His Gly Ala Ala Glu Gln Lys Leu Ile Ser Glu Glu Asp Leu
        130                 135                 140

Asn Gly Ala Ala
145

<210> SEQ ID NO 3
<211> LENGTH: 148
<212> TYPE: PRT
<213> ORGANISM: Lama glama

<400> SEQUENCE: 3

Gln Val Gln Leu Val Glu Ser Gly Gly Gly Leu Val Arg Pro Gly Gly
1               5                   10                  15

Ser Leu Arg Leu Ser Cys Val Asp Ser Gly Arg Thr Ser Tyr Pro Met
            20                  25                  30

Gly Trp Phe Arg Arg Ala Pro Gly Lys Glu Arg Glu Phe Val Ala Ser
        35                  40                  45

Ile Thr Trp Ser Gly Ile Asp Pro Thr Tyr Ala Asp Ser Val Ala Asp
    50                  55                  60

Arg Phe Thr Ile Ser Arg Asp Val Ala Asn Asn Thr Leu Tyr Leu Gln
65                  70                  75                  80

Met Asn Ser Leu Lys His Glu Asp Thr Ala Val Tyr Tyr Cys Ala Ala
                85                  90                  95

Arg Ala Pro Val Gly Gln Ser Ser Pro Tyr Asp Tyr Asp Tyr Trp
            100                 105                 110

Gly Gln Gly Thr Gln Val Thr Val Ser Ser Ala Ala Ala His His His
        115                 120                 125

His His His Gly Ala Ala Glu Gln Lys Leu Ile Ser Glu Glu Asp Leu
        130                 135                 140
```

Asn Gly Ala Ala
145

<210> SEQ ID NO 4
<211> LENGTH: 148
<212> TYPE: PRT
<213> ORGANISM: Lama glama

<400> SEQUENCE: 4

Gln Val Gln Leu Val Glu Ser Gly Gly Gly Leu Val Arg Pro Gly Gly
1               5                   10                  15

Ser Leu Arg Leu Ser Cys Val Asp Ser Glu Arg Thr Ser Tyr Pro Met
            20                  25                  30

Gly Trp Phe Arg Arg Ala Pro Gly Lys Glu Arg Glu Phe Val Ala Ser
        35                  40                  45

Ile Thr Trp Ser Gly Ile Asp Pro Thr Tyr Ala Asp Ser Val Ala Asp
    50                  55                  60

Arg Phe Thr Ile Ser Arg Asp Val Ala Asn Asn Thr Leu Tyr Leu Gln
65                  70                  75                  80

Met Asn Ser Leu Lys His Glu Asp Thr Ala Val Tyr Tyr Cys Ala Ala
                85                  90                  95

Arg Ala Pro Val Gly Gln Ser Ser Pro Tyr Asp Tyr Asp Tyr Trp
            100                 105                 110

Gly Gln Gly Thr Gln Val Thr Val Ser Ser Ala Ala His His His
        115                 120                 125

His His His Gly Ala Ala Glu Gln Lys Leu Ile Ser Glu Glu Asp Leu
    130                 135                 140

Asn Gly Ala Ala
145

<210> SEQ ID NO 5
<211> LENGTH: 149
<212> TYPE: PRT
<213> ORGANISM: Lama glama

<400> SEQUENCE: 5

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ser Ile Ser
            20                  25                  30

Thr Met Gly Trp Tyr Arg Gln Ala Pro Gly Asn Glu Arg Glu Leu Val
        35                  40                  45

Ala Ala Ile Thr Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Phe Lys Tyr Tyr Ser Gly Ser Tyr Phe Tyr Lys Ser Glu Tyr Asp Tyr
            100                 105                 110

Trp Gly Gln Gly Thr Gln Val Thr Val Ser Ser Ala Ala Ala His His
        115                 120                 125

His His His His Gly Ala Ala Glu Gln Lys Leu Ile Ser Glu Glu Asp
    130                 135                 140

Leu Asn Gly Ala Ala
145

```
<210> SEQ ID NO 6
<211> LENGTH: 150
<212> TYPE: PRT
<213> ORGANISM: Lama glama

<400> SEQUENCE: 6

Gln Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Phe Asp Asp Tyr
            20                  25                  30

Ala Ile Ala Trp Phe Arg Gln Ala Pro Gly Lys Glu Arg Glu Gly Val
        35                  40                  45

Ser Cys Ile Ser Ser Ser Asp Gly Ser Thr Tyr Tyr Ala Asp Ser Val
    50                  55                  60

Lys Gly Arg Phe Thr Ile Ser Asn Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Ser Arg Ser Cys Gly Arg Gly Tyr Arg Tyr Leu Glu
            100                 105                 110

Val Trp Gly Gln Gly Thr Gln Val Thr Val Ser Ser Ala Ala Ala His
        115                 120                 125

His His His His Gly Ala Ala Glu Gln Lys Leu Ile Ser Glu Glu
    130                 135                 140

Asp Leu Asn Gly Ala Ala
145                 150

<210> SEQ ID NO 7
<211> LENGTH: 25
<212> TYPE: PRT
<213> ORGANISM: Lama glama

<400> SEQUENCE: 7

Gln Val Gln Leu Val Glu Ser Gly Gly Gly Leu Val Arg Pro Gly Gly
1               5                   10                  15

Ser Arg Arg Leu Ser Cys Val Asp Ser
            20                  25

<210> SEQ ID NO 8
<211> LENGTH: 25
<212> TYPE: PRT
<213> ORGANISM: Lama glama

<400> SEQUENCE: 8

Gln Val Gln Leu Val Glu Ser Gly Gly Gly Leu Val Arg Pro Gly Gly
1               5                   10                  15

Ser Leu Arg Leu Ser Cys Val Asp Ser
            20                  25

<210> SEQ ID NO 9
<211> LENGTH: 25
<212> TYPE: PRT
<213> ORGANISM: Lama glama

<400> SEQUENCE: 9

Gln Val Gln Leu Val Glu Ser Gly Gly Gly Leu Val Arg Pro Gly Gly
1               5                   10                  15

Ser Leu Arg Leu Ser Cys Val Asp Ser
```

20                  25

<210> SEQ ID NO 10
<211> LENGTH: 25
<212> TYPE: PRT
<213> ORGANISM: Lama glama

<400> SEQUENCE: 10

Gln Val Gln Leu Val Glu Ser Gly Gly Gly Leu Val Arg Pro Gly Gly
1               5                   10                  15

Ser Leu Arg Leu Ser Cys Val Asp Ser
            20                  25

<210> SEQ ID NO 11
<211> LENGTH: 25
<212> TYPE: PRT
<213> ORGANISM: Lama glama

<400> SEQUENCE: 11

Gln Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 12
<211> LENGTH: 25
<212> TYPE: PRT
<213> ORGANISM: Lama glama

<400> SEQUENCE: 12

Gln Val Gln Leu Val Glu Ser Gly Gly Gly Leu Val Gln Ala Gly Gly
1               5                   10                  15

Ser Leu Arg Leu Ser Cys Ala Ala Ser
            20                  25

<210> SEQ ID NO 13
<211> LENGTH: 6
<212> TYPE: PRT
<213> ORGANISM: Lama glama

<400> SEQUENCE: 13

Glu Arg Thr Ser Tyr Pro
1               5

<210> SEQ ID NO 14
<211> LENGTH: 6
<212> TYPE: PRT
<213> ORGANISM: Lama glama

<400> SEQUENCE: 14

Glu Arg Thr Ser Tyr Pro
1               5

<210> SEQ ID NO 15
<211> LENGTH: 6
<212> TYPE: PRT
<213> ORGANISM: Lama glama

<400> SEQUENCE: 15

Gly Arg Thr Ser Tyr Pro
1               5

<210> SEQ ID NO 16

```
<211> LENGTH: 6
<212> TYPE: PRT
<213> ORGANISM: Lama glama

<400> SEQUENCE: 16

Glu Arg Thr Ser Tyr Pro
1               5

<210> SEQ ID NO 17
<211> LENGTH: 8
<212> TYPE: PRT
<213> ORGANISM: Lama glama

<400> SEQUENCE: 17

Gly Ser Ile Ser Ser Ile Ser Thr
1               5

<210> SEQ ID NO 18
<211> LENGTH: 8
<212> TYPE: PRT
<213> ORGANISM: Lama glama

<400> SEQUENCE: 18

Gly Phe Thr Phe Asp Asp Tyr Ala
1               5

<210> SEQ ID NO 19
<211> LENGTH: 17
<212> TYPE: PRT
<213> ORGANISM: Lama glama

<400> SEQUENCE: 19

Met Gly Trp Phe Arg Arg Ala Pro Gly Lys Glu Arg Glu Phe Val Ala
1               5                   10                  15

Ser

<210> SEQ ID NO 20
<211> LENGTH: 17
<212> TYPE: PRT
<213> ORGANISM: Lama glama

<400> SEQUENCE: 20

Met Gly Trp Phe Arg Arg Ala Pro Gly Lys Glu Arg Glu Phe Val Ala
1               5                   10                  15

Ser

<210> SEQ ID NO 21
<211> LENGTH: 17
<212> TYPE: PRT
<213> ORGANISM: Lama glama

<400> SEQUENCE: 21

Met Gly Trp Phe Arg Arg Ala Pro Gly Lys Glu Arg Glu Phe Val Ala
1               5                   10                  15

Ser

<210> SEQ ID NO 22
<211> LENGTH: 17
<212> TYPE: PRT
<213> ORGANISM: Lama glama

<400> SEQUENCE: 22

Met Gly Trp Phe Arg Arg Ala Pro Gly Lys Glu Arg Glu Phe Val Ala
```

-continued

```
                1               5                   10                  15

Ser

<210> SEQ ID NO 23
<211> LENGTH: 17
<212> TYPE: PRT
<213> ORGANISM: Lama glama

<400> SEQUENCE: 23

Met Gly Trp Tyr Arg Gln Ala Pro Gly Asn Glu Arg Glu Leu Val Ala
1               5                   10                  15

Ala

<210> SEQ ID NO 24
<211> LENGTH: 17
<212> TYPE: PRT
<213> ORGANISM: Lama glama

<400> SEQUENCE: 24

Ile Ala Trp Phe Arg Gln Ala Pro Gly Lys Glu Arg Glu Gly Val Ser
1               5                   10                  15

Cys

<210> SEQ ID NO 25
<211> LENGTH: 8
<212> TYPE: PRT
<213> ORGANISM: Lama glama

<400> SEQUENCE: 25

Ile Thr Trp Ser Gly Ile Asp Pro
1               5

<210> SEQ ID NO 26
<211> LENGTH: 8
<212> TYPE: PRT
<213> ORGANISM: Lama glama

<400> SEQUENCE: 26

Ile Thr Trp Ser Gly Ile Asp Pro
1               5

<210> SEQ ID NO 27
<211> LENGTH: 8
<212> TYPE: PRT
<213> ORGANISM: Lama glama

<400> SEQUENCE: 27

Ile Thr Trp Ser Gly Ile Asp Pro
1               5

<210> SEQ ID NO 28
<211> LENGTH: 8
<212> TYPE: PRT
<213> ORGANISM: Lama glama

<400> SEQUENCE: 28

Ile Thr Trp Ser Gly Ile Asp Pro
1               5

<210> SEQ ID NO 29
<211> LENGTH: 7
<212> TYPE: PRT
<213> ORGANISM: Lama glama
```

```
<400> SEQUENCE: 29

Ile Thr Ser Gly Gly Ser Thr
1               5

<210> SEQ ID NO 30
<211> LENGTH: 8
<212> TYPE: PRT
<213> ORGANISM: Lama glama

<400> SEQUENCE: 30

Ile Ser Ser Ser Asp Gly Ser Thr
1               5

<210> SEQ ID NO 31
<211> LENGTH: 38
<212> TYPE: PRT
<213> ORGANISM: Lama glama

<400> SEQUENCE: 31

Thr Tyr Ala Asp Ser Val Ala Asp Arg Phe Thr Ile Ser Arg Asp Val
1               5                  10                  15

Ala Asn Asn Thr Leu Tyr Leu Gln Met Asn Ser Leu Lys His Glu Asp
            20                  25                  30

Thr Ala Val Tyr Tyr Cys
        35

<210> SEQ ID NO 32
<211> LENGTH: 38
<212> TYPE: PRT
<213> ORGANISM: Lama glama

<400> SEQUENCE: 32

Thr Tyr Ala Asp Ser Val Ala Asp Arg Phe Thr Thr Ser Arg Asp Val
1               5                  10                  15

Ala Asn Asn Thr Leu Tyr Leu Gln Met Asn Ser Leu Lys His Glu Asp
            20                  25                  30

Thr Ala Val Tyr Tyr Cys
        35

<210> SEQ ID NO 33
<211> LENGTH: 38
<212> TYPE: PRT
<213> ORGANISM: Lama glama

<400> SEQUENCE: 33

Thr Tyr Ala Asp Ser Val Ala Asp Arg Phe Thr Ile Ser Arg Asp Val
1               5                  10                  15

Ala Asn Asn Thr Leu Tyr Leu Gln Met Asn Ser Leu Lys His Glu Asp
            20                  25                  30

Thr Ala Val Tyr Tyr Cys
        35

<210> SEQ ID NO 34
<211> LENGTH: 38
<212> TYPE: PRT
<213> ORGANISM: Lama glama

<400> SEQUENCE: 34

Thr Tyr Ala Asp Ser Val Ala Asp Arg Phe Thr Ile Ser Arg Asp Val
1               5                  10                  15
```

Ala Asn Asn Thr Leu Tyr Leu Gln Met Asn Ser Leu Lys His Glu Asp
                20                  25                  30

Thr Ala Val Tyr Tyr Cys
        35

<210> SEQ ID NO 35
<211> LENGTH: 38
<212> TYPE: PRT
<213> ORGANISM: Lama glama

<400> SEQUENCE: 35

Asn Tyr Ala Asp Ser Val Lys Gly Arg Phe Thr Ile Ser Arg Asp Asn
1               5                   10                  15

Ala Lys Asn Thr Val Tyr Leu Gln Met Asn Ser Leu Lys Pro Glu Asp
                20                  25                  30

Thr Ala Val Tyr Tyr Cys
        35

<210> SEQ ID NO 36
<211> LENGTH: 38
<212> TYPE: PRT
<213> ORGANISM: Lama glama

<400> SEQUENCE: 36

Tyr Tyr Ala Asp Ser Val Lys Gly Arg Phe Thr Ile Ser Asn Asp Asn
1               5                   10                  15

Ala Lys Asn Thr Val Tyr Leu Gln Met Asn Ser Leu Lys Pro Glu Asp
                20                  25                  30

Thr Ala Val Tyr Tyr Cys
        35

<210> SEQ ID NO 37
<211> LENGTH: 17
<212> TYPE: PRT
<213> ORGANISM: Lama glama

<400> SEQUENCE: 37

Ala Ala Arg Ala Pro Val Gly Gln Ser Ser Pro Tyr Asp Tyr Asp
1               5                   10                  15

Tyr

<210> SEQ ID NO 38
<211> LENGTH: 17
<212> TYPE: PRT
<213> ORGANISM: Lama glama

<400> SEQUENCE: 38

Ala Ala Arg Ala Pro Val Gly Gln Ser Ser Pro Tyr Asp Tyr Asp
1               5                   10                  15

Tyr

<210> SEQ ID NO 39
<211> LENGTH: 17
<212> TYPE: PRT
<213> ORGANISM: Lama glama

<400> SEQUENCE: 39

Ala Ala Arg Ala Pro Val Gly Gln Ser Ser Pro Tyr Asp Tyr Asp
1               5                   10                  15

Tyr

<210> SEQ ID NO 40
<211> LENGTH: 17
<212> TYPE: PRT
<213> ORGANISM: Lama glama

<400> SEQUENCE: 40

Ala Ala Arg Ala Pro Val Gly Gln Ser Ser Ser Pro Tyr Asp Tyr Asp
1               5                   10                  15
Tyr

<210> SEQ ID NO 41
<211> LENGTH: 17
<212> TYPE: PRT
<213> ORGANISM: Lama glama

<400> SEQUENCE: 41

Asn Phe Lys Tyr Tyr Ser Gly Ser Tyr Phe Tyr Lys Ser Glu Tyr Asp
1               5                   10                  15
Tyr

<210> SEQ ID NO 42
<211> LENGTH: 17
<212> TYPE: PRT
<213> ORGANISM: Lama glama

<400> SEQUENCE: 42

Ala Ala Asp Leu Ser Arg Ser Cys Gly Arg Gly Tyr Arg Tyr Leu Glu
1               5                   10                  15
Val

<210> SEQ ID NO 43
<211> LENGTH: 37
<212> TYPE: PRT
<213> ORGANISM: Lama glama

<400> SEQUENCE: 43

Trp Gly Gln Gly Thr Gln Val Thr Val Ser Ser Ala Ala Ala His His
1               5                   10                  15

His His His His Gly Ala Ala Glu Gln Lys Leu Ile Ser Glu Glu Asp
                20                  25                  30

Leu Asn Gly Ala Ala
            35

<210> SEQ ID NO 44
<211> LENGTH: 37
<212> TYPE: PRT
<213> ORGANISM: Lama glama

<400> SEQUENCE: 44

Trp Gly Gln Gly Thr Gln Val Thr Val Ser Ser Ala Ala Ala His His
1               5                   10                  15

His His His His Gly Ala Ala Glu Gln Lys Leu Ile Ser Glu Glu Asp
                20                  25                  30

Leu Asn Gly Ala Ala
            35

<210> SEQ ID NO 45
<211> LENGTH: 37
<212> TYPE: PRT
<213> ORGANISM: Lama glama

```
<400> SEQUENCE: 45

Trp Gly Gln Gly Thr Gln Val Thr Val Ser Ser Ala Ala Ala His His
1               5                   10                  15

His His His His Gly Ala Ala Glu Gln Lys Leu Ile Ser Glu Glu Asp
            20                  25                  30

Leu Asn Gly Ala Ala
        35

<210> SEQ ID NO 46
<211> LENGTH: 37
<212> TYPE: PRT
<213> ORGANISM: Lama glama

<400> SEQUENCE: 46

Trp Gly Gln Gly Thr Gln Val Thr Val Ser Ser Ala Ala Ala His His
1               5                   10                  15

His His His His Gly Ala Ala Glu Gln Lys Leu Ile Ser Glu Glu Asp
            20                  25                  30

Leu Asn Gly Ala Ala
        35

<210> SEQ ID NO 47
<211> LENGTH: 37
<212> TYPE: PRT
<213> ORGANISM: Lama glama

<400> SEQUENCE: 47

Trp Gly Gln Gly Thr Gln Val Thr Val Ser Ser Ala Ala Ala His His
1               5                   10                  15

His His His His Gly Ala Ala Glu Gln Lys Leu Ile Ser Glu Glu Asp
            20                  25                  30

Leu Asn Gly Ala Ala
        35

<210> SEQ ID NO 48
<211> LENGTH: 37
<212> TYPE: PRT
<213> ORGANISM: Lama glama

<400> SEQUENCE: 48

Trp Gly Gln Gly Thr Gln Val Thr Val Ser Ser Ala Ala Ala His His
1               5                   10                  15

His His His His Gly Ala Ala Glu Gln Lys Leu Ile Ser Glu Glu Asp
            20                  25                  30

Leu Asn Gly Ala Ala
        35

<210> SEQ ID NO 49
<211> LENGTH: 278
<212> TYPE: PRT
<213> ORGANISM: Lama glama

<400> SEQUENCE: 49

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ser Ser Ile Ser
            20                  25                  30

Thr Met Gly Trp Tyr Arg Gln Ala Pro Gly Asn Glu Arg Glu Leu Val
        35                  40                  45
```

```
Ala Ala Ile Thr Ser Gly Gly Ser Thr Asn Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Asn
                 85                  90                  95

Phe Lys Tyr Tyr Ser Gly Ser Tyr Phe Tyr Lys Ser Glu Tyr Asp Tyr
                100                 105                 110

Trp Gly Gln Gly Thr Gln Val Thr Val Ser Ser Gly Gly Gly Gly Ser
            115                 120                 125

Gly Gly Gly Ser Gln Val Gln Leu Gln Glu Ser Gly Gly Gly Leu Val
        130                 135                 140

Gln Ala Gly Gly Ser Leu Arg Leu Ser Cys Ala Ala Ser Gly Ser Ile
145                 150                 155                 160

Ser Ser Ile Ser Thr Met Gly Trp Tyr Arg Gln Ala Pro Gly Asn Glu
                165                 170                 175

Arg Glu Leu Val Ala Ala Ile Thr Ser Gly Gly Ser Thr Asn Tyr Ala
                180                 185                 190

Asp Ser Val Lys Gly Arg Phe Thr Ile Ser Arg Asp Asn Ala Lys Asn
            195                 200                 205

Thr Val Tyr Leu Gln Met Asn Ser Leu Lys Pro Glu Asp Thr Ala Val
210                 215                 220

Tyr Tyr Cys Asn Phe Lys Tyr Tyr Ser Gly Ser Tyr Phe Tyr Lys Ser
225                 230                 235                 240

Glu Tyr Asp Tyr Trp Gly Gln Gly Thr Gln Val Thr Val Ser Ser Ala
                245                 250                 255

Ala Ala Glu Gln Lys Leu Ile Ser Glu Glu Asp Leu Asn Gly Ala Ala
            260                 265                 270

His His His His His His
            275

<210> SEQ ID NO 50
<211> LENGTH: 400
<212> TYPE: PRT
<213> ORGANISM: Homo sapiens

<400> SEQUENCE: 50

Met Asp Ser Ser Ala Ala Pro Thr Asn Ala Ser Asn Cys Thr Asp Ala
 1               5                  10                  15

Leu Ala Tyr Ser Ser Cys Ser Pro Ala Pro Ser Pro Gly Ser Trp Val
                 20                  25                  30

Asn Leu Ser His Leu Asp Gly Asn Leu Ser Asp Pro Cys Gly Pro Asn
             35                  40                  45

Arg Thr Asp Leu Gly Gly Arg Asp Ser Leu Cys Pro Pro Thr Gly Ser
         50                  55                  60

Pro Ser Met Ile Thr Ala Ile Thr Ile Met Ala Leu Tyr Ser Ile Val
 65                  70                  75                  80

Cys Val Val Gly Leu Phe Gly Asn Phe Leu Val Met Tyr Val Ile Val
                 85                  90                  95

Arg Tyr Thr Lys Met Lys Thr Ala Thr Asn Ile Tyr Ile Phe Asn Leu
                100                 105                 110

Ala Leu Ala Asp Ala Leu Ala Thr Ser Thr Leu Pro Phe Gln Ser Val
            115                 120                 125

Asn Tyr Leu Met Gly Thr Trp Pro Phe Gly Thr Ile Leu Cys Lys Ile
        130                 135                 140
```

Val Ile Ser Ile Asp Tyr Tyr Asn Met Phe Thr Ser Ile Phe Thr Leu
145                 150                 155                 160

Cys Thr Met Ser Val Asp Arg Tyr Ile Ala Val Cys His Pro Val Lys
            165                 170                 175

Ala Leu Asp Phe Arg Thr Pro Arg Asn Ala Lys Ile Ile Asn Val Cys
        180                 185                 190

Asn Trp Ile Leu Ser Ser Ala Ile Gly Leu Pro Val Met Phe Met Ala
    195                 200                 205

Thr Thr Lys Tyr Arg Gln Gly Ser Ile Asp Cys Thr Leu Thr Phe Ser
210                 215                 220

His Pro Thr Trp Tyr Trp Glu Asn Leu Leu Lys Ile Cys Val Phe Ile
225                 230                 235                 240

Phe Ala Phe Ile Met Pro Val Leu Ile Ile Thr Val Cys Tyr Gly Leu
                245                 250                 255

Met Ile Leu Arg Leu Lys Ser Val Arg Met Leu Ser Gly Ser Lys Glu
            260                 265                 270

Lys Asp Arg Asn Leu Arg Arg Ile Thr Arg Met Val Leu Val Val Val
        275                 280                 285

Ala Val Phe Ile Val Cys Trp Thr Pro Ile His Ile Tyr Val Ile Ile
    290                 295                 300

Lys Ala Leu Val Thr Ile Pro Glu Thr Thr Phe Gln Thr Val Ser Trp
305                 310                 315                 320

His Phe Cys Ile Ala Leu Gly Tyr Thr Asn Ser Cys Leu Asn Pro Val
                325                 330                 335

Leu Tyr Ala Phe Leu Asp Glu Asn Phe Lys Arg Cys Phe Arg Glu Phe
            340                 345                 350

Cys Ile Pro Thr Ser Ser Asn Ile Glu Gln Gln Asn Ser Thr Arg Ile
        355                 360                 365

Arg Gln Asn Thr Arg Asp His Pro Ser Thr Ala Asn Thr Val Asp Arg
    370                 375                 380

Thr Asn His Gln Leu Glu Asn Leu Glu Ala Glu Thr Ala Pro Leu Pro
385                 390                 395                 400

<210> SEQ ID NO 51
<211> LENGTH: 398
<212> TYPE: PRT
<213> ORGANISM: Mus musculus

<400> SEQUENCE: 51

Met Asp Ser Ser Ala Gly Pro Gly Asn Ile Ser Asp Cys Ser Asp Pro
1               5                   10                  15

Leu Ala Pro Ala Ser Cys Ser Pro Ala Pro Gly Ser Trp Leu Asn Leu
            20                  25                  30

Ser His Val Asp Gly Asn Gln Ser Asp Pro Cys Gly Pro Asn Arg Thr
        35                  40                  45

Gly Leu Gly Gly Ser His Ser Leu Cys Pro Gln Thr Gly Ser Pro Ser
    50                  55                  60

Met Val Thr Ala Ile Thr Ile Met Ala Leu Tyr Ser Ile Val Cys Val
65                  70                  75                  80

Val Gly Leu Phe Gly Asn Phe Leu Val Met Tyr Val Ile Val Arg Tyr
                85                  90                  95

Thr Lys Met Lys Thr Ala Thr Asn Ile Tyr Ile Phe Asn Leu Ala Leu
            100                 105                 110

Ala Asp Ala Leu Ala Thr Ser Thr Leu Pro Phe Gln Ser Val Asn Tyr

```
                    115                 120                 125
Leu Met Gly Thr Trp Pro Phe Gly Asn Ile Leu Cys Lys Ile Val Ile
    130                 135                 140

Ser Ile Asp Tyr Tyr Asn Met Phe Thr Ser Ile Phe Thr Leu Cys Thr
145                 150                 155                 160

Met Ser Val Asp Arg Tyr Ile Ala Val Cys His Pro Val Lys Ala Leu
                165                 170                 175

Asp Phe Arg Thr Pro Arg Asn Ala Lys Ile Val Asn Val Cys Asn Trp
            180                 185                 190

Ile Leu Ser Ser Ala Ile Gly Leu Pro Val Met Phe Met Ala Thr Thr
        195                 200                 205

Lys Tyr Arg Gln Gly Ser Ile Asp Cys Thr Leu Thr Phe Ser His Pro
    210                 215                 220

Thr Trp Tyr Trp Glu Asn Leu Leu Lys Ile Cys Val Phe Ile Phe Ala
225                 230                 235                 240

Phe Ile Met Pro Val Leu Ile Ile Thr Val Cys Tyr Gly Leu Met Ile
                245                 250                 255

Leu Arg Leu Lys Ser Val Arg Met Leu Ser Gly Ser Lys Glu Lys Asp
            260                 265                 270

Arg Asn Leu Arg Arg Ile Thr Arg Met Val Leu Val Val Val Ala Val
        275                 280                 285

Phe Ile Val Cys Trp Thr Pro Ile His Ile Tyr Val Ile Ile Lys Ala
    290                 295                 300

Leu Ile Thr Ile Pro Glu Thr Thr Phe Gln Thr Val Ser Trp His Phe
305                 310                 315                 320

Cys Ile Ala Leu Gly Tyr Thr Asn Ser Cys Leu Asn Pro Val Leu Tyr
                325                 330                 335

Ala Phe Leu Asp Glu Asn Phe Lys Arg Cys Phe Arg Glu Phe Cys Ile
            340                 345                 350

Pro Thr Ser Ser Thr Ile Glu Gln Gln Asn Ser Ala Arg Ile Arg Gln
        355                 360                 365

Asn Thr Arg Glu His Pro Ser Thr Ala Asn Thr Val Asp Arg Thr Asn
    370                 375                 380

His Gln Leu Glu Asn Leu Glu Ala Glu Thr Ala Pro Leu Pro
385                 390                 395

<210> SEQ ID NO 52
<211> LENGTH: 424
<212> TYPE: PRT
<213> ORGANISM: Mus musculus

<400> SEQUENCE: 52

Asp Tyr Lys Asp Asp Asp Ala Met Gly Pro Gly Asn Ile Ser Asp
1               5                   10                  15

Cys Ser Asp Pro Leu Ala Pro Ala Ser Cys Ser Pro Ala Pro Gly Ser
                20                  25                  30

Trp Leu Asn Leu Ser His Val Asp Gly Asn Gln Ser Asp Pro Cys Gly
            35                  40                  45

Pro Asn Arg Thr Gly Leu Gly Glu Asn Leu Tyr Phe Gln Gly Ser His
        50                  55                  60

Ser Leu Cys Pro Gln Thr Gly Ser Pro Ser Met Val Thr Ala Ile Thr
65                  70                  75                  80

Ile Met Ala Leu Tyr Ser Ile Val Cys Val Val Gly Leu Phe Gly Asn
                85                  90                  95
```

Phe Leu Val Met Tyr Val Ile Val Arg Tyr Thr Lys Met Lys Thr Ala
                100                 105                 110

Thr Asn Ile Tyr Ile Phe Asn Leu Ala Leu Ala Asp Ala Leu Ala Thr
            115                 120                 125

Ser Thr Leu Pro Phe Gln Ser Val Asn Tyr Leu Met Gly Thr Trp Pro
        130                 135                 140

Phe Gly Asn Ile Leu Cys Lys Ile Val Ile Ser Ile Asp Tyr Tyr Asn
145                 150                 155                 160

Met Phe Thr Ser Ile Phe Thr Leu Cys Thr Met Ser Val Asp Arg Tyr
                165                 170                 175

Ile Ala Val Cys His Pro Val Lys Ala Leu Asp Phe Arg Thr Pro Arg
            180                 185                 190

Asn Ala Lys Ile Val Asn Val Cys Asn Trp Ile Leu Ser Ser Ala Ile
        195                 200                 205

Gly Leu Pro Val Met Phe Met Ala Thr Thr Lys Tyr Arg Gln Gly Ser
            210                 215                 220

Ile Asp Cys Thr Leu Thr Phe Ser His Pro Thr Trp Tyr Trp Glu Asn
225                 230                 235                 240

Leu Leu Lys Ile Cys Val Phe Ile Phe Ala Phe Ile Met Pro Val Leu
                245                 250                 255

Ile Ile Thr Val Cys Tyr Gly Leu Met Ile Leu Arg Leu Lys Ser Val
            260                 265                 270

Arg Met Leu Ser Gly Ser Lys Glu Lys Asp Arg Asn Leu Arg Arg Ile
        275                 280                 285

Thr Arg Met Val Leu Val Val Ala Val Phe Ile Val Cys Trp Thr
            290                 295                 300

Pro Ile His Ile Tyr Val Ile Ile Lys Ala Leu Ile Thr Ile Pro Glu
305                 310                 315                 320

Thr Thr Phe Gln Thr Val Ser Trp His Phe Cys Ile Ala Leu Gly Tyr
                325                 330                 335

Thr Asn Ser Cys Leu Asn Pro Val Leu Tyr Ala Phe Leu Asp Glu Asn
            340                 345                 350

Phe Lys Arg Cys Phe Arg Glu Phe Cys Ile Pro Thr Ser Ser Thr Ile
        355                 360                 365

Leu Glu Val Leu Phe Gln Gly Pro Glu Gln Gln Asn Ser Ala Arg Ile
370                 375                 380

Arg Gln Asn Thr Arg Glu His Pro Ser Thr Ala Asn Thr Val Asp Arg
385                 390                 395                 400

Thr Asn His Gln Leu Glu Asn Leu Glu Ala Glu Thr Ala Pro Leu Pro
                405                 410                 415

Asp Ile His His His His His His
            420

<210> SEQ ID NO 53
<211> LENGTH: 380
<212> TYPE: PRT
<213> ORGANISM: Homo sapiens

<400> SEQUENCE: 53

Met Asp Ser Pro Ile Gln Ile Phe Arg Gly Glu Pro Gly Pro Thr Cys
1               5                   10                  15

Ala Pro Ser Ala Cys Leu Pro Pro Asn Ser Ser Ala Trp Phe Pro Gly
            20                  25                  30

Trp Ala Glu Pro Asp Ser Asn Gly Ser Ala Gly Ser Glu Asp Ala Gln
        35                  40                  45

```
Leu Glu Pro Ala His Ile Ser Pro Ala Ile Pro Val Ile Ile Thr Ala
 50                  55                  60

Val Tyr Ser Val Val Phe Val Gly Leu Val Gly Asn Ser Leu Val
 65                  70                  75                  80

Met Phe Val Ile Ile Arg Tyr Thr Lys Met Lys Thr Ala Thr Asn Ile
                 85                  90                  95

Tyr Ile Phe Asn Leu Ala Leu Ala Asp Ala Leu Val Thr Thr Thr Met
                100                 105                 110

Pro Phe Gln Ser Thr Val Tyr Leu Met Asn Ser Trp Pro Phe Gly Asp
                115                 120                 125

Val Leu Cys Lys Ile Val Ile Ser Ile Asp Tyr Tyr Asn Met Phe Thr
                130                 135                 140

Ser Ile Phe Thr Leu Thr Met Met Ser Val Asp Arg Tyr Ile Ala Val
145                 150                 155                 160

Cys His Pro Val Lys Ala Leu Asp Phe Arg Thr Pro Leu Lys Ala Lys
                165                 170                 175

Ile Ile Asn Ile Cys Ile Trp Leu Leu Ser Ser Val Gly Ile Ser
                180                 185                 190

Ala Ile Val Leu Gly Gly Thr Lys Val Arg Glu Asp Val Asp Val Ile
                195                 200                 205

Glu Cys Ser Leu Gln Phe Pro Asp Asp Asp Tyr Ser Trp Trp Asp Leu
                210                 215                 220

Phe Met Lys Ile Cys Val Phe Ile Phe Ala Phe Val Ile Pro Val Leu
225                 230                 235                 240

Ile Ile Ile Val Cys Tyr Thr Leu Met Ile Leu Arg Leu Lys Ser Val
                245                 250                 255

Arg Leu Leu Ser Gly Ser Arg Glu Lys Asp Arg Asn Leu Arg Arg Ile
                260                 265                 270

Thr Arg Leu Val Leu Val Val Ala Val Phe Val Val Cys Trp Thr
                275                 280                 285

Pro Ile His Ile Phe Ile Leu Val Glu Ala Leu Gly Ser Thr Ser His
                290                 295                 300

Ser Thr Ala Ala Leu Ser Ser Tyr Tyr Phe Cys Ile Ala Leu Gly Tyr
305                 310                 315                 320

Thr Asn Ser Ser Leu Asn Pro Ile Leu Tyr Ala Phe Leu Asp Glu Asn
                325                 330                 335

Phe Lys Arg Cys Phe Arg Asp Phe Cys Phe Pro Leu Lys Met Arg Met
                340                 345                 350

Glu Arg Gln Ser Thr Ser Arg Val Arg Asn Thr Val Gln Asp Pro Ala
                355                 360                 365

Tyr Leu Arg Asp Ile Asp Gly Met Asn Lys Pro Val
370                 375                 380

<210> SEQ ID NO 54
<211> LENGTH: 372
<212> TYPE: PRT
<213> ORGANISM: Homo sapiens

<400> SEQUENCE: 54

Met Glu Pro Ala Pro Ser Ala Gly Ala Glu Leu Gln Pro Pro Leu Phe
  1               5                  10                  15

Ala Asn Ala Ser Asp Ala Tyr Pro Ser Ala Cys Pro Ser Ala Gly Ala
                 20                  25                  30

Asn Ala Ser Gly Pro Pro Gly Ala Arg Ser Ala Ser Ser Leu Ala Leu
```

```
            35                  40                  45
Ala Ile Ala Ile Thr Ala Leu Tyr Ser Ala Val Cys Ala Val Gly Leu
         50                  55                  60

Leu Gly Asn Val Leu Val Met Phe Gly Ile Val Arg Tyr Thr Lys Met
 65                  70                  75                  80

Lys Thr Ala Thr Asn Ile Tyr Ile Phe Asn Leu Ala Leu Ala Asp Ala
                 85                  90                  95

Leu Ala Thr Ser Thr Leu Pro Phe Gln Ser Ala Lys Tyr Leu Met Glu
            100                 105                 110

Thr Trp Pro Phe Gly Glu Leu Leu Cys Lys Ala Val Leu Ser Ile Asp
        115                 120                 125

Tyr Tyr Asn Met Phe Thr Ser Ile Phe Thr Leu Thr Met Met Ser Val
    130                 135                 140

Asp Arg Tyr Ile Ala Val Cys His Pro Val Lys Ala Leu Asp Phe Arg
145                 150                 155                 160

Thr Pro Ala Lys Ala Lys Leu Ile Asn Ile Cys Ile Trp Val Leu Ala
                165                 170                 175

Ser Gly Val Gly Val Pro Ile Met Val Met Ala Val Thr Arg Pro Arg
            180                 185                 190

Asp Gly Ala Val Val Cys Met Leu Gln Phe Pro Ser Pro Ser Trp Tyr
        195                 200                 205

Trp Asp Thr Val Thr Lys Ile Cys Val Phe Leu Phe Ala Phe Val Val
    210                 215                 220

Pro Ile Leu Ile Ile Thr Val Cys Tyr Gly Leu Met Leu Leu Arg Leu
225                 230                 235                 240

Arg Ser Val Arg Leu Leu Ser Gly Ser Lys Glu Lys Asp Arg Ser Leu
                245                 250                 255

Arg Arg Ile Thr Arg Met Val Leu Val Val Gly Ala Phe Val Val
            260                 265                 270

Cys Trp Ala Pro Ile His Ile Phe Val Ile Val Trp Thr Leu Val Asp
        275                 280                 285

Ile Asp Arg Arg Asp Pro Leu Val Val Ala Ala Leu His Leu Cys Ile
    290                 295                 300

Ala Leu Gly Tyr Ala Asn Ser Ser Leu Asn Pro Val Leu Tyr Ala Phe
305                 310                 315                 320

Leu Asp Glu Asn Phe Lys Arg Cys Phe Arg Gln Leu Cys Arg Lys Pro
                325                 330                 335

Cys Gly Arg Pro Asp Pro Ser Ser Phe Ser Arg Ala Arg Glu Ala Thr
            340                 345                 350

Ala Arg Glu Arg Val Thr Ala Cys Thr Pro Ser Asp Gly Pro Gly Gly
        355                 360                 365

Gly Ala Ala Ala
    370

<210> SEQ ID NO 55
<211> LENGTH: 370
<212> TYPE: PRT
<213> ORGANISM: Homo sapiens

<400> SEQUENCE: 55

Met Glu Pro Leu Phe Pro Ala Pro Phe Trp Glu Val Ile Tyr Gly Ser
1               5                  10                  15

His Leu Gln Gly Asn Leu Ser Leu Leu Ser Pro Asn His Ser Leu Leu
            20                  25                  30
```

```
Pro Pro His Leu Leu Asn Ala Ser His Gly Ala Phe Leu Pro Leu
        35                  40                  45

Gly Leu Lys Val Thr Ile Val Gly Leu Tyr Leu Ala Val Cys Val Gly
 50                  55                  60

Gly Leu Leu Gly Asn Cys Leu Val Met Tyr Val Ile Leu Arg His Thr
 65                  70                  75                  80

Lys Met Lys Thr Ala Thr Asn Ile Tyr Ile Phe Asn Leu Ala Leu Ala
                 85                  90                  95

Asp Thr Leu Val Leu Leu Thr Leu Pro Phe Gln Gly Thr Asp Ile Leu
                100                 105                 110

Leu Gly Phe Trp Pro Phe Gly Asn Ala Leu Cys Lys Thr Val Ile Ala
            115                 120                 125

Ile Asp Tyr Tyr Asn Met Phe Thr Ser Thr Phe Thr Leu Thr Ala Met
130                 135                 140

Ser Val Asp Arg Tyr Val Ala Ile Cys His Pro Ile Arg Ala Leu Asp
145                 150                 155                 160

Val Arg Thr Ser Ser Lys Ala Gln Ala Val Asn Val Ala Ile Trp Ala
                165                 170                 175

Leu Ala Ser Val Val Gly Val Pro Val Ala Ile Met Gly Ser Ala Gln
            180                 185                 190

Val Glu Asp Glu Glu Ile Glu Cys Leu Val Glu Ile Pro Thr Pro Gln
        195                 200                 205

Asp Tyr Trp Gly Pro Val Phe Ala Ile Cys Ile Phe Leu Phe Ser Phe
    210                 215                 220

Ile Val Pro Val Leu Val Ile Ser Val Cys Tyr Ser Leu Met Ile Arg
225                 230                 235                 240

Arg Leu Arg Gly Val Arg Leu Leu Ser Gly Ser Arg Glu Lys Asp Arg
                245                 250                 255

Asn Leu Arg Arg Ile Thr Arg Leu Val Leu Val Val Val Ala Val Phe
            260                 265                 270

Val Gly Cys Trp Thr Pro Val Gln Val Phe Val Leu Ala Gln Gly Leu
        275                 280                 285

Gly Val Gln Pro Ser Ser Glu Thr Ala Val Ala Ile Leu Arg Phe Cys
290                 295                 300

Thr Ala Leu Gly Tyr Val Asn Ser Cys Leu Asn Pro Ile Leu Tyr Ala
305                 310                 315                 320

Phe Leu Asp Glu Asn Phe Lys Ala Cys Phe Arg Lys Phe Cys Cys Ala
                325                 330                 335

Ser Ala Leu Arg Arg Asp Val Gln Val Ser Asp Arg Val Arg Ser Ile
            340                 345                 350

Ala Lys Asp Val Ala Leu Ala Cys Lys Thr Ser Glu Thr Val Pro Arg
                355                 360                 365

Pro Ala
    370

<210> SEQ ID NO 56
<211> LENGTH: 10
<212> TYPE: PRT
<213> ORGANISM: Artificial Sequence
<220> FEATURE:
<223> OTHER INFORMATION: Linker

<400> SEQUENCE: 56

Gly Ser Gly Ser Gly Ser Gly Ser Gly Ser
1               5                   10
```

<210> SEQ ID NO 57
<211> LENGTH: 20
<212> TYPE: PRT
<213> ORGANISM: Artificial Sequence
<220> FEATURE:
<223> OTHER INFORMATION: Linker

<400> SEQUENCE: 57

Gly Ser Gly Ser Gly Ser Gly Ser Gly Ser Gly Ser Gly Ser Gly Ser
1               5                   10                  15

Gly Ser Gly Ser
            20

<210> SEQ ID NO 58
<211> LENGTH: 15
<212> TYPE: PRT
<213> ORGANISM: Artificial Sequence
<220> FEATURE:
<223> OTHER INFORMATION: Linker

<400> SEQUENCE: 58

Gly Gly Gly Gly Ser Gly Gly Gly Ser Gly Gly Gly Gly Ser
1               5                   10                  15

<210> SEQ ID NO 59
<211> LENGTH: 17
<212> TYPE: PRT
<213> ORGANISM: Artificial Sequence
<220> FEATURE:
<223> OTHER INFORMATION: Linker

<400> SEQUENCE: 59

Ala His His Ser Glu Asp Pro Ser Ser Lys Ala Pro Lys Ala Pro Met
1               5                   10                  15

Ala

<210> SEQ ID NO 60
<211> LENGTH: 16
<212> TYPE: PRT
<213> ORGANISM: Artificial Sequence
<220> FEATURE:
<223> OTHER INFORMATION: Linker

<400> SEQUENCE: 60

Ser Pro Ser Thr Pro Pro Thr Pro Ser Pro Ser Thr Pro Pro Ala Ser
1               5                   10                  15

<210> SEQ ID NO 61
<211> LENGTH: 4
<212> TYPE: PRT
<213> ORGANISM: Artificial Sequence
<220> FEATURE:
<223> OTHER INFORMATION: Factor Xa cleavage site

<400> SEQUENCE: 61

Ile Glu Gly Arg
1

<210> SEQ ID NO 62
<211> LENGTH: 4
<212> TYPE: PRT
<213> ORGANISM: Artificial Sequence
<220> FEATURE:
<223> OTHER INFORMATION: thrombin cleavage site

<400> SEQUENCE: 62

```
Leu Val Pro Arg
1

<210> SEQ ID NO 63
<211> LENGTH: 5
<212> TYPE: PRT
<213> ORGANISM: Artificial Sequence
<220> FEATURE:
<223> OTHER INFORMATION: enterokinase cleaving site

<400> SEQUENCE: 63

Asp Asp Asp Asp Lys
1               5

<210> SEQ ID NO 64
<211> LENGTH: 8
<212> TYPE: PRT
<213> ORGANISM: Artificial Sequence
<220> FEATURE:
<223> OTHER INFORMATION: PreScission -or 3C- cleavage site

<400> SEQUENCE: 64

Leu Glu Val Leu Phe Gln Gly Pro
1               5

<210> SEQ ID NO 65
<211> LENGTH: 29
<212> TYPE: DNA
<213> ORGANISM: Artificial Sequence
<220> FEATURE:
<223> OTHER INFORMATION: Primer

<400> SEQUENCE: 65
caggtgcaat tggtggagtc tgggggagg                                  29

<210> SEQ ID NO 66
<211> LENGTH: 40
<212> TYPE: DNA
<213> ORGANISM: Artificial Sequence
<220> FEATURE:
<223> OTHER INFORMATION: Primer

<400> SEQUENCE: 66
agtaggatcc gccacctcct gaggagaccg tgacctgggt                      40

<210> SEQ ID NO 67
<211> LENGTH: 51
<212> TYPE: DNA
<213> ORGANISM: Artificial Sequence
<220> FEATURE:
<223> OTHER INFORMATION: Primer

<400> SEQUENCE: 67
tcttggatcc ggcggaggta gtcaggtgca gctgcaggag tctgggggag g         51

<210> SEQ ID NO 68
<211> LENGTH: 21
<212> TYPE: DNA
<213> ORGANISM: Artificial Sequence
<220> FEATURE:
<223> OTHER INFORMATION: Primer

<400> SEQUENCE: 68
tgaggagacg gtgacctggg t                                          21
```

-continued

```
<210> SEQ ID NO 69
<211> LENGTH: 8
<212> TYPE: PRT
<213> ORGANISM: Artificial Sequence
<220> FEATURE:
<223> OTHER INFORMATION: Flag tag encoding AA sequence

<400> SEQUENCE: 69

Asp Tyr Lys Asp Asp Asp Asp Ala
1               5

<210> SEQ ID NO 70
<211> LENGTH: 4
<212> TYPE: PRT
<213> ORGANISM: Artificial Sequence
<220> FEATURE:
<223> OTHER INFORMATION: AA residues 2-5

<400> SEQUENCE: 70

Asp Ser Ser Ala
1

<210> SEQ ID NO 71
<211> LENGTH: 6
<212> TYPE: PRT
<213> ORGANISM: Artificial Sequence
<220> FEATURE:
<223> OTHER INFORMATION: TEV cleavage site

<400> SEQUENCE: 71

Glu Asn Leu Tyr Phe Gln
1               5

<210> SEQ ID NO 72
<211> LENGTH: 8
<212> TYPE: PRT
<213> ORGANISM: Artificial Sequence
<220> FEATURE:
<223> OTHER INFORMATION: 3C site

<400> SEQUENCE: 72

Leu Glu Val Leu Phe Gln Gly Pro
1               5

<210> SEQ ID NO 73
<211> LENGTH: 8
<212> TYPE: PRT
<213> ORGANISM: Artificial Sequence
<220> FEATURE:
<223> OTHER INFORMATION: histidine tag coding sequence

<400> SEQUENCE: 73

Asp Ile His His His His His His
1               5

<210> SEQ ID NO 74
<211> LENGTH: 149
<212> TYPE: PRT
<213> ORGANISM: Lama glama

<400> SEQUENCE: 74

Gln Val Gln Leu Val Glu Ser Gly Gly Gly Leu Val Arg Pro Gly Gly
1               5                   10                  15

Ser Leu Arg Leu Ser Cys Val Asp Ser Glu Arg Ile Phe Ser Ile Ser
            20                  25                  30

Ala Met Gly Trp Tyr Arg Gln Ala Pro Gly Lys Gln Arg Glu Leu Val
```

```
                35                  40                  45
Ala Thr Ile Thr Ser Gly Gly Thr Thr Asn Tyr Ala Asp Ser Val Lys
 50                  55                  60

Gly Arg Phe Thr Ile Ser Gly Asp Thr Ala Lys Asn Met Val Tyr Leu
 65                  70                  75                  80

Gln Met Ser Ser Leu Lys Pro Glu Asp Thr Ala Val Tyr Tyr Cys Ala
                 85                  90                  95

Ala Asp Met Glu Val Trp Asp Tyr Thr Asp Gly Asp Asp Asp Asp Tyr
            100                 105                 110

Trp Gly Gln Gly Thr Gln Val Thr Val Ser Ser Ala Ala His His
        115                 120                 125

His His His His Gly Ala Ala Glu Gln Lys Leu Ile Ser Glu Glu Asp
130                 135                 140

Leu Asn Gly Ala Ala
145

<210> SEQ ID NO 75
<211> LENGTH: 25
<212> TYPE: PRT
<213> ORGANISM: Lama glama

<400> SEQUENCE: 75

Gln Val Gln Leu Val Glu Ser Gly Gly Leu Val Gln Ala Gly Gly
1               5                  10                  15

Ser Leu Arg Leu Ser Cys Val Ala Ser
             20                  25

<210> SEQ ID NO 76
<211> LENGTH: 8
<212> TYPE: PRT
<213> ORGANISM: Lama glama

<400> SEQUENCE: 76

Gly Ser Ile Phe Ser Ile Ser Ala
1               5

<210> SEQ ID NO 77
<211> LENGTH: 17
<212> TYPE: PRT
<213> ORGANISM: Lama glama

<400> SEQUENCE: 77

Met Gly Trp Tyr Arg Gln Ala Pro Gly Lys Gln Arg Glu Leu Val Ala
1               5                  10                  15

Thr

<210> SEQ ID NO 78
<211> LENGTH: 7
<212> TYPE: PRT
<213> ORGANISM: Lama glama

<400> SEQUENCE: 78

Ile Thr Ser Gly Gly Thr Thr
1               5

<210> SEQ ID NO 79
<211> LENGTH: 38
<212> TYPE: PRT
<213> ORGANISM: Lama glama

<400> SEQUENCE: 79
```

```
Asn Tyr Ala Asp Ser Val Lys Gly Arg Phe Thr Ile Ser Gly Asp Thr
1               5                   10                  15

Ala Lys Asn Met Val Tyr Leu Gln Met Ser Ser Leu Lys Pro Glu Asp
            20                  25                  30

Thr Ala Val Tyr Tyr Cys
        35

<210> SEQ ID NO 80
<211> LENGTH: 17
<212> TYPE: PRT
<213> ORGANISM: Lama glama

<400> SEQUENCE: 80

Ala Ala Asp Met Glu Val Trp Asp Tyr Thr Asp Gly Asp Asp Asp Asp
1               5                   10                  15

Tyr

<210> SEQ ID NO 81
<211> LENGTH: 37
<212> TYPE: PRT
<213> ORGANISM: Lama glama

<400> SEQUENCE: 81

Trp Gly Gln Gly Thr Gln Val Thr Val Ser Ser Ala Ala Ala His His
1               5                   10                  15

His His His His Gly Ala Ala Glu Gln Lys Leu Ile Ser Glu Glu Asp
            20                  25                  30

Leu Asn Gly Ala Ala
        35

<210> SEQ ID NO 82
<211> LENGTH: 148
<212> TYPE: PRT
<213> ORGANISM: Lama glama

<400> SEQUENCE: 82

Gln Val Gln Leu Val Glu Ser Gly Gly Gly Leu Val Arg Pro Gly Gly
1               5                   10                  15

Ser Arg Arg Leu Ser Cys Val Asp Ser Glu Arg Thr Ser Tyr Pro Met
            20                  25                  30

Gly Trp Phe Arg Arg Ala Pro Gly Lys Glu Arg Glu Phe Val Ala Ser
        35                  40                  45

Ile Thr Trp Ser Gly Ile Asp Pro Thr Tyr Ala Asp Ser Val Ala Asp
    50                  55                  60

Arg Phe Thr Ile Ser Arg Asp Val Ala Asn Asn Thr Leu Tyr Leu Gln
65                  70                  75                  80

Met Asn Ser Leu Lys His Glu Asp Thr Ala Val Tyr Tyr Cys Ala Ala
                85                  90                  95

Arg Ala Pro Val Gly Gln Ser Ser Pro Tyr Asp Tyr Asp Tyr Trp
            100                 105                 110

Gly Gln Gly Thr Gln Val Thr Val Ser Ser Ala Ala Ala His His His
        115                 120                 125

His His His Gly Ala Ala Glu Gln Lys Leu Ile Ser Glu Glu Asp Leu
    130                 135                 140

Asn Gly Ala Ala
145
```

```
<210> SEQ ID NO 83
<211> LENGTH: 148
<212> TYPE: PRT
<213> ORGANISM: Lama glama

<400> SEQUENCE: 83

Gln Val Gln Leu Val Glu Ser Gly Gly Gly Leu Val Arg Pro Gly Gly
1               5                   10                  15

Ser Leu Arg Leu Ser Cys Val Asp Ser Glu Arg Thr Ser Tyr Pro Met
            20                  25                  30

Gly Trp Phe Arg Arg Ala Pro Gly Lys Glu Arg Glu Phe Val Ala Ser
        35                  40                  45

Ile Thr Trp Ser Gly Ile Asp Pro Thr Tyr Ala Asp Ser Val Ala Asp
    50                  55                  60

Arg Phe Thr Thr Ser Arg Asp Val Ala Asn Asn Thr Leu Tyr Leu Gln
65                  70                  75                  80

Met Asn Ser Leu Lys His Glu Asp Thr Ala Val Tyr Tyr Cys Ala Ala
                85                  90                  95

Arg Ala Pro Val Gly Gln Ser Ser Pro Tyr Asp Tyr Asp Tyr Trp
            100                 105                 110

Gly Gln Gly Thr Gln Val Thr Val Ser Ser Ala Ala Ala His His His
        115                 120                 125

His His His Gly Ala Ala Glu Gln Lys Leu Ile Ser Glu Glu Asp Leu
    130                 135                 140

Asn Gly Ala Ala
145

<210> SEQ ID NO 84
<211> LENGTH: 148
<212> TYPE: PRT
<213> ORGANISM: Lama glama

<400> SEQUENCE: 84

Gln Val Gln Leu Val Glu Ser Gly Gly Gly Leu Val Arg Pro Gly Gly
1               5                   10                  15

Ser Arg Arg Leu Ser Cys Val Asp Ser Gly Arg Thr Ser Tyr Pro Met
            20                  25                  30

Gly Trp Phe Arg Arg Ala Pro Gly Lys Glu Arg Glu Phe Val Ala Ser
        35                  40                  45

Ile Thr Trp Ser Gly Ile Asp Pro Thr Tyr Ala Asp Ser Val Ala Asp
    50                  55                  60

Arg Phe Thr Ile Ser Arg Asp Val Ala Asn Asn Thr Leu Tyr Leu Gln
65                  70                  75                  80

Met Asn Ser Leu Lys His Glu Asp Thr Ala Val Tyr Tyr Cys Ala Ala
                85                  90                  95

Arg Ala Pro Val Gly Gln Ser Ser Pro Tyr Asp Tyr Asp Tyr Trp
            100                 105                 110

Gly Gln Gly Thr Gln Val Thr Val Ser Ser Ala Ala Ala His His His
        115                 120                 125

His His His Gly Ala Ala Glu Gln Lys Leu Ile Ser Glu Glu Asp Leu
    130                 135                 140

Asn Gly Ala Ala
145

<210> SEQ ID NO 85
<211> LENGTH: 148
<212> TYPE: PRT
```

<213> ORGANISM: Lama glama

<400> SEQUENCE: 85

Gln Val Gln Leu Val Glu Ser Gly Gly Gly Leu Val Arg Pro Gly Gly
1               5                   10                  15

Ser Leu Arg Leu Ser Cys Val Asp Ser Glu Arg Thr Ser Tyr Pro Met
            20                  25                  30

Gly Trp Phe Arg Arg Ala Pro Gly Lys Glu Arg Glu Phe Val Ala Ser
        35                  40                  45

Ile Thr Trp Ser Gly Ile Asp Pro Thr Tyr Ala Asp Ser Val Ala Asp
    50                  55                  60

Arg Phe Thr Ile Ser Arg Asp Val Ala Asn Asn Thr Leu Tyr Leu Gln
65                  70                  75                  80

Met Asn Ser Leu Lys His Glu Asp Thr Ala Val Tyr Tyr Cys Ala Ala
                85                  90                  95

Arg Ala Pro Val Gly Gln Ser Ser Pro Tyr Asp Tyr Asp Tyr Trp
            100                 105                 110

Gly Gln Gly Thr Gln Val Thr Val Ser Ser Ala Ala Ala His His
        115                 120                 125

His His His Gly Ala Ala Glu Gln Lys Leu Ile Ser Glu Glu Asp Leu
    130                 135                 140

Asn Gly Ala Ala
145

<210> SEQ ID NO 86
<211> LENGTH: 149
<212> TYPE: PRT
<213> ORGANISM: Lama glama

<400> SEQUENCE: 86

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Ser Ile Ser
            20                  25                  30

Thr Met Gly Trp Tyr Arg Gln Ala Pro Gly Asn Glu Arg Glu Leu Val
        35                  40                  45

Ala Ala Ile Thr Ser Gly Gly Ser Thr Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Phe Lys Tyr Tyr Ser Gly Ser Tyr Phe Tyr Lys Ser Glu Tyr Asp Tyr
            100                 105                 110

Trp Gly Gln Gly Thr Gln Val Thr Val Ser Ser Ala Ala Ala His His
        115                 120                 125

His His His His Gly Ala Ala Glu Gln Lys Leu Ile Ser Glu Glu Asp
    130                 135                 140

Leu Asn Gly Ala Ala
145

<210> SEQ ID NO 87
<211> LENGTH: 150
<212> TYPE: PRT
<213> ORGANISM: Lama glama

<400> SEQUENCE: 87

```
Gln Val Gln Leu Val Glu Ser Gly Gly Leu Val Gln Ala Gly Gly
1               5                   10                  15

Ser Leu Arg Leu Ser Cys Ala Ala Ser Gly Phe Thr Phe Asp Asp Tyr
                20                  25                  30

Ala Ile Ala Trp Phe Arg Gln Ala Pro Gly Lys Glu Arg Glu Gly Val
        35                  40                  45

Ser Cys Ile Ser Ser Ser Asp Gly Ser Thr Tyr Tyr Ala Asp Ser Val
    50                  55                  60

Lys Gly Arg Phe Thr Ile Ser Asn Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Leu Ser Arg Ser Cys Gly Arg Gly Tyr Arg Tyr Leu Glu
            100                 105                 110

Val Trp Gly Gln Gly Thr Gln Val Thr Val Ser Ser Ala Ala Ala His
        115                 120                 125

His His His His His Gly Ala Ala Glu Gln Lys Leu Ile Ser Glu Glu
    130                 135                 140

Asp Leu Asn Gly Ala Ala
145             150

<210> SEQ ID NO 88
<211> LENGTH: 11
<212> TYPE: PRT
<213> ORGANISM: Artificial Sequence
<220> FEATURE:
<223> OTHER INFORMATION: synthesized sequence

<400> SEQUENCE: 88

Tyr Gly Arg Lys Lys Arg Arg Gln Arg Arg Arg
1               5                   10
```